US006403374B1

(12) United States Patent
Tsien et al.

(10) Patent No.: US 6,403,374 B1
(45) Date of Patent: *Jun. 11, 2002

(54) LONG WAVELENGTH ENGINEERED FLUORESCENT PROTEINS

(75) Inventors: Roger Y. Tsien, La Jolla, CA (US); S. James Remington, Eugene, OR (US); Andrew B. Cubitt, San Diego; Roger Heim, Del Mar, both of CA (US); Mats F. Ormö, Huddinge (SE)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/465,142

(22) Filed: Dec. 16, 1999

Related U.S. Application Data

(63) Continuation of application No. 08/974,737, filed on Nov. 19, 1997, now Pat. No. 6,077,707, which is a continuation of application No. 08/911,825, filed on Aug. 15, 1997, now Pat. No. 6,054,321, which is a continuation-in-part of application No. 08/706,408, filed on Aug. 30, 1996, now Pat. No. 6,124,128

(60) Provisional application No. 60/024,050, filed on Aug. 16, 1996.

(51) Int. Cl.[7] ............................. C12N 5/00; C07H 21/04
(52) U.S. Cl. ..................... 435/325; 435/410; 435/252.3; 435/252.33; 435/254.11; 435/320.1; 536/23.1; 536/23.6; 536/23.4
(58) Field of Search ...................... 435/252.3, 252.33, 435/325, 410, 320.1, 254.11; 536/23.1, 23.4, 23.6; 530/350

(56) References Cited

U.S. PATENT DOCUMENTS

| | | | |
|---|---|---|---|
| 5,491,084 A | 2/1996 | Chalfie et al. | 435/189 |
| 5,625,048 A | 4/1997 | Tsien et al. | 536/23.4 |
| 5,777,079 A | 7/1998 | Tsien et al. | 530/350 |
| 5,795,737 A | 8/1998 | Seed et al. | 435/69.1 |
| 5,804,387 A | 9/1998 | Cormack et al. | 435/6 |

FOREIGN PATENT DOCUMENTS

| | | |
|---|---|---|
| WO | WO 91/01305 | 2/1991 |
| WO | WO 95/07463 | 3/1995 |
| WO | WO 95/21191 | 8/1995 |
| WO | WO 96/23810 | 8/1996 |
| WO | WO 96/23898 | 8/1996 |
| WO | WO 96/27027 | 9/1996 |
| WO | WO 96/27675 | 9/1996 |
| WO | WO 97/26333 | 1/1997 |
| WO | WO 97/11094 | 3/1997 |
| WO | WO 97/42320 | 5/1997 |
| WO | WO 97/28261 | 8/1997 |

OTHER PUBLICATIONS

Baldwin et al. Biochemistry 29 5509–5915 (1990).
Chalfie et al. Science 263 802–804 (1994).
Cheng et al Nature Biotechnology 14 606–609 (1996).
Cody et al Biochemistry 32 1212–1218 (1993).
Cormack, et al., Gene 173 33–38 (1996).
Chattoraj et al Proc. Natl. Acad. Sci 93 8362–8367 (1996).
Crameri et al. Nature Biotech. 14 315–319 (1996).
Cubitt et al., Trends in Biochem. Sci. 20:488–455 (1995).
Delagrave et al. Bio/Technology 13 151–154 (1995).
Dickson et al., Science 274 966–969 (1996).
Ehrig et al. FEBS Letters 367 163–166 (1995).
Giuliano et al Ann. Rev. Biophys. Biomol. Struc 24 405–435 (1995).

(List continued on next page.)

Primary Examiner—Nashaat T. Nashed
(74) Attorney, Agent, or Firm—Gray Cary Ware & Freidenrich LLP; Lisa A. Haile

(57) ABSTRACT

Engineered fluorescent proteins, nucleic acids encoding them and methods of use are provided.

23 Claims, 53 Drawing Sheets

OTHER PUBLICATIONS

Heim et al. Proc. Natl. Acad. Sci. 91 12501–12505 (1994).
Heim et al Nature 373 663–664 (1995).
Heim et al., Current Biology 6:178–182 (Feb. 1996).
Inouye and Tsuji FEBS Lett 341 277–280 (1994).
Kain et al, BioTechniques 19:650–655 (1995).
Levine et al. Comp. Biochem. Physiol. 72B 77–85 (1982).
Mitra et al Gene 173 13–17 (1996).
Muhlrad et al Yeast 8 79–82 (1992).
Norris et al Plant Molecular Biology 24 673–677 (1994).
Niwa, et al. Proc. Natl. Acad. Sci. 93 13617–13622 (1996).
Ormo et al. Science 273 1392–1395 (1996).
Perozzo et al J. Biol. Chem. 263 7713–7716 (1988).
Prasher et al. Gene 111 229–233 (1992).
Roth Thesis from the graduate program in Biochemistry from Rutgers, the state University of New Jersey (Oct. 1985).
Ward in Bioluminescence and Chemiluminescence (eds DeLuca et al., 235–242 (Academic Press, NY, 1981).
Ward et al Biochemistry 21 4535–4540 (1982).
Ward et al Photochem Photobiol. 35 803–808 (1982).
Yang et al. Nature Biotechnology 14 1246–1251.
Yokoe and Meyer Nature Biotech 14 1252–1256 (1996).
Zolotukhin et al., 70 4646–4654 (1996).
S. Delagrave and D. Youvan, "Searching sequence space to engineer proteins: exponential ensemble mutagenesis," Bio Technology, 11:1548–1552 (Dec., 1993).

(xi) SEQUENCE DESCRIPTION:

SEQ ID NO:1:

SEQ ID NO:2:

| ATG | AGT | AAA | GGA | GAA | GAA | CTT | TTC | ACT | GGA | GTT | GTC | CCA | ATT | CTT | GTT | 48 |
| Met | Ser | Lys | Gly | Glu | Glu | Leu | Phe | Thr | Gly | Val | Val | Pro | Ile | Leu | Val | |
| 1 | | | | 5 | | | | | 10 | | | | | 15 | | |
| GAA | TTA | GAT | GGT | GAT | GTT | AAT | GGG | CAC | AAA | TTT | TCT | GTC | AGT | GGA | GAG | 96 |
| Glu | Leu | Asp | Gly | Asp | Val | Asn | Gly | His | Lys | Phe | Ser | Val | Ser | Gly | Glu | |
| | | | 20 | | | | | 25 | | | | | 30 | | | |
| GGT | GAA | GGT | GAT | GCA | ACA | TAC | GGA | AAA | CTT | ACC | CTT | AAA | TTT | ATT | TGC | 144 |
| Gly | Glu | Gly | Asp | Ala | Thr | Tyr | Gly | Lys | Leu | Thr | Leu | Lys | Phe | Ile | Cys | |
| | | 35 | | | | | 40 | | | | | 45 | | | | |
| ACT | ACT | GGA | AAA | CTA | CCT | GTT | CCA | TGG | CCA | ACA | CTT | GTC | ACT | ACT | TTC | 192 |
| Thr | Thr | Gly | Lys | Leu | Pro | Val | Pro | Trp | Pro | Thr | Leu | Val | Thr | Thr | Phe | |
| | 50 | | | | | 55 | | | | | 60 | | | | | |
| TCT | TAT | GGT | GTT | CAA | TGC | TTT | TCA | AGA | TAC | CCA | GAT | CAT | ATG | AAA | CGG | 240 |
| Ser | Tyr | Gly | Val | Gln | Cys | Phe | Ser | Arg | Tyr | Pro | Asp | His | Met | Lys | Arg | |
| 65 | | | | | 70 | | | | | 75 | | | | | 80 | |
| CAT | GAC | TTT | TTC | AAG | AGT | GCC | ATG | CCC | GAA | GGT | TAT | GTA | CAG | GAA | AGA | 288 |
| His | Asp | Phe | Phe | Lys | Ser | Ala | Met | Pro | Glu | Gly | Tyr | Val | Gln | Glu | Arg | |
| | | | | 85 | | | | | 90 | | | | | 95 | | |
| ACT | ATA | TTT | TTC | AAA | GAT | GAC | GGG | AAC | TAC | AAG | ACA | CGT | GCT | GAA | GTC | 336 |
| Thr | Ile | Phe | Phe | Lys | Asp | Asp | Gly | Asn | Tyr | Lys | Thr | Arg | Ala | Glu | Val | |
| | | | | 100 | | | | | 105 | | | | | 110 | | |
| AAG | TTT | GAA | GGT | GAT | ACC | CTT | GTT | AAT | AGA | ATC | GAG | TTA | AAA | GGT | ATT | 384 |
| Lys | Phe | Glu | Gly | Asp | Thr | Leu | Val | Asn | Arg | Ile | Glu | Leu | Lys | Gly | Ile | |
| | | | | 115 | | | | | 120 | | | | | 125 | | |
| GAT | TTT | AAA | GAA | GAT | GGA | AAC | ATT | CTT | GGA | CAC | AAA | TTG | GAA | TAC | AAC | 432 |
| Asp | Phe | Lys | Glu | Asp | Gly | Asn | Ile | Leu | Gly | His | Lys | Leu | Glu | Tyr | Asn | |
| | 130 | | | | | 135 | | | | | 140 | | | | | |
| TAT | AAC | TCA | CAC | AAT | GTA | TAC | ATC | ATG | GCA | GAC | AAA | CAA | AAG | AAT | GGA | 480 |
| Tyr | Asn | Ser | His | Asn | Val | Tyr | Ile | Met | Ala | Asp | Lys | Gln | Lys | Asn | Gly | |
| 145 | | | | | 150 | | | | | 155 | | | | | 160 | |
| ATC | AAA | GTT | AAC | TTC | AAA | ATT | AGA | CAC | AAC | ATT | GAA | GAT | GGA | AGC | GTT | 528 |
| Ile | Lys | Val | Asn | Phe | Lys | Ile | Arg | His | Asn | Ile | Glu | Asp | Gly | Ser | Val | |
| | | | | 165 | | | | | 170 | | | | | 175 | | |
| CAA | CTA | GCA | GAC | CAT | TAT | CAA | CAA | AAT | ACT | CCA | ATT | GGC | GAT | GGC | CCT | 576 |
| Gln | Leu | Ala | Asp | His | Tyr | Gln | Gln | Asn | Thr | Pro | Ile | Gly | Asp | Gly | Pro | |
| | | | 180 | | | | | 185 | | | | | 190 | | | |
| GTC | CTT | TTA | CCA | GAC | AAC | CAT | TAC | CTG | TCC | ACA | CAA | TCT | GCC | CTT | TCG | 624 |
| Val | Leu | Leu | Pro | Asp | Asn | His | Tyr | Leu | Ser | Thr | Gln | Ser | Ala | Leu | Ser | |
| | | | 195 | | | | | 200 | | | | | 205 | | | |
| AAA | GAT | CCC | AAC | GAA | AAG | AGA | GAC | CAC | ATG | GTC | CTT | CTT | GAG | TTT | GTA | 672 |
| Lys | Asp | Pro | Asn | Glu | Lys | Arg | Asp | His | Met | Val | Leu | Leu | Glu | Phe | Val | |
| | 210 | | | | | 215 | | | | | 220 | | | | | |
| ACA | GCT | GCT | GGG | ATT | ACA | CAT | GGC | ATG | GAT | GAA | CTA | TAC | AAA | TA | | 717 |
| Thr | Ala | Ala | Gly | Ile | Thr | His | Gly | Met | Asp | Glu | Leu | Tyr | Lys | | | |
| 225 | | | | | 230 | | | | | 235 | | | | | | |

FIG. 3

T203Y, S65G, S72A humanized codon usage, with an additional amino acid ater the start met to provide optimal kozak sequence

```
         9          18          27          36          45          54
ATG GTG AGC AAG GGC GAG GAG CTG TTC ACC GGG GTG GTG CCC ATC CTG GTC GAG
--- --- --- --- --- --- --- --- --- --- --- --- --- --- --- --- --- ---
Met Val Ser Lys Gly Glu Glu Leu Phe Thr Gly Val Val Pro Ile Leu Val Glu 63          72          81          90          99         108
CTG GAC GGC GAC GTA AAC GGC CAC AAG TTC AGC GTG TCC GGC GAG GGC GAG GGC
--- --- --- --- --- --- --- --- --- --- --- --- --- --- --- --- --- ---
Leu Asp Gly Asp Val Asn Gly His Lys Phe Ser Val Ser Gly Glu Gly Glu Gly 117         126         135         144         153         162
GAT GCC ACC TAC GGC AAG CTG ACC CTG AAG TTC ATC TGC ACC ACC GGC AAG CTG
--- --- --- --- --- --- --- --- --- --- --- --- --- --- --- --- --- ---
Asp Ala Thr Tyr Gly Lys Leu Thr Leu Lys Phe Ile Cys Thr Thr Gly Lys Leu 171         180         189         198         207         216
CCC GTG CCC TGG CCC ACC CTC GTG ACC ACC TTC GGC TAC GGC GTG CAG TGC TTC
--- --- --- --- --- --- --- --- --- --- --- --- --- --- --- --- --- ---
Pro Val Pro Trp Pro Thr Leu Val Thr Thr Phe Gly Tyr Gly Val Gln Cys Phe 225         234         243         252         261         270
GCC CGC TAC CCC GAC CAC ATG AAG CAG CAC GAC TTC TTC AAG TCC GCC ATG CCC
--- --- --- --- --- --- --- --- --- --- --- --- --- --- --- --- --- ---
Ala Arg Tyr Pro Asp His Met Lys Gln His Asp Phe Phe Lys Ser Ala Met Pro 279         288         297         306         315         324
GAA GGC TAC GTC CAG GAG CGC ACC ATC TTC TTC AAG GAC GAC GGC AAC TAC AAG
--- --- --- --- --- --- --- --- --- --- --- --- --- --- --- --- --- ---
Glu Gly Tyr Val Gln Glu Arg Thr Ile Phe Phe Lys Asp Asp Gly Asn Tyr Lys 333         342         351         360         369         378
ACC CGC GCC GAG GTG AAG TTC GAG GGC GAC ACC CTG GTG AAC CGC ATC GAG CTG
--- --- --- --- --- --- --- --- --- --- --- --- --- --- --- --- --- ---
Thr Arg Ala Glu Val Lys Phe Glu Gly Asp Thr Leu Val Asn Arg Ile Glu Leu 387         396         405         414         423         432
AAG GGC ATC GAC TTC AAG GAG GAC GGC AAC ATC CTG GGG CAC AAG CTG GAG TAC
--- --- --- --- --- --- --- --- --- --- --- --- --- --- --- --- --- ---
Lys Gly Ile Asp Phe Lys Glu Asp Gly Asn Ile Leu Gly His Lys Leu Glu Tyr 441         450         459         468         477         486
AAC TAC AAC AGC CAC AAC GTC TAT ATC ATG GCC GAC AAG CAG AAG AAC GGC ATC
--- --- --- --- --- --- --- --- --- --- --- --- --- --- --- --- --- ---
Asn Tyr Asn Ser His Asn Val Tyr Ile Met Ala Asp Lys Gln Lys Asn Gly Ile
```

FIG. 4A

```
            495         504         513         522         531         540
AAG GTG AAC TTC AAG ATC CGC CAC AAC ATC GAG GAC GGC AGC GTG CAG CTC GCC
--- --- --- --- --- --- --- --- --- --- --- --- --- --- --- --- --- ---
Lys Val Asn Phe Lys Ile Arg His Asn Ile Glu Asp Gly Ser Val Gln Leu Ala 549         558         567         576         585         594
GAC CAC TAC CAG CAG AAC ACC CCC ATC GGC GAC GGC CCC GTG CTG CTG CCC GAC
--- --- --- --- --- --- --- --- --- --- --- --- --- --- --- --- --- ---
Asp His Tyr Gln Gln Asn Thr Pro Ile Gly Asp Gly Pro Val Leu Leu Pro Asp 603         612         621         630         639         648
AAC CAC TAC CTG AGC TAC CAG TCC GCC CTG AGC AAA GAC CCC AAC GAG AAG CGC
--- --- --- --- --- --- --- --- --- --- --- --- --- --- --- --- --- ---
Asn His Tyr Leu Ser Tyr Gln Ser Ala Leu Ser Lys Asp Pro Asn Glu Lys Arg 657         666         675         684         693         702
GAT CAC ATG GTC CTG CTG GAG TTC GTG ACC GCC GCC GGG ATC ACT CAC GGC ATG
--- --- --- --- --- --- --- --- --- --- --- --- --- --- --- --- --- ---
Asp His Met Val Leu Leu Glu Phe Val Thr Ala Ala Gly Ile Thr His Gly Met

711
GAC GAG CTG TAC AAG TAA 3'
--- --- --- --- --- ---
Asp Glu Leu Tyr Lys ***
```

FIG. 4B

| | | | | | | | | |
|---|---|---|---|---|---|---|---|---|
| CRYST1 | | 51.767 | 62.845 | 70.666 | 90.00 | 90.00 | 90.00 | |
| ORIGX1 | | 1.000000 | 0.000000 | 0.000000 | | 0.000000 | | |
| ORIGX2 | | 0.000000 | 1.000000 | 0.000000 | | 0.000000 | | |
| ORIGX3 | | 0.000000 | 0.000000 | 1.000000 | | 0.000000 | | |
| SCALE1 | | 0.019317 | 0.000000 | 0.000000 | | 0.000000 | | |
| SCALE2 | | 0.000000 | 0.015912 | 0.000000 | | 0.000000 | | |
| SCALE3 | | 0.000000 | 0.000000 | 0.014151 | | 0.000000 | | |
| ATOM | 1 | N | SER | 2 | 28.888 | 9.409 | 52.301 | 1.00 85.05 |
| ATOM | 2 | CA | SER | 2 | 27.638 | 10.125 | 52.516 | 1.00 80.05 |
| ATOM | 3 | C | SER | 2 | 26.499 | 9.639 | 51.644 | 1.00 85.36 |
| ATOM | 4 | O | SER | 2 | 26.606 | 8.656 | 50.915 | 1.00 84.56 |
| ATOM | 5 | CB | SER | 2 | 27.783 | 11.635 | 52.378 | 1.00 70.97 |
| ATOM | 6 | OG | SER | 2 | 27.690 | 12.033 | 51.012 | 1.00 44.08 |
| ATOM | 7 | N | LYS | 3 | 25.418 | 10.403 | 51.731 | 1.00 87.71 |
| ATOM | 8 | CA | LYS | 3 | 24.141 | 10.191 | 51.036 | 1.00 87.15 |
| ATOM | 9 | C | LYS | 3 | 24.214 | 10.266 | 49.497 | 1.00 76.86 |
| ATOM | 10 | O | LYS | 3 | 24.107 | 9.258 | 48.774 | 1.00 78.27 |
| ATOM | 11 | CB | LYS | 3 | 23.127 | 11.240 | 51.521 | 1.00 89.44 |
| ATOM | 12 | CG | LYS | 3 | 21.768 | 10.697 | 51.949 | 1.00 75.06 |
| ATOM | 13 | CD | LYS | 3 | 20.681 | 11.781 | 51.987 | 1.00 76.58 |
| ATOM | 14 | CE | LYS | 3 | 20.711 | 12.655 | 53.243 | 1.00 68.55 |
| ATOM | 15 | NZ | LYS | 3 | 20.816 | 14.103 | 52.953 | 1.00 46.24 |
| ATOM | 16 | N | GLY | 4 | 24.318 | 11.495 | 49.015 | 1.00 53.62 |
| ATOM | 17 | CA | GLY | 4 | 24.297 | 11.798 | 47.605 | 1.00 45.97 |
| ATOM | 18 | C | GLY | 4 | 25.425 | 11.206 | 46.796 | 1.00 31.90 |
| ATOM | 19 | O | GLY | 4 | 25.234 | 10.923 | 45.619 | 1.00 33.63 |
| ATOM | 20 | N | GLU | 5 | 26.606 | 11.082 | 47.420 | 1.00 32.54 |
| ATOM | 21 | CA | GLU | 5 | 27.821 | 10.598 | 46.726 | 1.00 32.57 |
| ATOM | 22 | C | GLU | 5 | 27.523 | 9.590 | 45.616 | 1.00 28.40 |
| ATOM | 23 | O | GLU | 5 | 27.850 | 9.803 | 44.444 | 1.00 26.12 |
| ATOM | 24 | CB | GLU | 5 | 28.873 | 10.053 | 47.718 | 1.00 38.53 |
| ATOM | 25 | CG | GLU | 5 | 30.337 | 10.461 | 47.425 | 1.00 41.36 |
| ATOM | 26 | CD | GLU | 5 | 31.311 | 9.584 | 48.170 | 1.00 90.82 |
| ATOM | 27 | OE1 | GLU | 5 | 31.508 | 9.677 | 49.381 | 1.00 74.80 |
| ATOM | 28 | OE2 | GLU | 5 | 31.839 | 8.653 | 47.403 | 1.00 100.00 |
| ATOM | 29 | N | GLU | 6 | 26.883 | 8.499 | 46.017 | 1.00 28.57 |
| ATOM | 30 | CA | GLU | 6 | 26.479 | 7.410 | 45.150 | 1.00 31.50 |
| ATOM | 31 | C | GLU | 6 | 25.561 | 7.837 | 43.979 | 1.00 31.10 |
| ATOM | 32 | O | GLU | 6 | 25.479 | 7.142 | 42.955 | 1.00 30.96 |
| ATOM | 33 | CB | GLU | 6 | 25.780 | 6.330 | 45.992 | 1.00 35.64 |
| ATOM | 34 | CG | GLU | 6 | 25.260 | 6.893 | 47.338 | 1.00 55.53 |
| ATOM | 35 | N | LEU | 7 | 24.864 | 8.966 | 44.138 | 1.00 22.26 |

*FIG. 5A*

| | | | | | | | | |
|---|---|---|---|---|---|---|---|---|
| ATOM | 36 | CA | LEU | 7 | 23.954 | 9.456 | 43.089 | 1.00 21.61 |
| ATOM | 37 | C | LEU | 7 | 24.693 | 10.061 | 41.917 | 1.00 16.90 |
| ATOM | 38 | O | LEU | 7 | 24.152 | 10.250 | 40.836 | 1.00 18.38 |
| ATOM | 39 | CB | LEU | 7 | 23.050 | 10.548 | 43.665 | 1.00 22.41 |
| ATOM | 40 | CG | LEU | 7 | 21.672 | 10.058 | 44.098 | 1.00 32.84 |
| ATOM | 41 | CD1 | LEU | 7 | 21.597 | 8.536 | 44.074 | 1.00 31.64 |
| ATOM | 42 | CD2 | LEU | 7 | 21.332 | 10.591 | 45.485 | 1.00 33.14 |
| ATOM | 43 | N | PHE | 8 | 25.944 | 10.407 | 42.157 | 1.00 20.75 |
| ATOM | 44 | CA | PHE | 8 | 26.740 | 11.132 | 41.159 | 1.00 21.64 |
| ATOM | 45 | C | PHE | 8 | 27.818 | 10.333 | 40.427 | 1.00 30.59 |
| ATOM | 46 | O | PHE | 8 | 28.590 | 10.856 | 39.600 | 1.00 30.05 |
| ATOM | 47 | CB | PHE | 8 | 27.309 | 12.376 | 41.820 | 1.00 16.95 |
| ATOM | 48 | CG | PHE | 8 | 26.222 | 13.355 | 42.163 | 1.00 13.29 |
| ATOM | 49 | CD1 | PHE | 8 | 25.672 | 13.378 | 43.447 | 1.00 17.27 |
| ATOM | 50 | CD2 | PHE | 8 | 25.726 | 14.227 | 41.189 | 1.00 13.12 |
| ATOM | 51 | CE1 | PHE | 8 | 24.661 | 14.290 | 43.772 | 1.00 15.14 |
| ATOM | 52 | CE2 | PHE | 8 | 24.712 | 15.137 | 41.499 | 1.00 13.19 |
| ATOM | 53 | CZ | PHE | 8 | 24.192 | 15.170 | 42.794 | 1.00 5.69 |
| ATOM | 54 | N | THR | 9 | 27.798 | 9.074 | 40.699 | 1.00 27.35 |
| ATOM | 55 | CA | THR | 9 | 28.704 | 8.122 | 40.175 | 1.00 34.93 |
| ATOM | 56 | C | THR | 9 | 28.709 | 7.998 | 38.636 | 1.00 45.22 |
| ATOM | 57 | O | THR | 9 | 29.642 | 7.452 | 38.062 | 1.00 50.55 |
| ATOM | 58 | CB | THR | 9 | 28.447 | 6.795 | 40.892 | 1.00 44.60 |
| ATOM | 59 | OG1 | THR | 9 | 29.629 | 6.330 | 41.527 | 1.00 40.40 |
| ATOM | 60 | CG2 | THR | 9 | 27.801 | 5.779 | 39.959 | 1.00 29.76 |
| ATOM | 61 | N | GLY | 10 | 27.690 | 8.510 | 37.956 | 1.00 30.53 |
| ATOM | 62 | CA | GLY | 10 | 27.689 | 8.458 | 36.507 | 1.00 23.21 |
| ATOM | 63 | C | GLY | 10 | 27.144 | 9.746 | 35.914 | 1.00 16.55 |
| ATOM | 64 | O | GLY | 10 | 27.011 | 10.729 | 36.617 | 1.00 25.70 |
| ATOM | 65 | N | VAL | 11 | 26.835 | 9.719 | 34.629 | 1.00 16.39 |
| ATOM | 66 | CA | VAL | 11 | 26.209 | 10.863 | 33.971 | 1.00 22.28 |
| ATOM | 67 | C | VAL | 11 | 24.758 | 11.020 | 34.479 | 1.00 29.60 |
| ATOM | 68 | O | VAL | 11 | 23.972 | 10.062 | 34.456 | 1.00 20.43 |
| ATOM | 69 | CB | VAL | 11 | 26.173 | 10.664 | 32.467 | 1.00 30.87 |
| ATOM | 70 | CG1 | VAL | 11 | 25.912 | 11.980 | 31.734 | 1.00 31.75 |
| ATOM | 71 | CG2 | VAL | 11 | 27.480 | 10.048 | 32.015 | 1.00 33.85 |
| ATOM | 72 | N | VAL | 12 | 24.417 | 12.227 | 34.931 | 1.00 20.12 |
| ATOM | 73 | CA | VAL | 12 | 23.080 | 12.561 | 35.433 | 1.00 12.88 |
| ATOM | 74 | C | VAL | 12 | 22.407 | 13.624 | 34.516 | 1.00 14.37 |
| ATOM | 75 | O | VAL | 12 | 23.007 | 14.639 | 34.179 | 1.00 13.42 |
| ATOM | 76 | CB | VAL | 12 | 23.270 | 13.077 | 36.839 | 1.00 15.01 |

*FIG. 5B*

| ATOM | 77 | CG1 VAL | 12 | 22.000 | 13.662 | 37.422 | 1.00 | 17.57 |
|---|---|---|---|---|---|---|---|---|
| ATOM | 78 | CG2 VAL | 12 | 23.781 | 11.936 | 37.728 | 1.00 | 16.55 |
| ATOM | 79 | N PRO | 13 | 21.180 | 13.382 | 34.066 | 1.00 | 14.72 |
| ATOM | 80 | CA PRO | 13 | 20.493 | 14.382 | 33.265 | 1.00 | 10.76 |
| ATOM | 81 | C PRO | 13 | 20.116 | 15.589 | 34.141 | 1.00 | 7.65 |
| ATOM | 82 | O PRO | 13 | 19.797 | 15.468 | 35.337 | 1.00 | 15.14 |
| ATOM | 83 | CB PRO | 13 | 19.225 | 13.707 | 32.745 | 1.00 | 17.36 |
| ATOM | 84 | CG PRO | 13 | 19.043 | 12.422 | 33.550 | 1.00 | 19.69 |
| ATOM | 85 | CD PRO | 13 | 20.315 | 12.195 | 34.340 | 1.00 | 15.41 |
| ATOM | 86 | N ILE | 14 | 20.196 | 16.766 | 33.557 | 1.00 | 14.91 |
| ATOM | 87 | CA ILE | 14 | 19.893 | 17.991 | 34.266 | 1.00 | 12.93 |
| ATOM | 88 | C ILE | 14 | 18.768 | 18.760 | 33.596 | 1.00 | 12.08 |
| ATOM | 89 | O ILE | 14 | 18.724 | 18.878 | 32.399 | 1.00 | 11.04 |
| ATOM | 90 | CB ILE | 14 | 21.109 | 18.905 | 34.325 | 1.00 | 16.54 |
| ATOM | 91 | CG1 ILE | 14 | 22.271 | 18.169 | 35.015 | 1.00 | 18.08 |
| ATOM | 92 | CG2 ILE | 14 | 20.783 | 20.207 | 35.084 | 1.00 | 11.56 |
| ATOM | 93 | CD1 ILE | 14 | 23.642 | 18.836 | 34.738 | 1.00 | 16.15 |
| ATOM | 94 | N LEU | 15 | 17.899 | 19.307 | 34.421 | 1.00 | 13.85 |
| ATOM | 95 | CA LEU | 15 | 16.811 | 20.136 | 33.955 | 1.00 | 14.82 |
| ATOM | 96 | C LEU | 15 | 16.915 | 21.474 | 34.685 | 1.00 | 3.62 |
| ATOM | 97 | O LEU | 15 | 17.080 | 21.509 | 35.901 | 1.00 | 10.00 |
| ATOM | 98 | CB LEU | 15 | 15.462 | 19.450 | 34.285 | 1.00 | 21.25 |
| ATOM | 99 | CG LEU | 15 | 14.412 | 19.541 | 33.199 | 1.00 | 40.50 |
| ATOM | 100 | CD1 LEU | 15 | 13.279 | 20.440 | 33.679 | 1.00 | 46.97 |
| ATOM | 101 | CD2 LEU | 15 | 15.008 | 20.098 | 31.913 | 1.00 | 49.22 |
| ATOM | 102 | N VAL | 16 | 16.885 | 22.556 | 33.919 | 1.00 | 10.56 |
| ATOM | 103 | CA VAL | 16 | 16.964 | 23.905 | 34.479 | 1.00 | 10.23 |
| ATOM | 104 | C VAL | 16 | 15.716 | 24.727 | 34.063 | 1.00 | 9.47 |
| ATOM | 105 | O VAL | 16 | 15.347 | 24.748 | 32.904 | 1.00 | 16.72 |
| ATOM | 106 | CB VAL | 16 | 18.273 | 24.668 | 34.098 | 1.00 | 12.85 |
| ATOM | 107 | CG1 VAL | 16 | 18.226 | 26.075 | 34.691 | 1.00 | 12.58 |
| ATOM | 108 | CG2 VAL | 16 | 19.520 | 23.945 | 34.628 | 1.00 | 14.24 |
| ATOM | 109 | N GLU | 17 | 15.059 | 25.317 | 35.060 | 1.00 | 14.43 |
| ATOM | 110 | CA GLU | 17 | 13.904 | 26.144 | 34.870 | 1.00 | 13.61 |
| ATOM | 111 | C GLU | 17 | 14.086 | 27.474 | 35.571 | 1.00 | 9.38 |
| ATOM | 112 | O GLU | 17 | 14.331 | 27.524 | 36.765 | 1.00 | 15.74 |
| ATOM | 113 | CB GLU | 17 | 12.650 | 25.402 | 35.344 | 1.00 | 14.15 |
| ATOM | 114 | CG GLU | 17 | 12.436 | 24.178 | 34.447 | 1.00 | 15.37 |
| ATOM | 115 | CD GLU | 17 | 11.865 | 24.573 | 33.105 | 1.00 | 49.50 |
| ATOM | 116 | OE1 GLU | 17 | 11.160 | 25.557 | 32.950 | 1.00 | 83.46 |
| ATOM | 117 | OE2 GLU | 17 | 12.220 | 23.766 | 32.127 | 1.00 | 38.75 |

*FIG. 5C*

| | | | | | | | | |
|---|---|---|---|---|---|---|---|---|
| ATOM | 118 | N | LEU | 18 | 13.990 | 28.571 | 34.805 | 1.00 17.82 |
| ATOM | 119 | CA | LEU | 18 | 14.116 | 29.914 | 35.401 | 1.00 16.61 |
| ATOM | 120 | C | LEU | 18 | 12.962 | 30.855 | 35.057 | 1.00 14.91 |
| ATOM | 121 | O | LEU | 18 | 12.585 | 30.978 | 33.917 | 1.00 14.31 |
| ATOM | 122 | CB | LEU | 18 | 15.426 | 30.630 | 35.005 | 1.00 13.56 |
| ATOM | 123 | CG | LEU | 18 | 15.533 | 32.049 | 35.579 | 1.00 19.27 |
| ATOM | 124 | CD1 | LEU | 18 | 16.740 | 32.182 | 36.489 | 1.00 21.40 |
| ATOM | 125 | CD2 | LEU | 18 | 15.682 | 33.033 | 34.438 | 1.00 18.38 |
| ATOM | 126 | N | ASP | 19 | 12.480 | 31.551 | 36.082 | 1.00 17.88 |
| ATOM | 127 | CA | ASP | 19 | 11.476 | 32.577 | 35.940 | 1.00 19.57 |
| ATOM | 128 | C | ASP | 19 | 12.098 | 33.896 | 36.360 | 1.00 11.65 |
| ATOM | 129 | O | ASP | 19 | 12.486 | 34.044 | 37.493 | 1.00 16.82 |
| ATOM | 130 | CB | ASP | 19 | 10.234 | 32.305 | 36.847 | 1.00 24.92 |
| ATOM | 131 | CG | ASP | 19 | 9.305 | 31.262 | 36.282 | 1.00 38.46 |
| ATOM | 132 | OD1 | ASP | 19 | 8.572 | 30.587 | 36.989 | 1.00 61.49 |
| ATOM | 133 | OD2 | ASP | 19 | 9.337 | 31.189 | 34.949 | 1.00 22.44 |
| ATOM | 134 | N | GLY | 20 | 12.178 | 34.863 | 35.471 | 1.00 16.82 |
| ATOM | 135 | CA | GLY | 20 | 12.784 | 36.101 | 35.908 | 1.00 19.52 |
| ATOM | 136 | C | GLY | 20 | 12.048 | 37.385 | 35.538 | 1.00 19.35 |
| ATOM | 137 | O | GLY | 20 | 11.240 | 37.443 | 34.628 | 1.00 18.22 |
| ATOM | 138 | N | ASP | 21 | 12.401 | 38.407 | 36.286 | 1.00 13.19 |
| ATOM | 139 | CA | ASP | 21 | 11.908 | 39.737 | 36.112 | 1.00 16.36 |
| ATOM | 140 | C | ASP | 21 | 13.039 | 40.683 | 36.424 | 1.00 12.77 |
| ATOM | 141 | O | ASP | 21 | 13.517 | 40.742 | 37.569 | 1.00 15.18 |
| ATOM | 142 | CB | ASP | 21 | 10.701 | 40.036 | 37.040 | 1.00 22.26 |
| ATOM | 143 | CG | ASP | 21 | 10.230 | 41.491 | 37.022 | 1.00 30.80 |
| ATOM | 144 | OD1 | ASP | 21 | 10.878 | 42.407 | 36.557 | 1.00 27.40 |
| ATOM | 145 | OD2 | ASP | 21 | 9.062 | 41.658 | 37.604 | 1.00 45.92 |
| ATOM | 146 | N | VAL | 22 | 13.464 | 41.393 | 35.397 | 1.00 19.66 |
| ATOM | 147 | CA | VAL | 22 | 14.524 | 42.388 | 35.542 | 1.00 25.10 |
| ATOM | 148 | C | VAL | 22 | 14.010 | 43.780 | 35.154 | 1.00 18.26 |
| ATOM | 149 | O | VAL | 22 | 13.769 | 44.062 | 33.955 | 1.00 15.10 |
| ATOM | 150 | CB | VAL | 22 | 15.803 | 42.012 | 34.750 | 1.00 26.57 |
| ATOM | 151 | CG1 | VAL | 22 | 16.861 | 43.127 | 34.896 | 1.00 24.27 |
| ATOM | 152 | CG2 | VAL | 22 | 16.365 | 40.710 | 35.297 | 1.00 22.98 |
| ATOM | 153 | N | ASN | 23 | 13.823 | 44.641 | 36.166 | 1.00 25.32 |
| ATOM | 154 | CA | ASN | 23 | 13.319 | 45.993 | 35.908 | 1.00 32.81 |
| ATOM | 155 | C | ASN | 23 | 11.987 | 45.958 | 35.142 | 1.00 32.77 |
| ATOM | 156 | O | ASN | 23 | 11.774 | 46.730 | 34.187 | 1.00 30.47 |
| ATOM | 157 | CB | ASN | 23 | 14.344 | 46.831 | 35.096 | 1.00 31.26 |
| ATOM | 158 | CG | ASN | 23 | 15.374 | 47.607 | 35.938 | 1.00 24.72 |

*FIG. 5D*

| ATOM | 159 | OD1 ASN | 23 | 15.795 | 47.183 | 37.024 | 1.00 27.22 |
|------|-----|---------|----|--------|--------|--------|------------|
| ATOM | 160 | ND2 ASN | 23 | 15.829 | 48.723 | 35.389 | 1.00 41.15 |
| ATOM | 161 | N   GLY | 24 | 11.118 | 45.024 | 35.519 | 1.00 24.95 |
| ATOM | 162 | CA  GLY | 24 | 9.831  | 44.919 | 34.848 | 1.00 23.22 |
| ATOM | 163 | C   GLY | 24 | 9.832  | 44.111 | 33.573 | 1.00 23.31 |
| ATOM | 164 | O   GLY | 24 | 8.780  | 43.868 | 33.024 | 1.00 28.37 |
| ATOM | 165 | N   HIS | 25 | 11.000 | 43.691 | 33.071 | 1.00 20.89 |
| ATOM | 166 | CA  HIS | 25 | 11.042 | 42.840 | 31.877 | 1.00 19.30 |
| ATOM | 167 | C   HIS | 25 | 10.981 | 41.373 | 32.316 | 1.00 27.26 |
| ATOM | 168 | O   HIS | 25 | 11.898 | 40.850 | 32.951 | 1.00 26.47 |
| ATOM | 169 | CB  HIS | 25 | 12.268 | 43.060 | 30.958 | 1.00 24.20 |
| ATOM | 170 | CG  HIS | 25 | 12.313 | 44.382 | 30.218 | 1.00 33.04 |
| ATOM | 171 | ND1 HIS | 25 | 12.917 | 45.514 | 30.758 | 1.00 37.58 |
| ATOM | 172 | CD2 HIS | 25 | 11.876 | 44.716 | 28.971 | 1.00 42.76 |
| ATOM | 173 | CE1 HIS | 25 | 12.801 | 46.497 | 29.867 | 1.00 39.14 |
| ATOM | 174 | NE2 HIS | 25 | 12.185 | 46.050 | 28.778 | 1.00 42.80 |
| ATOM | 175 | N   LYS | 26 | 9.872  | 40.728 | 32.028 | 1.00 25.90 |
| ATOM | 176 | CA  LYS | 26 | 9.675  | 39.355 | 32.446 | 1.00 26.27 |
| ATOM | 177 | C   LYS | 26 | 10.154 | 38.361 | 31.429 | 1.00 27.09 |
| ATOM | 178 | O   LYS | 26 | 10.027 | 38.576 | 30.232 | 1.00 25.75 |
| ATOM | 179 | CB  LYS | 26 | 8.230  | 39.069 | 32.863 | 1.00 27.58 |
| ATOM | 180 | CG  LYS | 26 | 7.873  | 39.770 | 34.166 | 1.00 44.94 |
| ATOM | 181 | CD  LYS | 26 | 6.369  | 39.914 | 34.400 | 1.00 71.44 |
| ATOM | 182 | CE  LYS | 26 | 6.008  | 41.000 | 35.421 | 1.00 45.29 |
| ATOM | 183 | N   PHE | 27 | 10.703 | 37.250 | 31.910 | 1.00 22.04 |
| ATOM | 184 | CA  PHE | 27 | 11.164 | 36.236 | 30.978 | 1.00 18.78 |
| ATOM | 185 | C   PHE | 27 | 11.273 | 34.863 | 31.619 | 1.00 14.75 |
| ATOM | 186 | O   PHE | 27 | 11.293 | 34.722 | 32.842 | 1.00 15.94 |
| ATOM | 187 | CB  PHE | 27 | 12.495 | 36.638 | 30.287 | 1.00 21.58 |
| ATOM | 188 | CG  PHE | 27 | 13.599 | 36.826 | 31.311 | 1.00 22.06 |
| ATOM | 189 | CD1 PHE | 27 | 14.490 | 35.791 | 31.612 | 1.00 23.61 |
| ATOM | 190 | CD2 PHE | 27 | 13.722 | 38.029 | 32.005 | 1.00 17.55 |
| ATOM | 191 | CE1 PHE | 27 | 15.487 | 35.963 | 32.579 | 1.00 16.61 |
| ATOM | 192 | CE2 PHE | 27 | 14.747 | 38.234 | 32.931 | 1.00 19.75 |
| ATOM | 193 | CZ  PHE | 27 | 15.621 | 37.187 | 33.234 | 1.00 13.83 |
| ATOM | 194 | N   SER | 28 | 11.370 | 33.857 | 30.752 | 1.00 12.40 |
| ATOM | 195 | CA  SER | 28 | 11.492 | 32.479 | 31.186 | 1.00 15.59 |
| ATOM | 196 | C   SER | 28 | 12.579 | 31.749 | 30.379 | 1.00 15.96 |
| ATOM | 197 | O   SER | 28 | 12.699 | 31.933 | 29.167 | 1.00 18.99 |
| ATOM | 198 | CB  SER | 28 | 10.143 | 31.702 | 31.086 | 1.00 14.48 |
| ATOM | 199 | OG  SER | 28 | 9.510  | 31.678 | 32.353 | 1.00 31.95 |

*FIG. 5E*

| | | | | | | | | |
|---|---|---|---|---|---|---|---|---|
| ATOM | 200 | N | VAL | 29 | 13.335 | 30.902 | 31.073 | 1.00 16.73 |
| ATOM | 201 | CA | VAL | 29 | 14.361 | 30.093 | 30.435 | 1.00 14.06 |
| ATOM | 202 | C | VAL | 29 | 14.258 | 28.614 | 30.187 | 1.00 6.80 |
| ATOM | 203 | O | VAL | 29 | 14.058 | 28.266 | 31.987 | 1.00 10.85 |
| ATOM | 204 | CB | VAL | 29 | 15.768 | 30.570 | 30.839 | 1.00 17.96 |
| ATOM | 205 | CG1 | VAL | 29 | 16.826 | 29.599 | 30.234 | 1.00 15.30 |
| ATOM | 206 | CG2 | VAL | 29 | 15.989 | 32.001 | 30.357 | 1.00 16.37 |
| ATOM | 207 | N | SER | 30 | 14.462 | 27.781 | 29.824 | 1.00 11.31 |
| ATOM | 208 | CA | SER | 30 | 14.535 | 26.351 | 30.011 | 1.00 17.96 |
| ATOM | 209 | C | SER | 30 | 15.917 | 25.818 | 29.571 | 1.00 11.26 |
| ATOM | 210 | O | SER | 30 | 16.398 | 26.157 | 28.513 | 1.00 13.17 |
| ATOM | 211 | CB | SER | 30 | 13.471 | 25.603 | 29.202 | 1.00 19.91 |
| ATOM | 212 | OG | SER | 30 | 12.249 | 25.667 | 29.882 | 1.00 48.74 |
| ATOM | 213 | N | GLY | 31 | 16.480 | 24.926 | 30.364 | 1.00 9.88 |
| ATOM | 214 | CA | GLY | 31 | 17.718 | 24.321 | 29.977 | 1.00 12.44 |
| ATOM | 215 | C | GLY | 31 | 17.737 | 22.816 | 30.249 | 1.00 13.16 |
| ATOM | 216 | O | GLY | 31 | 17.149 | 22.324 | 31.176 | 1.00 12.41 |
| ATOM | 217 | N | GLU | 32 | 18.459 | 22.112 | 29.433 | 1.00 13.44 |
| ATOM | 218 | CA | GLU | 32 | 18.622 | 20.670 | 29.570 | 1.00 13.73 |
| ATOM | 219 | C | GLU | 32 | 20.079 | 20.297 | 29.262 | 1.00 17.33 |
| ATOM | 220 | O | GLU | 32 | 20.734 | 20.946 | 28.456 | 1.00 15.56 |
| ATOM | 221 | CB | GLU | 32 | 17.761 | 19.893 | 28.543 | 1.00 12.67 |
| ATOM | 222 | CG | GLU | 32 | 16.264 | 20.187 | 28.618 | 1.00 26.43 |
| ATOM | 223 | CD | GLU | 32 | 15.501 | 19.547 | 27.468 | 1.00 21.13 |
| ATOM | 224 | OE1 | GLU | 32 | 15.996 | 18.767 | 26.698 | 1.00 23.45 |
| ATOM | 225 | OE2 | GLU | 32 | 14.292 | 20.022 | 27.337 | 1.00 30.63 |
| ATOM | 226 | N | GLY | 33 | 20.534 | 19.207 | 29.822 | 1.00 15.36 |
| ATOM | 227 | CA | GLY | 33 | 21.860 | 18.687 | 29.518 | 1.00 12.84 |
| ATOM | 228 | C | GLY | 33 | 22.236 | 17.602 | 30.467 | 1.00 14.69 |
| ATOM | 229 | O | GLY | 33 | 21.390 | 16.919 | 31.011 | 1.00 13.56 |
| ATOM | 230 | N | GLU | 34 | 23.525 | 17.453 | 30.702 | 1.00 15.15 |
| ATOM | 231 | CA | GLU | 34 | 23.971 | 16.450 | 31.621 | 1.00 18.14 |
| ATOM | 232 | C | GLU | 34 | 25.220 | 16.874 | 32.367 | 1.00 16.26 |
| ATOM | 233 | O | GLU | 34 | 25.926 | 17.760 | 31.944 | 1.00 18.67 |
| ATOM | 234 | CB | GLU | 34 | 24.180 | 15.114 | 30.927 | 1.00 22.53 |
| ATOM | 235 | CG | GLU | 34 | 24.948 | 15.261 | 29.624 | 1.00 33.78 |
| ATOM | 236 | CD | GLU | 34 | 24.879 | 14.020 | 28.796 | 1.00 55.15 |
| ATOM | 237 | OE1 | GLU | 34 | 25.861 | 13.352 | 28.534 | 1.00 45.39 |
| ATOM | 238 | OE2 | GLU | 34 | 23.653 | 13.719 | 28.430 | 1.00 56.26 |
| ATOM | 239 | N | GLY | 35 | 25.461 | 16.222 | 33.485 | 1.00 11.20 |
| ATOM | 240 | CA | GLY | 35 | 26.611 | 16.502 | 34.315 | 1.00 10.62 |

*FIG. 5F*

| | | | | | | | | |
|---|---|---|---|---|---|---|---|---|
| ATOM | 241 | C | GLY | 35 | 27.293 | 15.192 | 34.662 | 1.00 19.92 |
| ATOM | 242 | O | GLY | 35 | 26.650 | 14.161 | 34.750 | 1.00 16.69 |
| ATOM | 243 | N | ASP | 36 | 28.594 | 15.238 | 34.860 | 1.00 16.92 |
| ATOM | 244 | CA | ASP | 36 | 29.367 | 14.061 | 35.221 | 1.00 16.19 |
| ATOM | 245 | C | ASP | 36 | 30.396 | 14.505 | 36.233 | 1.00 13.94 |
| ATOM | 246 | O | ASP | 36 | 31.469 | 15.004 | 35.879 | 1.00 15.77 |
| ATOM | 247 | CB | ASP | 36 | 30.032 | 13.457 | 33.948 | 1.00 19.98 |
| ATOM | 248 | CG | ASP | 36 | 30.681 | 12.066 | 34.075 | 1.00 31.92 |
| ATOM | 249 | OD1 | ASP | 36 | 31.236 | 11.519 | 33.141 | 1.00 30.97 |
| ATOM | 250 | OD2 | ASP | 36 | 30.587 | 11.515 | 35.248 | 1.00 25.32 |
| ATOM | 251 | N | ALA | 37 | 30.015 | 14.402 | 37.490 | 1.00 13.40 |
| ATOM | 252 | CA | ALA | 37 | 30.818 | 14.846 | 38.582 | 1.00 12.98 |
| ATOM | 253 | C | ALA | 37 | 32.181 | 14.145 | 38.637 | 1.00 21.94 |
| ATOM | 254 | O | ALA | 37 | 33.084 | 14.604 | 39.331 | 1.00 13.61 |
| ATOM | 255 | CB | ALA | 37 | 30.070 | 14.741 | 39.916 | 1.00 11.49 |
| ATOM | 256 | N | THR | 38 | 32.307 | 13.016 | 37.945 | 1.00 15.63 |
| ATOM | 257 | CA | THR | 38 | 33.581 | 12.280 | 37.943 | 1.00 19.94 |
| ATOM | 258 | C | THR | 38 | 34.705 | 13.114 | 37.335 | 1.00 25.61 |
| ATOM | 259 | O | THR | 38 | 35.850 | 13.069 | 37.775 | 1.00 17.89 |
| ATOM | 260 | CB | THR | 38 | 33.462 | 10.898 | 37.299 | 1.00 22.57 |
| ATOM | 261 | OG1 | THR | 38 | 32.543 | 10.146 | 38.067 | 1.00 29.86 |
| ATOM | 262 | CG2 | THR | 38 | 34.821 | 10.213 | 37.355 | 1.00 22.90 |
| ATOM | 263 | N | TYR | 39 | 34.323 | 13.920 | 36.347 | 1.00 18.45 |
| ATOM | 264 | CA | TYR | 39 | 35.210 | 14.837 | 35.675 | 1.00 9.39 |
| ATOM | 265 | C | TYR | 39 | 34.874 | 16.291 | 35.991 | 1.00 14.41 |
| ATOM | 266 | O | TYR | 39 | 35.454 | 17.177 | 35.410 | 1.00 16.24 |
| ATOM | 267 | CB | TYR | 39 | 35.156 | 14.582 | 34.180 | 1.00 11.82 |
| ATOM | 268 | CG | TYR | 39 | 35.426 | 13.137 | 33.929 | 1.00 28.73 |
| ATOM | 269 | CD1 | TYR | 39 | 36.715 | 12.633 | 34.065 | 1.00 33.75 |
| ATOM | 270 | CD2 | TYR | 39 | 34.392 | 12.249 | 33.642 | 1.00 39.19 |
| ATOM | 271 | CE1 | TYR | 39 | 36.982 | 11.276 | 33.828 | 1.00 29.75 |
| ATOM | 272 | CE2 | TYR | 39 | 34.635 | 10.885 | 33.435 | 1.00 45.41 |
| ATOM | 273 | CZ | TYR | 39 | 35.943 | 10.410 | 33.570 | 1.00 57.62 |
| ATOM | 274 | OH | TYR | 39 | 36.199 | 9.070 | 33.364 | 1.00 70.77 |
| ATOM | 275 | N | GLY | 40 | 33.935 | 16.525 | 36.929 | 1.00 9.94 |
| ATOM | 276 | CA | GLY | 40 | 33.474 | 17.879 | 37.266 | 1.00 7.02 |
| ATOM | 277 | C | GLY | 40 | 32.952 | 18.600 | 36.004 | 1.00 9.45 |
| ATOM | 278 | O | GLY | 40 | 33.068 | 19.830 | 35.829 | 1.00 12.63 |
| ATOM | 279 | N | LYS | 41 | 32.380 | 17.823 | 35.092 | 1.00 5.44 |
| ATOM | 280 | CA | LYS | 41 | 31.954 | 18.335 | 33.842 | 1.00 6.63 |
| ATOM | 281 | C | LYS | 41 | 30.414 | 18.554 | 33.703 | 1.00 20.92 |

*FIG. 5G*

| ATOM | 282 | O   | LYS | 41 | 29.617 | 17.693 | 34.085 | 1.00 | 12.94 |
|------|-----|-----|-----|----|--------|--------|--------|------|-------|
| ATOM | 283 | CB  | LYS | 41 | 32.360 | 17.357 | 32.827 | 1.00 | 8.27  |
| ATOM | 284 | CG  | LYS | 41 | 32.099 | 17.771 | 31.419 | 1.00 | 13.19 |
| ATOM | 285 | CD  | LYS | 41 | 32.521 | 16.644 | 30.481 | 1.00 | 20.20 |
| ATOM | 286 | CE  | LYS | 41 | 32.690 | 17.068 | 29.032 | 1.00 | 35.79 |
| ATOM | 287 | NZ  | LYS | 41 | 33.113 | 15.954 | 28.147 | 1.00 | 47.56 |
| ATOM | 288 | N   | LEU | 42 | 30.049 | 19.684 | 33.069 | 1.00 | 18.31 |
| ATOM | 289 | CA  | LEU | 42 | 28.643 | 20.064 | 32.794 | 1.00 | 16.08 |
| ATOM | 290 | C   | LEU | 42 | 28.456 | 20.422 | 31.330 | 1.00 | 14.23 |
| ATOM | 291 | O   | LEU | 42 | 29.240 | 21.168 | 30.787 | 1.00 | 14.79 |
| ATOM | 292 | CB  | LEU | 42 | 28.223 | 21.300 | 33.621 | 1.00 | 13.22 |
| ATOM | 293 | CG  | LEU | 42 | 28.007 | 21.061 | 35.082 | 1.00 | 16.70 |
| ATOM | 294 | CD1 | LEU | 42 | 27.894 | 22.406 | 35.782 | 1.00 | 13.79 |
| ATOM | 295 | CD2 | LEU | 42 | 26.732 | 20.243 | 35.295 | 1.00 | 18.70 |
| ATOM | 296 | N   | THR | 43 | 27.395 | 19.914 | 30.672 | 1.00 | 8.04  |
| ATOM | 297 | CA  | THR | 43 | 27.103 | 20.275 | 29.282 | 1.00 | 4.87  |
| ATOM | 298 | C   | THR | 43 | 25.636 | 20.666 | 29.186 | 1.00 | 17.23 |
| ATOM | 299 | O   | THR | 43 | 24.811 | 19.818 | 29.442 | 1.00 | 14.38 |
| ATOM | 300 | CB  | THR | 43 | 27.351 | 19.140 | 28.317 | 1.00 | 21.59 |
| ATOM | 301 | OG1 | THR | 43 | 28.692 | 18.743 | 28.415 | 1.00 | 42.74 |
| ATOM | 302 | CG2 | THR | 43 | 27.073 | 19.675 | 26.917 | 1.00 | 31.23 |
| ATOM | 303 | N   | LEU | 44 | 25.327 | 21.934 | 28.830 | 1.00 | 11.83 |
| ATOM | 304 | CA  | LEU | 44 | 23.944 | 22.409 | 28.847 | 1.00 | 13.81 |
| ATOM | 305 | C   | LEU | 44 | 23.589 | 23.307 | 27.668 | 1.00 | 18.19 |
| ATOM | 306 | O   | LEU | 44 | 24.416 | 23.989 | 27.107 | 1.00 | 13.86 |
| ATOM | 307 | CB  | LEU | 44 | 23.725 | 23.275 | 30.125 | 1.00 | 15.37 |
| ATOM | 308 | CG  | LEU | 44 | 23.369 | 22.584 | 31.456 | 1.00 | 24.69 |
| ATOM | 309 | CD1 | LEU | 44 | 21.869 | 22.381 | 31.601 | 1.00 | 23.20 |
| ATOM | 310 | CD2 | LEU | 44 | 24.083 | 21.286 | 31.650 | 1.00 | 46.18 |
| ATOM | 311 | N   | LYS | 45 | 22.294 | 23.331 | 27.339 | 1.00 | 10.29 |
| ATOM | 312 | CA  | LYS | 45 | 21.752 | 24.224 | 26.358 | 1.00 | 11.94 |
| ATOM | 313 | C   | LYS | 45 | 20.534 | 24.913 | 26.957 | 1.00 | 19.35 |
| ATOM | 314 | O   | LYS | 45 | 19.665 | 24.248 | 27.530 | 1.00 | 18.43 |
| ATOM | 315 | CB  | LYS | 45 | 21.409 | 23.560 | 25.060 | 1.00 | 13.75 |
| ATOM | 316 | CG  | LYS | 45 | 20.878 | 24.556 | 24.045 | 1.00 | 8.83  |
| ATOM | 317 | CD  | LYS | 45 | 20.486 | 23.863 | 22.746 | 1.00 | 26.87 |
| ATOM | 318 | CE  | LYS | 45 | 19.574 | 24.688 | 21.842 | 1.00 | 16.58 |
| ATOM | 319 | NZ  | LYS | 45 | 19.318 | 24.024 | 20.555 | 1.00 | 18.33 |
| ATOM | 320 | N   | PHE | 46 | 20.535 | 26.236 | 26.910 | 1.00 | 12.34 |
| ATOM | 321 | CA  | PHE | 46 | 19.463 | 27.048 | 27.451 | 1.00 | 13.32 |
| ATOM | 322 | C   | PHE | 46 | 18.759 | 27.718 | 26.343 | 1.00 | 18.26 |

*FIG. 5H*

| ATOM | 323 | O   | PHE | 46 | 19.386 | 28.093 | 25.360 | 1.00 | 16.83 |
|------|-----|-----|-----|----|--------|--------|--------|------|-------|
| ATOM | 324 | CB  | PHE | 46 | 19.934 | 28.101 | 28.473 | 1.00 | 15.29 |
| ATOM | 325 | CG  | PHE | 46 | 20.773 | 27.495 | 29.552 | 1.00 | 13.81 |
| ATOM | 326 | CD1 | PHE | 46 | 22.132 | 27.268 | 29.337 | 1.00 | 17.06 |
| ATOM | 327 | CD2 | PHE | 46 | 20.209 | 27.121 | 30.774 | 1.00 | 8.24  |
| ATOM | 328 | CE1 | PHE | 46 | 22.924 | 26.693 | 30.331 | 1.00 | 15.95 |
| ATOM | 329 | CE2 | PHE | 46 | 20.979 | 26.524 | 31.767 | 1.00 | 11.90 |
| ATOM | 330 | CZ  | PHE | 46 | 22.340 | 26.309 | 31.540 | 1.00 | 8.84  |
| ATOM | 331 | N   | ILE | 47 | 17.440 | 27.845 | 26.498 | 1.00 | 13.24 |
| ATOM | 332 | CA  | ILE | 47 | 16.588 | 28.453 | 25.479 | 1.00 | 18.02 |
| ATOM | 333 | C   | ILE | 47 | 15.645 | 29.460 | 26.118 | 1.00 | 20.14 |
| ATOM | 334 | O   | ILE | 47 | 15.039 | 29.162 | 27.148 | 1.00 | 17.67 |
| ATOM | 335 | CB  | ILE | 47 | 15.737 | 27.386 | 24.801 | 1.00 | 22.67 |
| ATOM | 336 | CG1 | ILE | 47 | 16.585 | 26.271 | 24.291 | 1.00 | 20.66 |
| ATOM | 337 | CG2 | ILE | 47 | 15.024 | 28.002 | 23.641 | 1.00 | 33.79 |
| ATOM | 338 | CD1 | ILE | 47 | 16.639 | 26.293 | 22.805 | 1.00 | 23.69 |
| ATOM | 339 | N   | CYS | 48 | 15.564 | 30.653 | 25.561 | 1.00 | 14.68 |
| ATOM | 340 | CA  | CYS | 48 | 14.681 | 31.635 | 26.170 | 1.00 | 16.93 |
| ATOM | 341 | C   | CYS | 48 | 13.323 | 31.352 | 25.628 | 1.00 | 24.18 |
| ATOM | 342 | O   | CYS | 48 | 13.122 | 31.513 | 24.453 | 1.00 | 20.63 |
| ATOM | 343 | CB  | CYS | 48 | 15.063 | 33.116 | 25.885 | 1.00 | 16.85 |
| ATOM | 344 | SG  | CYS | 48 | 13.913 | 34.268 | 26.712 | 1.00 | 22.06 |
| ATOM | 345 | N   | THR | 49 | 12.424 | 30.871 | 26.484 | 1.00 | 27.31 |
| ATOM | 346 | CA  | THR | 49 | 11.101 | 30.458 | 26.042 | 1.00 | 32.18 |
| ATOM | 347 | C   | THR | 49 | 10.106 | 31.572 | 25.803 | 1.00 | 37.51 |
| ATOM | 348 | O   | THR | 49 | 9.150  | 31.407 | 25.061 | 1.00 | 35.71 |
| ATOM | 349 | CB  | THR | 49 | 10.537 | 29.417 | 26.972 | 1.00 | 23.66 |
| ATOM | 350 | OG1 | THR | 49 | 10.387 | 29.989 | 28.258 | 1.00 | 30.10 |
| ATOM | 351 | CG2 | THR | 49 | 11.512 | 28.226 | 27.022 | 1.00 | 29.98 |
| ATOM | 352 | N   | THR | 50 | 10.314 | 32.693 | 26.447 | 1.00 | 32.34 |
| ATOM | 353 | CA  | THR | 50 | 9.416  | 33.810 | 26.283 | 1.00 | 28.67 |
| ATOM | 354 | C   | THR | 50 | 9.836  | 34.711 | 25.126 | 1.00 | 37.98 |
| ATOM | 355 | O   | THR | 50 | 9.228  | 35.763 | 24.904 | 1.00 | 39.17 |
| ATOM | 356 | CB  | THR | 50 | 9.251  | 34.611 | 27.589 | 1.00 | 36.23 |
| ATOM | 357 | OG1 | THR | 50 | 10.512 | 34.980 | 28.118 | 1.00 | 35.37 |
| ATOM | 358 | CG2 | THR | 50 | 8.507  | 33.773 | 28.602 | 1.00 | 27.78 |
| ATOM | 359 | N   | GLY | 51 | 10.881 | 34.282 | 24.372 | 1.00 | 31.04 |
| ATOM | 360 | CA  | GLY | 51 | 11.394 | 35.059 | 23.239 | 1.00 | 32.42 |
| ATOM | 361 | C   | GLY | 51 | 12.865 | 35.542 | 23.427 | 1.00 | 48.45 |
| ATOM | 362 | O   | GLY | 51 | 13.779 | 34.737 | 23.701 | 1.00 | 57.11 |
| ATOM | 363 | N   | LYS | 52 | 13.087 | 36.862 | 23.282 | 1.00 | 36.08 |

*FIG. 5I*

| | | | | | | | |
|---|---|---|---|---|---|---|---|
| ATOM | 364 | CA | LYS | 52 | 14.416 | 37.460 | 23.416 | 1.00 35.75 |
| ATOM | 365 | C | LYS | 52 | 14.827 | 37.726 | 24.861 | 1.00 29.65 |
| ATOM | 366 | O | LYS | 52 | 14.140 | 38.420 | 25.620 | 1.00 25.70 |
| ATOM | 367 | CB | LYS | 52 | 14.577 | 38.714 | 22.582 | 1.00 43.37 |
| ATOM | 368 | CG | LYS | 52 | 15.772 | 38.649 | 21.644 | 1.00 78.17 |
| ATOM | 369 | N | LEU | 53 | 15.983 | 37.190 | 25.250 | 1.00 19.22 |
| ATOM | 370 | CA | LEU | 53 | 16.439 | 37.430 | 26.596 | 1.00 13.52 |
| ATOM | 371 | C | LEU | 53 | 16.717 | 38.932 | 26.775 | 1.00 17.76 |
| ATOM | 372 | O | LEU | 53 | 17.392 | 39.539 | 25.973 | 1.00 21.59 |
| ATOM | 373 | CB | LEU | 53 | 17.705 | 36.567 | 26.845 | 1.00 17.39 |
| ATOM | 374 | CG | LEU | 53 | 18.100 | 36.435 | 28.302 | 1.00 17.43 |
| ATOM | 375 | CD1 | LEU | 53 | 17.048 | 35.621 | 29.053 | 1.00 20.12 |
| ATOM | 376 | CD2 | LEU | 53 | 19.440 | 35.718 | 28.368 | 1.00 16.11 |
| ATOM | 377 | N | PRO | 54 | 16.197 | 39.525 | 27.817 | 1.00 16.69 |
| ATOM | 378 | CA | PRO | 54 | 16.324 | 40.962 | 28.092 | 1.00 18.60 |
| ATOM | 379 | C | PRO | 54 | 17.638 | 41.414 | 28.707 | 1.00 25.39 |
| ATOM | 380 | O | PRO | 54 | 17.865 | 42.609 | 28.861 | 1.00 18.88 |
| ATOM | 381 | CB | PRO | 54 | 15.268 | 41.265 | 29.139 | 1.00 22.52 |
| ATOM | 382 | CG | PRO | 54 | 14.832 | 39.933 | 29.720 | 1.00 26.02 |
| ATOM | 383 | CD | PRO | 54 | 15.318 | 38.855 | 28.779 | 1.00 21.26 |
| ATOM | 384 | N | VAL | 55 | 18.435 | 40.455 | 29.161 | 1.00 23.32 |
| ATOM | 385 | CA | VAL | 55 | 19.746 | 40.716 | 29.711 | 1.00 15.83 |
| ATOM | 386 | C | VAL | 55 | 20.688 | 39.868 | 28.973 | 1.00 19.38 |
| ATOM | 387 | O | VAL | 55 | 20.268 | 39.035 | 28.219 | 1.00 20.34 |
| ATOM | 388 | CB | VAL | 55 | 19.814 | 40.409 | 31.147 | 1.00 17.67 |
| ATOM | 389 | CG1 | VAL | 55 | 18.864 | 41.340 | 31.851 | 1.00 22.52 |
| ATOM | 390 | CG2 | VAL | 55 | 19.402 | 38.959 | 31.397 | 1.00 19.11 |
| ATOM | 391 | N | PRO | 56 | 21.963 | 40.070 | 29.167 | 1.00 19.37 |
| ATOM | 392 | CA | PRO | 56 | 22.911 | 39.258 | 28.447 | 1.00 13.09 |
| ATOM | 393 | C | PRO | 56 | 23.059 | 37.834 | 29.038 | 1.00 5.83 |
| ATOM | 394 | O | PRO | 56 | 23.067 | 37.631 | 30.254 | 1.00 12.35 |
| ATOM | 395 | CB | PRO | 56 | 24.231 | 40.062 | 28.420 | 1.00 18.34 |
| ATOM | 396 | CG | PRO | 56 | 23.851 | 41.478 | 28.849 | 1.00 20.73 |
| ATOM | 397 | CD | PRO | 56 | 22.525 | 41.379 | 29.578 | 1.00 18.66 |
| ATOM | 398 | N | TRP | 57 | 23.202 | 36.848 | 28.158 | 1.00 11.12 |
| ATOM | 399 | CA | TRP | 57 | 23.354 | 35.458 | 28.595 | 1.00 12.55 |
| ATOM | 400 | C | TRP | 57 | 24.411 | 35.239 | 29.700 | 1.00 14.13 |
| ATOM | 401 | O | TRP | 57 | 24.178 | 34.586 | 30.709 | 1.00 11.49 |
| ATOM | 402 | CB | TRP | 57 | 23.604 | 34.535 | 27.406 | 1.00 10.56 |
| ATOM | 403 | CG | TRP | 57 | 22.335 | 34.237 | 26.641 | 1.00 12.65 |
| ATOM | 404 | CD1 | TRP | 57 | 21.999 | 34.714 | 25.426 | 1.00 16.24 |

*FIG. 5J*

| | | | | | | | |
|---|---|---|---|---|---|---|---|
| ATOM | 405 | CD2 TRP | 57 | 21.281 | 33.327 | 27.013 | 1.00 12.50 |
| ATOM | 406 | NE1 TRP | 57 | 20.784 | 34.200 | 25.018 | 1.00 14.25 |
| ATOM | 407 | CE2 TRP | 57 | 20.315 | 22.354 | 25.963 | 1.00 14.65 |
| ATOM | 408 | CE3 TRP | 57 | 21.052 | 32.521 | 28.129 | 1.00 12.01 |
| ATOM | 409 | CZ2 TRP | 57 | 19.148 | 32.583 | 26.007 | 1.00 14.36 |
| ATOM | 410 | CZ3 TRP | 57 | 19.887 | 31.767 | 28.170 | 1.00 14.23 |
| ATOM | 411 | CH2 TRP | 57 | 18.945 | 31.818 | 27.128 | 1.00 10.01 |
| ATOM | 412 | N   PRO | 58 | 25.594 | 35.800 | 29.518 | 1.00 15.78 |
| ATOM | 413 | CA  PRO | 58 | 26.629 | 35.616 | 30.503 | 1.00  9.53 |
| ATOM | 414 | C   PRO | 58 | 26.241 | 36.010 | 31.878 | 1.00  9.71 |
| ATOM | 415 | O   PRO | 58 | 26.760 | 35.467 | 32.825 | 1.00 11.70 |
| ATOM | 416 | CB  PRO | 58 | 27.833 | 36.441 | 30.040 | 1.00 10.83 |
| ATOM | 417 | CG  PRO | 58 | 27.597 | 36.748 | 28.582 | 1.00 18.50 |
| ATOM | 418 | CD  PRO | 58 | 26.137 | 36.432 | 28.278 | 1.00 15.82 |
| ATOM | 419 | N   THR | 59 | 25.336 | 36.977 | 32.021 | 1.00  7.54 |
| ATOM | 420 | CA  THR | 59 | 24.976 | 37.366 | 33.357 | 1.00  4.53 |
| ATOM | 421 | C   THR | 59 | 24.228 | 36.258 | 34.137 | 1.00  8.41 |
| ATOM | 422 | O   THR | 59 | 24.174 | 36.261 | 35.367 | 1.00 10.57 |
| ATOM | 423 | CB  THR | 59 | 24.187 | 38.691 | 33.384 | 1.00 16.64 |
| ATOM | 424 | OG1 THR | 59 | 22.895 | 38.480 | 32.844 | 1.00 15.51 |
| ATOM | 425 | CG2 THR | 59 | 24.917 | 39.731 | 32.542 | 1.00 15.76 |
| ATOM | 426 | N   LEU | 60 | 23.686 | 35.304 | 33.427 | 1.00 11.99 |
| ATOM | 427 | CA  LEU | 60 | 22.899 | 34.248 | 34.073 | 1.00  9.15 |
| ATOM | 428 | C   LEU | 60 | 23.657 | 32.944 | 34.385 | 1.00 15.62 |
| ATOM | 429 | O   LEU | 60 | 23.118 | 32.027 | 35.042 | 1.00 11.99 |
| ATOM | 430 | CB  LEU | 60 | 21.645 | 33.914 | 33.203 | 1.00  7.67 |
| ATOM | 431 | CG  LEU | 60 | 20.728 | 35.111 | 33.042 | 1.00 14.06 |
| ATOM | 432 | CD1 LEU | 60 | 19.620 | 34.775 | 32.062 | 1.00 14.54 |
| ATOM | 433 | CD2 LEU | 60 | 20.142 | 35.456 | 34.394 | 1.00 10.67 |
| ATOM | 434 | N   VAL | 61 | 24.893 | 32.837 | 33.917 | 1.00 11.27 |
| ATOM | 435 | CA  VAL | 61 | 25.656 | 31.587 | 34.094 | 1.00  4.37 |
| ATOM | 436 | C   VAL | 61 | 25.678 | 31.013 | 35.496 | 1.00  6.02 |
| ATOM | 437 | O   VAL | 61 | 25.385 | 29.805 | 35.743 | 1.00 10.75 |
| ATOM | 438 | CB  VAL | 61 | 27.050 | 31.643 | 33.406 | 1.00  7.14 |
| ATOM | 439 | CG1 VAL | 61 | 27.888 | 30.396 | 33.805 | 1.00  6.47 |
| ATOM | 440 | CG2 VAL | 61 | 26.890 | 31.745 | 31.876 | 1.00  6.63 |
| ATOM | 441 | N   THR | 62 | 26.053 | 31.843 | 36.442 | 1.00  7.02 |
| ATOM | 442 | CA  THR | 62 | 26.178 | 31.421 | 37.808 | 1.00  6.51 |
| ATOM | 443 | C   THR | 62 | 24.862 | 30.954 | 38.410 | 1.00  9.22 |
| ATOM | 444 | O   THR | 62 | 24.801 | 30.163 | 39.352 | 1.00  6.99 |
| ATOM | 445 | CB  THR | 62 | 26.816 | 32.520 | 38.660 | 1.00 16.97 |

*FIG. 5K*

| | | | | | | | |
|---|---|---|---|---|---|---|---|
| ATOM | 446 | OG1 THR | 62 | 26.103 | 33.744 | 38.453 | 1.00 12.00 |
| ATOM | 447 | CG2 THR | 62 | 28.297 | 32.708 | 39.225 | 1.00  8.86 |
| ATOM | 448 | N   THR | 63 | 23.814 | 31.547 | 37.910 | 1.00  9.98 |
| ATOM | 449 | CA  THR | 63 | 22.457 | 31.212 | 38.388 | 1.00  6.69 |
| ATOM | 450 | C   THR | 63 | 22.033 | 29.830 | 37.865 | 1.00  8.14 |
| ATOM | 451 | O   THR | 63 | 21.499 | 28.984 | 38.604 | 1.00 13.48 |
| ATOM | 452 | CB  THR | 63 | 21.458 | 32.312 | 37.295 | 1.00 11.14 |
| ATOM | 453 | OG1 THR | 63 | 21.785 | 33.498 | 38.602 | 1.00 11.75 |
| ATOM | 454 | OG2 THR | 63 | 20.024 | 31.897 | 38.296 | 1.00  9.31 |
| ATOM | 455 | N   PHE | 64 | 22.250 | 29.620 | 36.583 | 1.00 10.19 |
| ATOM | 456 | CA  PHE | 64 | 21.895 | 28.371 | 35.995 | 1.00  8.00 |
| ATOM | 457 | C   PHE | 64 | 22.774 | 27.253 | 36.518 | 1.00 25.26 |
| ATOM | 458 | O   PHE | 64 | 23.313 | 26.147 | 36.761 | 1.00  9.64 |
| ATOM | 459 | CB  PHE | 64 | 22.114 | 28.438 | 34.513 | 1.00  6.88 |
| ATOM | 460 | CG  PHE | 64 | 21.233 | 29.357 | 33.750 | 1.00 10.96 |
| ATOM | 461 | CD1 PHE | 64 | 21.724 | 29.954 | 32.593 | 1.00  9.15 |
| ATOM | 462 | CD2 PHE | 64 | 19.899 | 29.563 | 34.106 | 1.00 14.43 |
| ATOM | 463 | CE1 PHE | 64 | 20.936 | 30.792 | 31.805 | 1.00 14.20 |
| ATOM | 464 | CE2 PHE | 64 | 19.077 | 30.375 | 33.317 | 1.00 13.95 |
| ATOM | 465 | CZ  PHE | 64 | 19.597 | 30.983 | 32.171 | 1.00 16.35 |
| HETATM | 466 | N1  CRO | 66 | 24.077 | 27.513 | 36.610 | 1.00 11.86 |
| HETATM | 467 | CG1 CRO | 66 | 25.155 | 25.422 | 34.796 | 1.00 16.67 |
| HETATM | 468 | OG1 CRO | 66 | 26.679 | 27.129 | 35.461 | 1.00 14.22 |
| HETATM | 469 | CB1 CRO | 66 | 25.931 | 26.035 | 35.930 | 1.00 10.77 |
| HETATM | 470 | CA1 CRO | 66 | 25.011 | 26.478 | 37.078 | 1.00  7.34 |
| HETATM | 471 | C1  CRO | 66 | 25.718 | 26.991 | 38.253 | 1.00 17.70 |
| HETATM | 472 | N2  CRO | 66 | 26.975 | 27.732 | 38.216 | 1.00  9.21 |
| HETATM | 473 | OH  CRO | 66 | 32.894 | 30.804 | 36.971 | 1.00 13.84 |
| HETATM | 474 | CD2 CRO | 66 | 30.487 | 30.110 | 39.805 | 1.00 10.79 |
| HETATM | 475 | CE2 CRO | 66 | 31.614 | 30.563 | 39.085 | 1.00 10.01 |
| HETATM | 476 | CZ  CRO | 66 | 31.718 | 30.300 | 37.721 | 1.00  9.48 |
| HETATM | 477 | CE1 CRO | 66 | 30.707 | 29.546 | 37.033 | 1.00 17.44 |
| HETATM | 478 | CD1 CRO | 66 | 29.541 | 29.103 | 37.742 | 1.00 11.31 |
| HETATM | 479 | CG2 CRO | 66 | 29.437 | 29.370 | 39.124 | 1.00  7.67 |
| HETATM | 480 | CB2 CRO | 66 | 28.329 | 28.822 | 39.960 | 1.00 10.75 |
| HETATM | 481 | CA2 CRO | 66 | 27.197 | 28.245 | 39.512 | 1.00 16.08 |
| HETATM | 482 | C2  CRO | 66 | 26.043 | 27.875 | 40.370 | 1.00  5.46 |
| HETATM | 483 | O2  CRO | 66 | 26.022 | 27.962 | 41.566 | 1.00 13.20 |
| HETATM | 484 | N3  CRO | 66 | 25.240 | 26.978 | 39.517 | 1.00 18.43 |
| HETATM | 485 | CA3 CRO | 66 | 23.840 | 26.511 | 39.734 | 1.00 10.40 |
| HETATM | 486 | C3  CRO | 66 | 23.413 | 25.550 | 40.817 | 1.00 11.96 |

*FIG. 5L*

| | | | | | | | |
|---|---|---|---|---|---|---|---|
| HETATM | 487 | O3 CRO | 66 | 22.747 | 26.014 | 41.764 | 1.00 100.00 |
| ATOM | 488 | N VAL | 68 | 23.737 | 24.208 | 41.005 | 1.00 29.95 |
| ATOM | 489 | CA VAL | 68 | 24.209 | 22.972 | 40.304 | 1.00 17.16 |
| ATOM | 490 | C VAL | 68 | 25.692 | 22.550 | 40.734 | 1.00 14.88 |
| ATOM | 491 | O VAL | 68 | 26.378 | 21.821 | 40.026 | 1.00 9.03 |
| ATOM | 492 | CB VAL | 68 | 23.870 | 22.899 | 38.831 | 1.00 18.94 |
| ATOM | 493 | CG1 VAL | 68 | 24.685 | 22.088 | 37.942 | 1.00 17.17 |
| ATOM | 494 | CG2 VAL | 68 | 22.396 | 22.538 | 38.680 | 1.00 18.80 |
| ATOM | 495 | N GLN | 69 | 26.129 | 22.965 | 41.914 | 1.00 11.04 |
| ATOM | 496 | CA GLN | 69 | 27.465 | 22.764 | 42.394 | 1.00 15.00 |
| ATOM | 497 | C GLN | 69 | 27.749 | 21.366 | 42.893 | 1.00 22.46 |
| ATOM | 498 | O GLN | 69 | 28.876 | 21.026 | 43.154 | 1.00 15.84 |
| ATOM | 499 | CB GLN | 69 | 27.929 | 23.852 | 43.414 | 1.00 10.93 |
| ATOM | 500 | CG GLN | 69 | 28.202 | 25.174 | 42.615 | 1.00 14.13 |
| ATOM | 501 | CD GLN | 69 | 28.216 | 26.385 | 43.520 | 1.00 17.01 |
| ATOM | 502 | OE1 GLN | 69 | 27.433 | 26.476 | 44.448 | 1.00 18.94 |
| ATOM | 503 | NE2 GLN | 69 | 29.151 | 27.300 | 43.241 | 1.00 8.52 |
| ATOM | 504 | N CYS | 70 | 26.703 | 20.540 | 42.906 | 1.00 12.10 |
| ATOM | 505 | CA CYS | 70 | 26.862 | 19.171 | 43.287 | 1.00 11.84 |
| ATOM | 506 | C CYS | 70 | 27.611 | 18.391 | 42.175 | 1.00 10.54 |
| ATOM | 507 | O CYS | 70 | 28.036 | 17.242 | 42.367 | 1.00 14.70 |
| ATOM | 508 | CB CYS | 70 | 25.476 | 18.584 | 43.596 | 1.00 14.52 |
| ATOM | 509 | SG CYS | 70 | 24.325 | 19.012 | 42.251 | 1.00 15.61 |
| ATOM | 510 | N PHE | 71 | 27.801 | 19.029 | 41.005 | 1.00 8.64 |
| ATOM | 511 | CA PHE | 71 | 28.525 | 18.419 | 39.883 | 1.00 6.59 |
| ATOM | 512 | C PHE | 71 | 30.041 | 18.754 | 39.876 | 1.00 16.43 |
| ATOM | 513 | O PHE | 71 | 30.753 | 18.481 | 38.916 | 1.00 13.05 |
| ATOM | 514 | CB PHE | 71 | 27.951 | 18.771 | 38.523 | 1.00 7.61 |
| ATOM | 515 | CG PHE | 71 | 26.669 | 18.016 | 38.303 | 1.00 14.73 |
| ATOM | 516 | CD1 PHE | 71 | 26.693 | 16.642 | 38.050 | 1.00 10.34 |
| ATOM | 517 | CD2 PHE | 71 | 25.434 | 18.660 | 38.453 | 1.00 17.14 |
| ATOM | 518 | CE1 PHE | 71 | 25.506 | 15.931 | 37.866 | 1.00 15.09 |
| ATOM | 519 | CE2 PHE | 71 | 24.238 | 17.961 | 38.300 | 1.00 20.92 |
| ATOM | 520 | CZ PHE | 71 | 24.282 | 16.598 | 37.990 | 1.00 18.49 |
| ATOM | 521 | N SER | 72 | 30.500 | 19.370 | 40.938 | 1.00 13.13 |
| ATOM | 522 | CA SER | 72 | 31.889 | 19.715 | 41.075 | 1.00 11.65 |
| ATOM | 523 | C SER | 72 | 32.689 | 18.446 | 41.357 | 1.00 14.56 |
| ATOM | 524 | O SER | 72 | 32.256 | 17.566 | 42.122 | 1.00 10.90 |
| ATOM | 525 | CB SER | 72 | 32.075 | 20.672 | 42.257 | 1.00 8.65 |
| ATOM | 526 | OG SER | 72 | 31.361 | 21.874 | 42.038 | 1.00 19.29 |
| ATOM | 527 | N ARG | 73 | 33.905 | 18.358 | 40.794 | 1.00 16.27 |

*FIG. 5M*

| | | | | | | | |
|---|---|---|---|---|---|---|---|
| ATOM | 528 | CA | ARG | 73 | 34.695 | 17.212 | 41.117 | 1.00 13.56 |
| ATOM | 529 | C | ARG | 73 | 35.414 | 17.426 | 42.443 | 1.00 19.96 |
| ATOM | 530 | O | ARG | 73 | 36.182 | 18.376 | 42.599 | 1.00 16.14 |
| ATOM | 531 | CB | ARG | 73 | 35.694 | 16.817 | 40.013 | 1.00 16.80 |
| ATOM | 532 | CG | ARG | 73 | 36.549 | 15.616 | 40.460 | 1.00 20.13 |
| ATOM | 533 | CD | ARG | 73 | 37.489 | 15.093 | 39.381 | 1.00 28.47 |
| ATOM | 534 | NE | ARG | 73 | 38.743 | 15.859 | 39.260 | 1.00 25.48 |
| ATOM | 535 | CZ | ARG | 73 | 39.756 | 15.777 | 40.127 | 1.00 28.04 |
| ATOM | 536 | NH1 | ARG | 73 | 39.688 | 15.004 | 41.195 | 1.00 28.76 |
| ATOM | 537 | NH2 | ARG | 73 | 40.865 | 16.504 | 39.918 | 1.00 39.65 |
| ATOM | 538 | N | TYR | 74 | 35.151 | 16.561 | 43.424 | 1.00 12.05 |
| ATOM | 539 | CA | TYR | 74 | 35.861 | 16.659 | 44.690 | 1.00 11.57 |
| ATOM | 540 | C | TYR | 74 | 36.946 | 15.566 | 44.721 | 1.00 25.02 |
| ATOM | 541 | O | TYR | 74 | 36.658 | 14.387 | 44.558 | 1.00 19.71 |
| ATOM | 542 | CB | TYR | 74 | 34.978 | 16.528 | 45.934 | 1.00 15.51 |
| ATOM | 543 | CG | TYR | 74 | 34.395 | 17.850 | 46.402 | 1.00 16.59 |
| ATOM | 544 | CD1 | TYR | 74 | 33.455 | 18.546 | 45.631 | 1.00 14.44 |
| ATOM | 545 | CD2 | TYR | 74 | 34.799 | 18.399 | 47.618 | 1.00 15.94 |
| ATOM | 546 | CE1 | TYR | 74 | 32.901 | 19.756 | 46.059 | 1.00 7.99 |
| ATOM | 547 | CE2 | TYR | 74 | 34.261 | 19.612 | 48.058 | 1.00 18.29 |
| ATOM | 548 | CZ | TYR | 74 | 33.294 | 20.276 | 47.298 | 1.00 13.87 |
| ATOM | 549 | OH | TYR | 74 | 32.829 | 21.507 | 47.738 | 1.00 18.39 |
| ATOM | 550 | N | PRO | 75 | 38.181 | 15.947 | 44.902 | 1.00 19.20 |
| ATOM | 551 | CA | PRO | 75 | 39.213 | 14.940 | 44.995 | 1.00 18.42 |
| ATOM | 552 | C | PRO | 75 | 38.958 | 13.993 | 46.175 | 1.00 15.60 |
| ATOM | 553 | O | PRO | 75 | 39.373 | 14.361 | 47.174 | 1.00 11.99 |
| ATOM | 554 | CB | PRO | 75 | 40.514 | 15.681 | 45.196 | 1.00 18.31 |
| ATOM | 555 | CG | PRO | 75 | 40.242 | 17.158 | 44.868 | 1.00 24.81 |
| ATOM | 556 | CD | PRO | 75 | 38.742 | 17.306 | 44.694 | 1.00 15.41 |
| ATOM | 557 | N | ASP | 76 | 39.433 | 12.756 | 46.038 | 1.00 18.63 |
| ATOM | 558 | CA | ASP | 76 | 39.269 | 11.770 | 47.062 | 1.00 16.19 |
| ATOM | 559 | C | ASP | 76 | 39.581 | 12.280 | 48.431 | 1.00 15.92 |
| ATOM | 560 | O | ASP | 76 | 38.862 | 12.042 | 49.389 | 1.00 17.35 |
| ATOM | 561 | CB | ASP | 76 | 40.083 | 10.507 | 46.790 | 1.00 18.69 |
| ATOM | 562 | CG | ASP | 76 | 39.826 | 9.432 | 47.825 | 1.00 24.04 |
| ATOM | 563 | OD1 | ASP | 76 | 40.523 | 9.268 | 48.817 | 1.00 29.72 |
| ATOM | 564 | OD2 | ASP | 76 | 38.732 | 8.743 | 47.584 | 1.00 40.96 |
| ATOM | 565 | N | HIS | 77 | 40.647 | 12.984 | 48.561 | 1.00 18.79 |
| ATOM | 566 | CA | HIS | 77 | 40.978 | 13.418 | 49.877 | 1.00 19.36 |
| ATOM | 567 | C | HIS | 77 | 40.117 | 14.507 | 50.397 | 1.00 24.57 |
| ATOM | 568 | O | HIS | 77 | 40.205 | 14.826 | 51.551 | 1.00 27.15 |

*FIG. 5N*

| ATOM | 569 | CB | HIS | 77 | 42.435 | 13.806 | 50.042 | 1.00 | 19.84 |
| --- | --- | --- | --- | --- | --- | --- | --- | --- | --- |
| ATOM | 570 | CG | HIS | 77 | 42.743 | 15.035 | 49.322 | 1.00 | 17.31 |
| ATOM | 571 | ND1 | HIS | 77 | 42.925 | 15.028 | 47.953 | 1.00 | 21.86 |
| ATOM | 572 | CD2 | HIS | 77 | 42.925 | 16.295 | 49.774 | 1.00 | 18.70 |
| ATOM | 573 | CE1 | HIS | 77 | 43.203 | 16.289 | 47.593 | 1.00 | 17.49 |
| ATOM | 574 | NE2 | HIS | 77 | 43.213 | 17.069 | 48.668 | 1.00 | 18.11 |
| ATOM | 575 | N | MSE | 78 | 39.277 | 15.069 | 49.565 | 1.00 | 25.36 |
| ATOM | 576 | CA | MSE | 78 | 38.412 | 16.140 | 50.026 | 1.00 | 24.65 |
| ATOM | 577 | C | MSE | 78 | 36.920 | 15.774 | 50.066 | 1.00 | 26.47 |
| ATOM | 578 | O | MSE | 78 | 36.070 | 16.636 | 50.260 | 1.00 | 28.16 |
| ATOM | 579 | CB | MSE | 78 | 38.596 | 17.331 | 49.121 | 1.00 | 26.38 |
| ATOM | 580 | CG | MSE | 78 | 39.803 | 18.177 | 49.406 | 1.00 | 27.01 |
| ATOM | 581 | SE | MSE | 78 | 39.987 | 19.608 | 48.177 | 1.00 | 43.09 |
| ATOM | 582 | CE | MSE | 78 | 38.874 | 20.873 | 49.044 | 1.00 | 27.11 |
| ATOM | 583 | N | LYS | 79 | 36.606 | 14.509 | 49.856 | 1.00 | 18.68 |
| ATOM | 584 | CA | LYS | 79 | 35.216 | 14.061 | 49.853 | 1.00 | 21.54 |
| ATOM | 585 | C | LYS | 79 | 34.406 | 14.449 | 51.082 | 1.00 | 20.21 |
| ATOM | 586 | O | LYS | 79 | 33.186 | 14.652 | 51.025 | 1.00 | 21.08 |
| ATOM | 587 | CB | LYS | 79 | 35.152 | 12.581 | 49.612 | 1.00 | 23.48 |
| ATOM | 588 | CG | LYS | 79 | 35.859 | 12.225 | 48.317 | 1.00 | 41.09 |
| ATOM | 589 | CD | LYS | 79 | 35.159 | 11.134 | 47.535 | 1.00 | 34.66 |
| ATOM | 590 | CE | LYS | 79 | 35.796 | 10.881 | 46.181 | 1.00 | 53.46 |
| ATOM | 591 | NZ | LYS | 79 | 35.084 | 11.549 | 45.080 | 1.00 | 49.53 |
| ATOM | 592 | N | ARG | 80 | 35.069 | 14.542 | 52.213 | 1.00 | 19.77 |
| ATOM | 593 | CA | ARG | 80 | 34.365 | 14.874 | 53.434 | 1.00 | 20.13 |
| ATOM | 594 | C | ARG | 80 | 33.898 | 16.311 | 53.481 | 1.00 | 26.42 |
| ATOM | 595 | O | ARG | 80 | 33.251 | 16.717 | 54.467 | 1.00 | 23.51 |
| ATOM | 596 | CB | ARG | 80 | 35.155 | 14.549 | 54.700 | 1.00 | 24.58 |
| ATOM | 597 | CG | ARG | 80 | 36.204 | 15.620 | 55.034 | 1.00 | 29.71 |
| ATOM | 598 | CD | ARG | 80 | 36.964 | 15.344 | 56.335 | 1.00 | 61.30 |
| ATOM | 599 | NE | ARG | 80 | 36.551 | 16.230 | 57.415 | 1.00 | 71.14 |
| ATOM | 600 | CZ | ARG | 80 | 37.398 | 16.882 | 58.192 | 1.00 | 100.00 |
| ATOM | 601 | NH1 | ARG | 80 | 38.714 | 16.758 | 48.040 | 1.00 | 100.00 |
| ATOM | 602 | NH2 | ARG | 80 | 36.917 | 17.679 | 59.155 | 1.00 | 99.06 |
| ATOM | 603 | N | HIS | 81 | 34.275 | 17.121 | 52.473 | 1.00 | 18.77 |
| ATOM | 604 | CA | HIS | 81 | 33.903 | 18.547 | 52.499 | 1.00 | 19.60 |
| ATOM | 605 | C | HIS | 81 | 32.841 | 18.883 | 51.486 | 1.00 | 18.62 |
| ATOM | 606 | O | HIS | 81 | 32.557 | 20.043 | 51.295 | 1.00 | 17.76 |
| ATOM | 607 | CB | HIS | 81 | 35.129 | 19.472 | 52.283 | 1.00 | 20.39 |
| ATOM | 608 | CG | HIS | 81 | 36.221 | 19.224 | 53.305 | 1.00 | 28.02 |
| ATOM | 609 | ND1 | HIS | 81 | 36.127 | 19.701 | 54.618 | 1.00 | 30.59 |

*FIG. 50*

| ATOM | 610 | CD2 HIS | 81 | 37.392 | 18.535 | 53.202 | 1.00 | 29.02 |
|------|-----|---------|----|--------|--------|--------|------|-------|
| ATOM | 611 | CE1 HIS | 81 | 37.218 | 19.308 | 55.265 | 1.00 | 26.24 |
| ATOM | 612 | NE2 HIS | 81 | 37.991 | 18.603 | 54.452 | 1.00 | 28.18 |
| ATOM | 613 | N   ASP | 82 | 32.298 | 17.843 | 50.841 | 1.00 | 12.20 |
| ATOM | 614 | CA  ASP | 82 | 31.358 | 18.011 | 49.769 | 1.00 | 13.24 |
| ATOM | 615 | C   ASP | 82 | 29.922 | 18.148 | 50.259 | 1.00 | 24.30 |
| ATOM | 616 | O   ASP | 82 | 29.175 | 17.195 | 50.243 | 1.00 | 16.55 |
| ATOM | 617 | CB  ASP | 82 | 31.480 | 16.917 | 48.730 | 1.00 | 12.23 |
| ATOM | 618 | CG  ASP | 82 | 30.642 | 17.209 | 47.518 | 1.00 | 9.92  |
| ATOM | 619 | OD1 ASP | 82 | 29.870 | 18.134 | 47.459 | 1.00 | 20.31 |
| ATOM | 620 | OD2 ASP | 82 | 30.938 | 16.466 | 46.507 | 1.00 | 11.12 |
| ATOM | 621 | N   PHE | 83 | 29.566 | 19.353 | 50.705 | 1.00 | 23.66 |
| ATOM | 622 | CA  PHE | 83 | 28.220 | 19.634 | 51.201 | 1.00 | 20.23 |
| ATOM | 623 | C   PHE | 83 | 27.154 | 19.333 | 50.168 | 1.00 | 20.93 |
| ATOM | 624 | O   PHE | 83 | 26.116 | 18.733 | 50.503 | 1.00 | 15.97 |
| ATOM | 625 | CB  PHE | 83 | 28.077 | 21.106 | 51.666 | 1.00 | 19.59 |
| ATOM | 626 | CG  PHE | 83 | 26.624 | 21.613 | 51.805 | 1.00 | 16.91 |
| ATOM | 627 | CD1 PHE | 83 | 25.946 | 21.498 | 53.021 | 1.00 | 17.76 |
| ATOM | 628 | CD2 PHE | 83 | 25.968 | 22.236 | 50.734 | 1.00 | 18.88 |
| ATOM | 629 | CE1 PHE | 83 | 24.635 | 21.960 | 53.156 | 1.00 | 24.13 |
| ATOM | 630 | CE2 PHE | 83 | 24.650 | 22.690 | 50.840 | 1.00 | 19.24 |
| ATOM | 631 | CZ  PHE | 83 | 24.001 | 22.575 | 52.068 | 1.00 | 20.67 |
| ATOM | 632 | N   PHE | 84 | 27.432 | 19.784 | 48.921 | 1.00 | 14.06 |
| ATOM | 633 | CA  PHE | 84 | 26.515 | 19.693 | 47.809 | 1.00 | 12.96 |
| ATOM | 634 | C   PHE | 84 | 25.893 | 18.332 | 47.602 | 1.00 | 24.96 |
| ATOM | 635 | O   PHE | 84 | 24.674 | 18.200 | 47.534 | 1.00 | 21.55 |
| ATOM | 636 | CB  PHE | 84 | 27.085 | 20.265 | 46.513 | 1.00 | 13.44 |
| ATOM | 637 | CG  PHE | 84 | 27.630 | 21.645 | 46.721 | 1.00 | 14.27 |
| ATOM | 638 | CD1 PHE | 84 | 29.001 | 21.845 | 46.890 | 1.00 | 15.17 |
| ATOM | 639 | CD2 PHE | 84 | 26.781 | 22.753 | 46.752 | 1.00 | 13.48 |
| ATOM | 640 | CE1 PHE | 84 | 29.520 | 23.129 | 47.073 | 1.00 | 14.63 |
| ATOM | 641 | CE2 PHE | 84 | 27.276 | 24.041 | 46.969 | 1.00 | 16.34 |
| ATOM | 642 | CZ  PHE | 84 | 28.650 | 24.221 | 47.137 | 1.00 | 15.77 |
| ATOM | 643 | N   LYS | 85 | 26.738 | 17.330 | 47.482 | 1.00 | 14.07 |
| ATOM | 644 | CA  LYS | 85 | 26.294 | 15.985 | 47.283 | 1.00 | 13.30 |
| ATOM | 645 | C   LYS | 85 | 25.657 | 15.371 | 48.547 | 1.00 | 13.43 |
| ATOM | 646 | O   LYS | 85 | 24.773 | 14.509 | 48.429 | 1.00 | 18.46 |
| ATOM | 647 | CB  LYS | 85 | 27.434 | 15.089 | 46.757 | 1.00 | 17.38 |
| ATOM | 648 | CG  LYS | 85 | 27.873 | 15.372 | 45.323 | 1.00 | 13.93 |
| ATOM | 649 | CD  LYS | 85 | 28.969 | 14.381 | 44.888 | 1.00 | 13.23 |
| ATOM | 650 | CE  LYS | 85 | 29.766 | 14.819 | 43.662 | 1.00 | 10.36 |

*FIG. 5P*

| | | | | | | | | |
|---|---|---|---|---|---|---|---|---|
| ATOM | 651 | NZ | LYS | 85 | 30.319 | 16.185 | 43.773 | 1.00 12.92 |
| ATOM | 652 | N | SER | 86 | 26.119 | 15.795 | 49.752 | 1.00 11.03 |
| ATOM | 653 | CA | SER | 86 | 25.610 | 15.267 | 50.998 | 1.00 12.09 |
| ATOM | 654 | C | SER | 86 | 24.156 | 15.639 | 51.240 | 1.00 21.58 |
| ATOM | 655 | O | SER | 86 | 23.452 | 14.979 | 52.013 | 1.00 19.89 |
| ATOM | 656 | CB | SER | 86 | 26.448 | 15.661 | 52.208 | 1.00 16.45 |
| ATOM | 657 | OG | SER | 86 | 26.308 | 17.042 | 52.495 | 1.00 22.05 |
| ATOM | 658 | N | ALA | 87 | 23.705 | 16.698 | 50.582 | 1.00 15.09 |
| ATOM | 659 | CA | ALA | 87 | 22.333 | 17.138 | 50.762 | 1.00 19.52 |
| ATOM | 660 | C | ALA | 87 | 21.337 | 16.399 | 49.870 | 1.00 18.60 |
| ATOM | 661 | O | ALA | 87 | 20.162 | 16.557 | 50.040 | 1.00 19.55 |
| ATOM | 662 | CB | ALA | 87 | 22.204 | 18.647 | 50.632 | 1.00 19.23 |
| ATOM | 663 | N | MSE | 88 | 21.835 | 15.536 | 48.976 | 1.00 14.05 |
| ATOM | 664 | CA | MSE | 88 | 21.007 | 14.796 | 48.035 | 1.00 15.32 |
| ATOM | 665 | C | MSE | 88 | 20.496 | 13.448 | 48.579 | 1.00 21.48 |
| ATOM | 666 | O | MSE | 88 | 21.109 | 12.876 | 49.457 | 1.00 23.03 |
| ATOM | 667 | CB | MSE | 88 | 21.848 | 14.593 | 46.791 | 1.00 16.98 |
| ATOM | 668 | CG | MSE | 88 | 22.263 | 15.891 | 46.131 | 1.00 10.66 |
| ATOM | 669 | SE | MSE | 88 | 20.737 | 16.894 | 45.394 | 1.00 31.99 |
| ATOM | 670 | CE | MSE | 88 | 21.318 | 18.684 | 45.748 | 1.00 28.86 |
| ATOM | 671 | N | PRO | 89 | 19.363 | 12.930 | 48.084 | 1.00 14.78 |
| ATOM | 672 | CA | PRO | 89 | 18.552 | 13.475 | 47.008 | 1.00 14.80 |
| ATOM | 673 | C | PRO | 89 | 17.572 | 14.611 | 47.385 | 1.00 12.10 |
| ATOM | 674 | O | PRO | 89 | 17.085 | 15.301 | 46.493 | 1.00 18.06 |
| ATOM | 675 | CB | PRO | 89 | 17.733 | 12.294 | 46.494 | 1.00 17.00 |
| ATOM | 676 | CG | PRO | 89 | 17.726 | 11.261 | 47.607 | 1.00 15.83 |
| ATOM | 677 | CD | PRO | 89 | 18.844 | 11.642 | 48.560 | 1.00 17.16 |
| ATOM | 678 | N | GLU | 90 | 17.278 | 14.795 | 48.695 | 1.00 14.63 |
| ATOM | 679 | CA | GLU | 90 | 16.348 | 15.838 | 49.157 | 1.00 20.68 |
| ATOM | 680 | C | GLU | 90 | 16.701 | 17.229 | 48.645 | 1.00 25.59 |
| ATOM | 681 | O | GLU | 90 | 15.833 | 18.042 | 48.368 | 1.00 21.57 |
| ATOM | 682 | CB | GLU | 90 | 16.031 | 15.816 | 50.682 | 1.00 22.21 |
| ATOM | 683 | CG | GLU | 90 | 15.782 | 14.403 | 51.228 | 1.00 37.69 |
| ATOM | 684 | CD | GLU | 90 | 17.071 | 13.641 | 51.447 | 1.00 83.49 |
| ATOM | 685 | OE1 | GLU | 90 | 18.179 | 14.151 | 51.342 | 1.00 54.80 |
| ATOM | 686 | OE2 | GLU | 90 | 16.875 | 12.373 | 51.749 | 1.00 64.65 |
| ATOM | 687 | N | GLY | 91 | 17.977 | 17.509 | 48.510 | 1.00 21.39 |
| ATOM | 688 | CA | GLY | 91 | 18.394 | 18.769 | 47.906 | 1.00 17.77 |
| ATOM | 689 | C | GLY | 91 | 18.673 | 19.911 | 48.839 | 1.00 12.17 |
| ATOM | 690 | O | GLY | 91 | 18.769 | 19.764 | 50.055 | 1.00 16.81 |
| ATOM | 691 | N | TYR | 92 | 18.861 | 21.086 | 48.225 | 1.00 13.02 |

*FIG. 5Q*

| ATOM | 692 | CA  | TYR | 92 | 19.143 | 22.266 | 48.994 | 1.00 | 10.33 |
| ATOM | 693 | C   | TYR | 92 | 18.575 | 23.478 | 48.347 | 1.00 | 9.87 |
| ATOM | 694 | O   | TYR | 92 | 18.270 | 23.483 | 47.144 | 1.00 | 15.89 |
| ATOM | 695 | CB  | TYR | 92 | 20.678 | 22.488 | 49.278 | 1.00 | 15.40 |
| ATOM | 696 | CG  | TYR | 92 | 21.546 | 22.468 | 48.012 | 1.00 | 15.13 |
| ATOM | 697 | CD1 | TYR | 92 | 21.620 | 23.576 | 47.166 | 1.00 | 14.75 |
| ATOM | 698 | CD2 | TYR | 92 | 22.317 | 21.350 | 47.683 | 1.00 | 16.09 |
| ATOM | 699 | CE1 | TYR | 92 | 22.404 | 23.561 | 46.006 | 1.00 | 6.50 |
| ATOM | 700 | CE2 | TYR | 92 | 23.067 | 21.300 | 46.504 | 1.00 | 15.12 |
| ATOM | 701 | CZ  | TYR | 92 | 23.156 | 22.424 | 45.683 | 1.00 | 18.13 |
| ATOM | 702 | OH  | TYR | 92 | 23.944 | 22.393 | 44.517 | 1.00 | 13.37 |
| ATOM | 703 | N   | VAL | 93 | 18.447 | 24.504 | 49.189 | 1.00 | 11.93 |
| ATOM | 704 | CA  | VAL | 93 | 18.025 | 25.822 | 48.778 | 1.00 | 14.74 |
| ATOM | 705 | C   | VAL | 93 | 19.281 | 26.666 | 48.625 | 1.00 | 16.00 |
| ATOM | 706 | O   | VAL | 93 | 20.172 | 26.625 | 49.451 | 1.00 | 16.16 |
| ATOM | 707 | CB  | VAL | 93 | 17.073 | 26.480 | 49.791 | 1.00 | 23.45 |
| ATOM | 708 | CG1 | VAL | 93 | 16.855 | 27.937 | 49.413 | 1.00 | 26.05 |
| ATOM | 709 | CG2 | VAL | 93 | 15.716 | 25.764 | 49.771 | 1.00 | 22.90 |
| ATOM | 710 | N   | GLN | 94 | 19.361 | 27.345 | 47.521 | 1.00 | 13.78 |
| ATOM | 711 | CA  | GLN | 94 | 20.480 | 28.195 | 47.227 | 1.00 | 10.53 |
| ATOM | 712 | C   | GLN | 94 | 19.948 | 29.583 | 46.998 | 1.00 | 12.23 |
| ATOM | 713 | O   | GLN | 94 | 19.153 | 29.788 | 46.061 | 1.00 | 15.52 |
| ATOM | 714 | CB  | GLN | 94 | 21.232 | 27.727 | 45.934 | 1.00 | 7.95 |
| ATOM | 715 | CG  | GLN | 94 | 22.361 | 28.708 | 45.469 | 1.00 | 11.87 |
| ATOM | 716 | CD  | GLN | 94 | 23.431 | 27.999 | 44.632 | 1.00 | 12.04 |
| ATOM | 717 | OE1 | GLN | 94 | 23.805 | 26.879 | 44.946 | 1.00 | 13.60 |
| ATOM | 718 | NE2 | GLN | 94 | 23.719 | 28.527 | 43.449 | 1.00 | 7.98 |
| ATOM | 719 | N   | GLU | 95 | 20.396 | 30.531 | 47.820 | 1.00 | 11.78 |
| ATOM | 720 | CA  | GLU | 95 | 19.974 | 31.899 | 47.643 | 1.00 | 13.47 |
| ATOM | 721 | C   | GLU | 95 | 21.149 | 32.804 | 47.398 | 1.00 | 18.42 |
| ATOM | 722 | O   | GLU | 95 | 22.206 | 32.623 | 47.985 | 1.00 | 19.23 |
| ATOM | 723 | CB  | GLU | 95 | 19.277 | 32.427 | 48.878 | 1.00 | 13.52 |
| ATOM | 724 | CG  | GLU | 95 | 18.009 | 31.684 | 49.215 | 1.00 | 28.46 |
| ATOM | 725 | CD  | GLU | 95 | 17.657 | 32.016 | 50.622 | 1.00 | 45.93 |
| ATOM | 726 | OE1 | GLU | 95 | 17.574 | 33.166 | 51.011 | 1.00 | 100.00 |
| ATOM | 727 | OE2 | GLU | 95 | 17.764 | 30.987 | 51.423 | 1.00 | 61.33 |
| ATOM | 728 | N   | ARG | 96 | 20.929 | 33.838 | 46.601 | 1.00 | 16.51 |
| ATOM | 729 | CA  | ARG | 96 | 21.978 | 34.783 | 46.342 | 1.00 | 16.87 |
| ATOM | 730 | C   | ARG | 96 | 21.510 | 36.195 | 46.206 | 1.00 | 15.84 |
| ATOM | 731 | O   | ARG | 96 | 20.389 | 36.488 | 45.806 | 1.00 | 15.01 |
| ATOM | 732 | CB  | ARG | 96 | 22.582 | 34.463 | 44.967 | 1.00 | 16.19 |

*FIG. 5R*

| | | | | | | | |
|---|---|---|---|---|---|---|---|
| ATOM | 733 | CG  | ARG | 96  | 23.495 | 33.247 | 44.929 | 1.00 17.61 |
| ATOM | 734 | CD  | ARG | 96  | 24.615 | 33.453 | 43.908 | 1.00  9.06 |
| ATOM | 735 | NE  | ARG | 96  | 25.411 | 32.277 | 43.766 | 1.00  9.88 |
| ATOM | 736 | CZ  | ARG | 96  | 25.434 | 31.493 | 42.693 | 1.00 20.03 |
| ATOM | 737 | NH1 | ARG | 96  | 24.684 | 31.709 | 41.615 | 1.00 15.29 |
| ATOM | 738 | NH2 | ARG | 96  | 26.236 | 30.430 | 42.714 | 1.00 11.03 |
| ATOM | 739 | N   | THR | 97  | 22.470 | 37.068 | 46.344 | 1.00 13.39 |
| ATOM | 740 | CA  | THR | 97  | 22.368 | 38.424 | 45.935 | 1.00 13.12 |
| ATOM | 741 | C   | THR | 97  | 23.593 | 38.688 | 45.084 | 1.00 16.81 |
| ATOM | 742 | O   | THR | 97  | 24.686 | 38.347 | 45.485 | 1.00 19.25 |
| ATOM | 743 | CB  | THR | 97  | 22.282 | 39.442 | 47.066 | 1.00 26.27 |
| ATOM | 744 | OG1 | THR | 97  | 21.225 | 39.101 | 47.945 | 1.00 31.43 |
| ATOM | 745 | CG2 | THR | 97  | 22.038 | 40.804 | 46.445 | 1.00 15.90 |
| ATOM | 746 | N   | ILE | 98  | 23.396 | 39.219 | 43.899 | 1.00 16.23 |
| ATOM | 747 | CA  | ILE | 98  | 24.486 | 39.526 | 42.977 | 1.00 16.70 |
| ATOM | 748 | C   | ILE | 98  | 24.533 | 41.017 | 42.686 | 1.00 21.10 |
| ATOM | 749 | O   | ILE | 98  | 23.628 | 41.566 | 42.075 | 1.00 14.58 |
| ATOM | 750 | CB  | ILE | 98  | 24.385 | 38.752 | 41.660 | 1.00 13.47 |
| ATOM | 751 | CG1 | ILE | 98  | 24.480 | 37.236 | 41.890 | 1.00 16.09 |
| ATOM | 752 | CG2 | ILE | 98  | 25.457 | 39.231 | 40.679 | 1.00 13.30 |
| ATOM | 753 | CD1 | ILE | 98  | 23.875 | 36.431 | 40.738 | 1.00 13.93 |
| ATOM | 754 | N   | PHE | 99  | 25.613 | 41.678 | 43.110 | 1.00 14.86 |
| ATOM | 755 | CA  | PHE | 99  | 25.719 | 43.098 | 42.896 | 1.00 12.44 |
| ATOM | 756 | C   | PHE | 99  | 26.514 | 43.441 | 41.699 | 1.00 20.37 |
| ATOM | 757 | O   | PHE | 99  | 27.696 | 43.164 | 41.700 | 1.00 20.07 |
| ATOM | 758 | CB  | PHE | 99  | 26.401 | 43.770 | 44.084 | 1.00 15.96 |
| ATOM | 759 | CG  | PHE | 99  | 25.638 | 43.624 | 45.356 | 1.00 21.41 |
| ATOM | 760 | CD1 | PHE | 99  | 25.863 | 42.524 | 46.189 | 1.00 24.98 |
| ATOM | 761 | CD2 | PHE | 99  | 24.698 | 44.585 | 45.743 | 1.00 22.94 |
| ATOM | 762 | CE1 | PHE | 99  | 25.176 | 42.400 | 47.400 | 1.00 32.06 |
| ATOM | 763 | CE2 | PHE | 99  | 23.992 | 44.469 | 46.946 | 1.00 24.26 |
| ATOM | 764 | CZ  | PHE | 99  | 24.235 | 43.369 | 47.771 | 1.00 28.19 |
| ATOM | 765 | N   | PHE | 100 | 25.906 | 44.085 | 40.704 | 1.00 12.53 |
| ATOM | 766 | CA  | PHE | 100 | 26.679 | 44.522 | 39.554 | 1.00  8.75 |
| ATOM | 767 | C   | PHE | 100 | 27.294 | 45.855 | 39.872 | 1.00 21.81 |
| ATOM | 768 | O   | PHE | 100 | 26.599 | 46.775 | 40.308 | 1.00 20.31 |
| ATOM | 769 | CB  | PHE | 100 | 25.927 | 44.572 | 38.226 | 1.00  5.94 |
| ATOM | 770 | CG  | PHE | 100 | 25.537 | 43.183 | 37.764 | 1.00 12.75 |
| ATOM | 771 | CD1 | PHE | 100 | 24.426 | 42.538 | 38.325 | 1.00 16.31 |
| ATOM | 772 | CD2 | PHE | 100 | 26.317 | 42.484 | 36.843 | 1.00 15.27 |
| ATOM | 773 | CE1 | PHE | 100 | 24.087 | 41.230 | 37.975 | 1.00 13.50 |

*FIG. 5S*

| ATOM | 774 | CE2 | PHE | 100 | 25.965 | 41.192 | 36.435 | 1.00 | 21.25 |
|------|-----|-----|-----|-----|--------|--------|--------|------|-------|
| ATOM | 775 | CZ | PHE | 100 | 24.852 | 40.567 | 37.014 | 1.00 | 21.06 |
| ATOM | 776 | N | LYS | 101 | 28.603 | 45.946 | 39.737 | 1.00 | 15.49 |
| ATOM | 777 | CA | LYS | 101 | 29.270 | 47.179 | 40.085 | 1.00 | 17.93 |
| ATOM | 778 | C | LYS | 101 | 28.732 | 48.349 | 39.287 | 1.00 | 13.71 |
| ATOM | 779 | O | LYS | 101 | 28.658 | 48.304 | 38.072 | 1.00 | 17.18 |
| ATOM | 780 | CB | LYS | 101 | 30.784 | 47.069 | 39.950 | 1.00 | 17.13 |
| ATOM | 781 | CG | LYS | 101 | 31.518 | 48.252 | 40.551 | 1.00 | 18.01 |
| ATOM | 782 | CD | LYS | 101 | 33.036 | 48.060 | 40.534 | 1.00 | 26.70 |
| ATOM | 783 | CE | LYS | 101 | 33.797 | 49.116 | 41.332 | 1.00 | 41.58 |
| ATOM | 784 | N | ASP | 102 | 28.353 | 49.403 | 39.997 | 1.00 | 18.09 |
| ATOM | 785 | CA | ASP | 102 | 27.805 | 50.618 | 39.368 | 1.00 | 23.08 |
| ATOM | 786 | C | ASP | 102 | 26.559 | 50.356 | 38.549 | 1.00 | 25.42 |
| ATOM | 787 | O | ASP | 102 | 26.292 | 51.061 | 37.586 | 1.00 | 23.34 |
| ATOM | 788 | CB | ASP | 102 | 28.840 | 51.369 | 38.516 | 1.00 | 26.27 |
| ATOM | 789 | CG | ASP | 102 | 30.109 | 51.629 | 39.296 | 1.00 | 57.01 |
| ATOM | 790 | OD1 | ASP | 102 | 31.206 | 51.233 | 38.931 | 1.00 | 63.33 |
| ATOM | 791 | OD2 | ASP | 102 | 29.886 | 52.200 | 40.464 | 1.00 | 47.66 |
| ATOM | 792 | N | ASP | 103 | 25.813 | 49.328 | 38.933 | 1.00 | 20.17 |
| ATOM | 793 | CA | ASP | 103 | 24.602 | 48.949 | 38.233 | 1.00 | 15.70 |
| ATOM | 794 | C | ASP | 103 | 23.608 | 48.284 | 39.189 | 1.00 | 18.47 |
| ATOM | 795 | O | ASP | 103 | 23.749 | 48.431 | 40.409 | 1.00 | 17.72 |
| ATOM | 796 | CB | ASP | 103 | 24.899 | 48.085 | 36.995 | 1.00 | 19.89 |
| ATOM | 797 | CG | ASP | 103 | 23.946 | 48.387 | 35.860 | 1.00 | 23.93 |
| ATOM | 798 | OD1 | ASP | 103 | 24.238 | 48.274 | 34.688 | 1.00 | 19.05 |
| ATOM | 799 | OD2 | ASP | 103 | 22.774 | 48.809 | 36.283 | 1.00 | 23.89 |
| ATOM | 800 | N | GLY | 104 | 22.612 | 47.542 | 38.646 | 1.00 | 20.17 |
| ATOM | 801 | CA | GLY | 104 | 21.598 | 46.900 | 39.498 | 1.00 | 20.22 |
| ATOM | 802 | C | GLY | 104 | 22.055 | 45.619 | 40.180 | 1.00 | 24.68 |
| ATOM | 803 | O | GLY | 104 | 23.202 | 45.211 | 40.085 | 1.00 | 18.06 |
| ATOM | 804 | N | ASN | 105 | 21.125 | 44.967 | 40.872 | 1.00 | 15.71 |
| ATOM | 805 | CA | ASN | 105 | 21.425 | 43.703 | 41.510 | 1.00 | 8.89 |
| ATOM | 806 | C | ASN | 105 | 20.399 | 42.620 | 41.181 | 1.00 | 21.85 |
| ATOM | 807 | O | ASN | 105 | 19.255 | 42.911 | 40.824 | 1.00 | 15.17 |
| ATOM | 808 | CB | ASN | 105 | 21.605 | 43.840 | 43.001 | 1.00 | 8.58 |
| ATOM | 809 | CG | ASN | 105 | 20.359 | 44.366 | 43.697 | 1.00 | 43.57 |
| ATOM | 810 | OD1 | ASN | 105 | 19.565 | 43.601 | 44.259 | 1.00 | 36.67 |
| ATOM | 811 | ND2 | ASN | 105 | 20.178 | 45.674 | 43.659 | 1.00 | 36.47 |
| ATOM | 812 | N | TYR | 106 | 20.826 | 41.365 | 41.328 | 1.00 | 16.80 |
| ATOM | 813 | CA | TYR | 106 | 19.966 | 40.219 | 41.156 | 1.00 | 13.90 |
| ATOM | 814 | C | TYR | 106 | 19.763 | 39.543 | 42.475 | 1.00 | 11.05 |

*FIG. 5T*

| | | | | | | | | |
|---|---|---|---|---|---|---|---|---|
| ATOM | 815 | O | TYR | 106 | 20.678 | 39.404 | 43.281 | 1.00 13.86 |
| ATOM | 816 | CB | TYR | 106 | 20.547 | 39.128 | 40.246 | 1.00 15.88 |
| ATOM | 817 | CG | TYR | 106 | 20.619 | 39.398 | 38.793 | 1.00 15.57 |
| ATOM | 818 | CD1 | TYR | 106 | 19.952 | 40.458 | 38.178 | 1.00 13.14 |
| ATOM | 819 | CD2 | TYR | 106 | 21.373 | 38.524 | 38.006 | 1.00 13.35 |
| ATOM | 820 | CE1 | TYR | 106 | 20.038 | 40.632 | 36.793 | 1.00 13.44 |
| ATOM | 821 | CE2 | TYR | 106 | 21.481 | 38.692 | 36.628 | 1.00 10.87 |
| ATOM | 822 | CZ | TYR | 106 | 20.814 | 39.751 | 36.025 | 1.00 15.93 |
| ATOM | 823 | OH | TYR | 106 | 20.970 | 39.931 | 34.670 | 1.00 17.32 |
| ATOM | 824 | N | LYS | 107 | 18.538 | 39.115 | 42.709 | 1.00 12.39 |
| ATOM | 825 | CA | LYS | 107 | 18.194 | 38.349 | 43.897 | 1.00 11.51 |
| ATOM | 826 | C | LYS | 107 | 17.619 | 37.037 | 43.397 | 1.00 17.25 |
| ATOM | 827 | O | LYS | 107 | 16.704 | 37.010 | 42.562 | 1.00 13.14 |
| ATOM | 828 | CB | LYS | 107 | 17.217 | 39.063 | 44.823 | 1.00 14.82 |
| ATOM | 829 | CG | LYS | 107 | 17.860 | 39.631 | 46.060 | 1.00 40.71 |
| ATOM | 830 | CD | LYS | 107 | 18.528 | 40.974 | 45.793 | 1.00 43.48 |
| ATOM | 831 | N | THR | 108 | 18.205 | 35.951 | 43.835 | 1.00 14.95 |
| ATOM | 832 | CA | THR | 108 | 17.774 | 34.658 | 43.352 | 1.00 11.97 |
| ATOM | 833 | C | THR | 108 | 17.463 | 33.696 | 44.468 | 1.00 15.81 |
| ATOM | 834 | O | THR | 108 | 18.043 | 33.734 | 45.582 | 1.00 18.68 |
| ATOM | 835 | CB | THR | 108 | 18.847 | 34.034 | 42.410 | 1.00 23.81 |
| ATOM | 836 | OG1 | THR | 108 | 20.064 | 33.791 | 43.137 | 1.00 13.88 |
| ATOM | 837 | CG2 | THR | 108 | 19.123 | 34.968 | 41.264 | 1.00 13.04 |
| ATOM | 838 | N | ARG | 109 | 16.560 | 32.804 | 44.154 | 1.00 13.57 |
| ATOM | 839 | CA | ARG | 109 | 16.212 | 31.751 | 45.048 | 1.00 12.56 |
| ATOM | 840 | C | ARG | 109 | 15.939 | 30.498 | 44.254 | 1.00 13.07 |
| ATOM | 841 | O | ARG | 109 | 15.239 | 30.509 | 43.249 | 1.00 12.52 |
| ATOM | 842 | CB | ARG | 109 | 15.069 | 32.100 | 45.959 | 1.00 17.32 |
| ATOM | 843 | CG | ARG | 109 | 14.767 | 30.995 | 46.932 | 1.00 17.92 |
| ATOM | 844 | CD | ARG | 109 | 13.400 | 31.160 | 47.610 | 1.00 19.99 |
| ATOM | 845 | NE | ARG | 109 | 12.821 | 29.854 | 47.883 | 1.00 36.05 |
| ATOM | 846 | CZ | ARG | 109 | 12.968 | 29.244 | 49.035 | 1.00 55.71 |
| ATOM | 847 | NH1 | ARG | 109 | 13.630 | 29.815 | 50.046 | 1.00 44.11 |
| ATOM | 848 | NH2 | ARG | 109 | 12.432 | 28.041 | 49.195 | 1.00 94.34 |
| ATOM | 849 | N | ALA | 110 | 16.577 | 29.414 | 44.635 | 1.00 13.26 |
| ATOM | 850 | CA | ALA | 110 | 16.377 | 28.207 | 43.870 | 1.00 12.68 |
| ATOM | 851 | C | ALA | 110 | 16.346 | 26.979 | 44.734 | 1.00 13.15 |
| ATOM | 852 | O | ALA | 110 | 16.829 | 26.965 | 45.869 | 1.00 16.75 |
| ATOM | 853 | CB | ALA | 110 | 17.465 | 28.059 | 42.822 | 1.00 17.31 |
| ATOM | 854 | N | GLU | 111 | 15.770 | 25.939 | 44.176 | 1.00 15.39 |
| ATOM | 855 | CA | GLU | 111 | 15.741 | 24.655 | 44.823 | 1.00 15.24 |

*FIG. 5U*

| ATOM | 856 | C | GLU | 111 | 16.438 | 23.678 | 43.926 | 1.00 | 12.08 |
|------|-----|-----|-----|-----|--------|--------|--------|------|-------|
| ATOM | 857 | O | GLU | 111 | 16.086 | 23.545 | 42.771 | 1.00 | 15.70 |
| ATOM | 858 | CB | GLU | 111 | 14.303 | 24.123 | 44.993 | 1.00 | 19.20 |
| ATOM | 859 | CG | GLU | 111 | 13.744 | 24.242 | 46.399 | 1.00 | 38.62 |
| ATOM | 860 | CD | GLU | 111 | 12.247 | 24.280 | 46.372 | 1.00 | 60.99 |
| ATOM | 861 | OE1 | GLU | 111 | 11.589 | 23.843 | 45.432 | 1.00 | 76.05 |
| ATOM | 862 | OE2 | GLU | 111 | 11.742 | 24.956 | 47.380 | 1.00 | 54.87 |
| ATOM | 863 | N | VAL | 112 | 17.438 | 22.965 | 44.457 | 1.00 | 10.78 |
| ATOM | 864 | CA | VAL | 112 | 18.063 | 21.978 | 43.631 | 1.00 | 10.98 |
| ATOM | 865 | C | VAL | 112 | 17.968 | 20.630 | 44.261 | 1.00 | 8.62 |
| ATOM | 866 | O | VAL | 112 | 18.271 | 20.438 | 45.432 | 1.00 | 15.63 |
| ATOM | 867 | CB | VAL | 112 | 19.428 | 22.358 | 43.012 | 1.00 | 22.75 |
| ATOM | 868 | CG1 | VAL | 112 | 19.966 | 23.704 | 43.487 | 1.00 | 16.69 |
| ATOM | 869 | CG2 | VAL | 112 | 20.452 | 21.232 | 43.078 | 1.00 | 18.47 |
| ATOM | 870 | N | LYS | 113 | 17.415 | 19.732 | 43.516 | 1.00 | 14.67 |
| ATOM | 871 | CA | LYS | 113 | 17.175 | 18.421 | 44.045 | 1.00 | 16.41 |
| ATOM | 872 | C | LYS | 113 | 16.822 | 17.485 | 42.931 | 1.00 | 7.11 |
| ATOM | 873 | O | LYS | 113 | 16.695 | 17.893 | 41.808 | 1.00 | 16.27 |
| ATOM | 874 | CB | LYS | 113 | 16.032 | 18.497 | 45.036 | 1.00 | 22.50 |
| ATOM | 875 | CG | LYS | 113 | 14.792 | 19.084 | 44.376 | 1.00 | 20.40 |
| ATOM | 876 | CD | LYS | 113 | 13.509 | 18.321 | 44.703 | 1.00 | 44.65 |
| ATOM | 877 | CE | LYS | 113 | 12.526 | 19.134 | 45.528 | 1.00 | 54.02 |
| ATOM | 878 | NZ | LYS | 113 | 12.379 | 20.518 | 45.036 | 1.00 | 100.00 |
| ATOM | 879 | N | PHE | 114 | 16.683 | 16.208 | 43.267 | 1.00 | 10.09 |
| ATOM | 880 | CA | PHE | 114 | 16.325 | 15.175 | 42.317 | 1.00 | 11.41 |
| ATOM | 881 | C | PHE | 114 | 14.806 | 14.975 | 42.181 | 1.00 | 14.18 |
| ATOM | 882 | O | PHE | 114 | 14.110 | 14.878 | 43.160 | 1.00 | 15.03 |
| ATOM | 883 | CB | PHE | 114 | 16.866 | 13.838 | 42.838 | 1.00 | 12.89 |
| ATOM | 884 | CG | PHE | 114 | 18.231 | 13.536 | 42.338 | 1.00 | 16.80 |
| ATOM | 885 | CD1 | PHE | 114 | 19.344 | 13.795 | 43.139 | 1.00 | 18.61 |
| ATOM | 886 | CD2 | PHE | 114 | 18.403 | 13.009 | 41.056 | 1.00 | 19.50 |
| ATOM | 887 | CE1 | PHE | 114 | 20.627 | 13.500 | 42.665 | 1.00 | 22.78 |
| ATOM | 888 | CE2 | PHE | 114 | 19.673 | 12.708 | 40.572 | 1.00 | 25.36 |
| ATOM | 889 | CZ | PHE | 114 | 20.780 | 12.953 | 41.387 | 1.00 | 23.99 |
| ATOM | 890 | N | GLU | 115 | 14.354 | 14.819 | 40.966 | 1.00 | 15.29 |
| ATOM | 891 | CA | GLU | 115 | 12.978 | 14.473 | 40.642 | 1.00 | 11.40 |
| ATOM | 892 | C | GLU | 115 | 13.121 | 13.193 | 39.906 | 1.00 | 13.30 |
| ATOM | 893 | O | GLU | 115 | 13.434 | 13.207 | 38.730 | 1.00 | 18.72 |
| ATOM | 894 | CB | GLU | 115 | 12.348 | 15.481 | 39.667 | 1.00 | 9.68 |
| ATOM | 895 | CG | GLU | 115 | 11.856 | 16.747 | 40.376 | 1.00 | 19.54 |
| ATOM | 896 | CD | GLU | 115 | 10.742 | 16.460 | 41.342 | 1.00 | 38.12 |

*FIG. 5V*

| | | | | | | | |
|---|---|---|---|---|---|---|---|
| ATOM | 897 | OE1 GLU | 115 | 10.181 | 15.395 | 41.431 | 1.00 34.84 |
| ATOM | 898 | OE2 GLU | 115 | 10.460 | 17.461 | 42.079 | 1.00 27.88 |
| ATOM | 899 | N   GLY | 116 | 13.005 | 12.087 | 40.585 | 1.00 14.51 |
| ATOM | 900 | CA  GLY | 116 | 13.225 | 10.861 | 39.869 | 1.00 15.91 |
| ATOM | 901 | C   GLY | 116 | 14.727 | 10.767 | 39.641 | 1.00 23.59 |
| ATOM | 902 | O   GLY | 116 | 15.516 | 10.922 | 40.570 | 1.00 19.35 |
| ATOM | 903 | N   ASP | 117 | 15.137 | 10.564 | 38.439 | 1.00 20.26 |
| ATOM | 904 | CA  ASP | 117 | 16.572 | 10.462 | 38.233 | 1.00 28.00 |
| ATOM | 905 | C   ASP | 117 | 17.237 | 11.677 | 37.598 | 1.00 22.39 |
| ATOM | 906 | O   ASP | 117 | 18.423 | 11.672 | 37.265 | 1.00 21.38 |
| ATOM | 907 | CB  ASP | 117 | 17.055 | 9.074  | 37.733 | 1.00 33.06 |
| ATOM | 908 | CG  ASP | 117 | 16.624 | 8.677  | 36.348 | 1.00 55.04 |
| ATOM | 909 | OD1 ASP | 117 | 16.230 | 9.468  | 35.495 | 1.00 59.57 |
| ATOM | 910 | OD2 ASP | 117 | 16.805 | 7.391  | 36.130 | 1.00 82.48 |
| ATOM | 911 | N   THR | 118 | 16.463 | 12.729 | 37.493 | 1.00 19.62 |
| ATOM | 912 | CA  THR | 118 | 16.889 | 13.981 | 36.910 | 1.00 18.21 |
| ATOM | 913 | C   THR | 118 | 17.186 | 14.988 | 37.976 | 1.00 18.92 |
| ATOM | 914 | O   THR | 118 | 16.498 | 15.064 | 38.996 | 1.00 15.94 |
| ATOM | 915 | CB  THR | 118 | 15.806 | 14.497 | 35.952 | 1.00 19.03 |
| ATOM | 916 | OG1 THR | 118 | 15.552 | 13.508 | 34.990 | 1.00 21.42 |
| ATOM | 917 | CG2 THR | 118 | 16.217 | 15.793 | 35.275 | 1.00 15.49 |
| ATOM | 918 | N   LEU | 119 | 18.284 | 15.681 | 37.805 | 1.00 13.66 |
| ATOM | 919 | CA  LEU | 119 | 18.679 | 16.706 | 38.759 | 1.00 13.50 |
| ATOM | 920 | C   LEU | 119 | 18.036 | 17.992 | 38.269 | 1.00  8.81 |
| ATOM | 921 | O   LEU | 119 | 18.194 | 18.368 | 37.091 | 1.00 12.49 |
| ATOM | 922 | CB  LEU | 119 | 20.243 | 16.815 | 38.839 | 1.00 12.25 |
| ATOM | 923 | CG  LEU | 119 | 20.845 | 17.678 | 39.951 | 1.00  3.90 |
| ATOM | 924 | CD1 LEU | 119 | 20.701 | 19.167 | 39.669 | 1.00 10.11 |
| ATOM | 925 | CD2 LEU | 119 | 20.366 | 17.311 | 41.333 | 1.00  7.86 |
| ATOM | 926 | N   VAL | 120 | 17.230 | 18.595 | 39.170 | 1.00 13.34 |
| ATOM | 927 | CA  VAL | 120 | 16.466 | 19.797 | 38.859 | 1.00 13.77 |
| ATOM | 928 | C   VAL | 120 | 16.929 | 21.039 | 39.587 | 1.00  8.56 |
| ATOM | 929 | O   VAL | 120 | 17.135 | 21.039 | 40.762 | 1.00 13.32 |
| ATOM | 930 | CB  VAL | 120 | 14.939 | 19.566 | 39.082 | 1.00 17.60 |
| ATOM | 931 | CG1 VAL | 120 | 14.133 | 20.790 | 38.642 | 1.00 17.58 |
| ATOM | 932 | CG2 VAL | 120 | 14.501 | 18.351 | 38.246 | 1.00 15.35 |
| ATOM | 933 | N   ASN | 121 | 17.067 | 22.111 | 38.839 | 1.00 12.24 |
| ATOM | 934 | CA  ASN | 121 | 17.424 | 23.405 | 39.400 | 1.00 11.78 |
| ATOM | 935 | C   ASN | 121 | 16.301 | 24.382 | 39.060 | 1.00 11.18 |
| ATOM | 936 | O   ASN | 121 | 16.195 | 24.802 | 37.934 | 1.00 11.09 |
| ATOM | 937 | CB  ASN | 121 | 18.753 | 23.928 | 38.791 | 1.00 11.41 |

*FIG. 5W*

| | | | | | | | | |
|---|---|---|---|---|---|---|---|---|
| ATOM | 938 | CG | ASN | 121 | 19.201 | 25.261 | 39.367 | 1.00 11.07 |
| ATOM | 939 | OD | ASN | 121 | 18.773 | 25.654 | 40.461 | 1.00 12.06 |
| ATOM | 940 | ND2 | ASN | 121 | 20.124 | 25.938 | 38.670 | 1.00 11.90 |
| ATOM | 941 | N | ARG | 122 | 15.470 | 24.706 | 40.029 | 1.00 13.69 |
| ATOM | 942 | CA | ARG | 122 | 14.348 | 25.610 | 39.825 | 1.00 12.99 |
| ATOM | 943 | C | ARG | 122 | 14.622 | 26.946 | 40.498 | 1.00 5.89 |
| ATOM | 944 | O | ARG | 122 | 14.749 | 27.011 | 41.723 | 1.00 14.47 |
| ATOM | 945 | CB | ARG | 122 | 13.068 | 25.025 | 40.417 | 1.00 15.99 |
| ATOM | 946 | CG | ARG | 122 | 12.478 | 23.921 | 39.589 | 1.00 30.23 |
| ATOM | 947 | CD | ARG | 122 | 11.282 | 23.244 | 40.281 | 1.00 60.61 |
| ATOM | 948 | N | ILE | 123 | 14.663 | 27.992 | 39.680 | 1.00 11.46 |
| ATOM | 949 | CA | ILE | 123 | 15.030 | 29.340 | 40.095 | 1.00 11.86 |
| ATOM | 950 | C | ILE | 123 | 13.991 | 30.450 | 39.835 | 1.00 10.54 |
| ATOM | 951 | O | ILE | 123 | 13.370 | 30.535 | 38.765 | 1.00 12.83 |
| ATOM | 952 | CB | ILE | 123 | 16.296 | 29.757 | 39.292 | 1.00 15.41 |
| ATOM | 953 | CG1 | ILE | 123 | 17.316 | 28.585 | 39.180 | 1.00 12.27 |
| ATOM | 954 | CG2 | ILE | 123 | 16.944 | 30.993 | 39.918 | 1.00 14.01 |
| ATOM | 955 | CD1 | ILE | 123 | 17.652 | 28.242 | 37.743 | 1.00 7.74 |
| ATOM | 956 | N | GLU | 124 | 13.953 | 31.358 | 40.793 | 1.00 11.36 |
| ATOM | 957 | CA | GLU | 124 | 13.189 | 32.752 | 40.700 | 1.00 15.20 |
| ATOM | 958 | C | GLU | 124 | 14.168 | 33.713 | 40.811 | 1.00 11.93 |
| ATOM | 959 | O | GLU | 124 | 14.919 | 33.797 | 41.780 | 1.00 15.61 |
| ATOM | 960 | CB | GLU | 124 | 12.028 | 32.677 | 41.751 | 1.00 19.74 |
| ATOM | 961 | CG | GLU | 124 | 12.387 | 33.337 | 43.089 | 1.00 72.94 |
| ATOM | 962 | N | LEU | 125 | 14.183 | 34.550 | 39.808 | 1.00 12.19 |
| ATOM | 963 | CA | LEU | 125 | 15.092 | 35.654 | 39.767 | 1.00 15.00 |
| ATOM | 964 | C | LEU | 125 | 14.420 | 37.011 | 39.722 | 1.00 19.35 |
| ATOM | 965 | O | LEU | 125 | 13.563 | 37.267 | 38.893 | 1.00 18.41 |
| ATOM | 966 | CB | LEU | 125 | 15.976 | 35.533 | 38.510 | 1.00 14.29 |
| ATOM | 967 | CG | LEU | 125 | 17.003 | 36.683 | 38.375 | 1.00 17.65 |
| ATOM | 968 | CD1 | LEU | 125 | 18.302 | 36.083 | 37.849 | 1.00 13.46 |
| ATOM | 969 | CD2 | LEU | 125 | 16.511 | 37.732 | 37.367 | 1.00 12.09 |
| ATOM | 970 | N | LYS | 126 | 14.890 | 37.897 | 40.554 | 1.00 12.73 |
| ATOM | 971 | CA | LYS | 126 | 14.391 | 39.260 | 40.579 | 1.00 15.92 |
| ATOM | 972 | C | LYS | 126 | 15.563 | 40.276 | 40.445 | 1.00 18.53 |
| ATOM | 973 | O | LYS | 126 | 16.489 | 40.246 | 41.246 | 1.00 19.86 |
| ATOM | 974 | CB | LYS | 126 | 13.611 | 39.487 | 41.877 | 1.00 17.31 |
| ATOM | 975 | CG | LYS | 126 | 12.853 | 40.786 | 41.923 | 1.00 33.94 |
| ATOM | 976 | CD | LYS | 126 | 11.366 | 40.601 | 41.675 | 1.00 60.87 |
| ATOM | 977 | CE | LYS | 126 | 10.652 | 41.929 | 41.521 | 1.00 52.70 |
| ATOM | 978 | NZ | LYS | 126 | 11.229 | 42.988 | 42.367 | 1.00 47.22 |

*FIG. 5X*

| ATOM | 979 | N | GLY | 127 | 15.514 | 41.127 | 39.411 | 1.00 18.71 |
|------|-----|------|------|-----|--------|--------|--------|------------|
| ATOM | 980 | CA | GLY | 127 | 16.551 | 42.151 | 39.121 | 1.00 17.32 |
| ATOM | 981 | C | GLY | 127 | 16.012 | 43.572 | 39.272 | 1.00 25.32 |
| ATOM | 982 | O | GLY | 127 | 14.981 | 43.908 | 38.693 | 1.00 20.14 |
| ATOM | 983 | N | ILE | 128 | 16.706 | 44.404 | 40.070 | 1.00 18.42 |
| ATOM | 984 | CA | ILE | 128 | 16.282 | 45.787 | 40.243 | 1.00 21.04 |
| ATOM | 985 | C | ILE | 128 | 17.405 | 46.789 | 40.196 | 1.00 25.93 |
| ATOM | 986 | O | ILE | 128 | 18.562 | 46.496 | 40.429 | 1.00 19.37 |
| ATOM | 987 | CB | ILE | 128 | 15.482 | 46.052 | 41.504 | 1.00 23.82 |
| ATOM | 988 | CG1 | ILE | 128 | 16.408 | 45.888 | 42.701 | 1.00 23.86 |
| ATOM | 989 | CG2 | ILE | 128 | 14.272 | 45.120 | 41.577 | 1.00 28.95 |
| ATOM | 990 | CD1 | ILE | 128 | 15.824 | 46.391 | 44.013 | 1.00 29.89 |
| ATOM | 991 | N | ASP | 129 | 16.999 | 48.002 | 39.918 | 1.00 20.26 |
| ATOM | 992 | CA | ASP | 129 | 17.861 | 49.124 | 39.882 | 1.00 18.53 |
| ATOM | 993 | C | ASP | 129 | 18.864 | 49.086 | 38.801 | 1.00 20.36 |
| ATOM | 994 | O | ASP | 129 | 19.949 | 49.632 | 38.953 | 1.00 24.28 |
| ATOM | 995 | CB | ASP | 129 | 18.498 | 49.407 | 41.253 | 1.00 20.57 |
| ATOM | 996 | CG | ASP | 129 | 17.545 | 50.077 | 42.226 | 1.00 43.70 |
| ATOM | 997 | OD1 | ASP | 129 | 16.653 | 50.842 | 41.883 | 1.00 49.42 |
| ATOM | 998 | OD2 | ASP | 129 | 17.770 | 49.740 | 43.475 | 1.00 38.07 |
| ATOM | 999 | N | PHE | 130 | 18.510 | 48.493 | 37.693 | 1.00 16.40 |
| ATOM | 1000 | CA | PHE | 130 | 19.433 | 48.459 | 36.563 | 1.00 16.99 |
| ATOM | 1001 | C | PHE | 130 | 19.330 | 49.732 | 35.576 | 1.00 35.37 |
| ATOM | 1002 | O | PHE | 130 | 18.242 | 50.318 | 35.623 | 1.00 27.34 |
| ATOM | 1003 | CB | PHE | 130 | 19.248 | 47.223 | 35.657 | 1.00 18.07 |
| ATOM | 1004 | CG | PHE | 130 | 19.809 | 45.980 | 36.312 | 1.00 19.10 |
| ATOM | 1005 | CD1 | PHE | 130 | 19.021 | 45.210 | 37.171 | 1.00 16.15 |
| ATOM | 1006 | CD2 | PHE | 130 | 21.126 | 45.572 | 36.073 | 1.00 19.17 |
| ATOM | 1007 | CE1 | PHE | 130 | 19.536 | 44.074 | 37.801 | 1.00 23.37 |
| ATOM | 1008 | CE2 | PHE | 130 | 21.665 | 44.445 | 36.703 | 1.00 21.11 |
| ATOM | 1009 | CZ | PHE | 130 | 20.867 | 43.703 | 37.575 | 1.00 22.13 |
| ATOM | 1010 | N | LYS | 131 | 20.464 | 50.169 | 35.218 | 1.00 31.09 |
| ATOM | 1011 | CA | LYS | 131 | 20.477 | 51.371 | 34.400 | 1.00 27.52 |
| ATOM | 1012 | C | LYS | 131 | 20.105 | 51.045 | 32.992 | 1.00 25.57 |
| ATOM | 1013 | O | LYS | 131 | 20.695 | 50.169 | 32.343 | 1.00 22.97 |
| ATOM | 1014 | CB | LYS | 131 | 21.796 | 52.109 | 34.438 | 1.00 32.64 |
| ATOM | 1015 | CG | LYS | 131 | 22.153 | 52.633 | 35.813 | 1.00 38.34 |
| ATOM | 1016 | CD | LYS | 131 | 23.646 | 52.886 | 35.975 | 1.00 75.76 |
| ATOM | 1017 | N | GLU | 132 | 19.116 | 51.751 | 32.509 | 1.00 26.88 |
| ATOM | 1018 | CA | GLU | 132 | 18.623 | 51.484 | 31.189 | 1.00 28.42 |
| ATOM | 1019 | C | GLU | 132 | 19.710 | 51.514 | 30.140 | 1.00 36.19 |

*FIG. 5Y*

| ATOM | 1020 O | GLU | 132 | 19.617 | 50.862 | 29.101 | 1.00 | 39.24 |
|---|---|---|---|---|---|---|---|---|
| ATOM | 1021 CB | GLU | 132 | 17.374 | 52.331 | 30.830 | 1.00 | 29.04 |
| ATOM | 1022 N | ASP | 133 | 20.752 | 52.254 | 30.438 | 1.00 | 40.08 |
| ATOM | 1023 CA | ASP | 133 | 21.883 | 52.442 | 29.525 | 1.00 | 45.36 |
| ATOM | 1024 C | ASP | 133 | 23.224 | 51.861 | 30.049 | 1.00 | 50.61 |
| ATOM | 1025 O | ASP | 133 | 24.299 | 52.243 | 29.572 | 1.00 | 52.14 |
| ATOM | 1026 CB | ASP | 133 | 22.063 | 53.946 | 29.332 | 1.00 | 50.45 |
| ATOM | 1027 CG | ASP | 133 | 22.109 | 54.642 | 30.670 | 1.00 | 87.10 |
| ATOM | 1028 OD1 | ASP | 133 | 21.408 | 54.314 | 31.624 | 1.00 | 91.27 |
| ATOM | 1029 OD2 | ASP | 133 | 23.047 | 55.552 | 30.739 | 1.00 | 100.00 |
| ATOM | 1030 N | GLY | 134 | 23.159 | 50.970 | 31.053 | 1.00 | 37.06 |
| ATOM | 1031 CA | GLY | 134 | 24.349 | 50.376 | 31.639 | 1.00 | 30.22 |
| ATOM | 1032 C | GLY | 134 | 24.845 | 49.228 | 30.803 | 1.00 | 23.10 |
| ATOM | 1033 O | GLY | 134 | 24.360 | 48.990 | 29.685 | 1.00 | 19.23 |
| ATOM | 1034 N | ASN | 135 | 25.807 | 48.486 | 31.341 | 1.00 | 18.66 |
| ATOM | 1035 CA | ASN | 135 | 26.339 | 47.370 | 30.563 | 1.00 | 18.03 |
| ATOM | 1036 C | ASN | 135 | 25.372 | 46.199 | 30.406 | 1.00 | 15.75 |
| ATOM | 1037 O | ASN | 135 | 25.485 | 45.430 | 29.461 | 1.00 | 16.03 |
| ATOM | 1038 CB | ASN | 135 | 27.665 | 46.883 | 31.139 | 1.00 | 19.27 |
| ATOM | 1039 CG | ASN | 135 | 28.743 | 47.943 | 31.108 | 1.00 | 20.99 |
| ATOM | 1040 OD1 | ASN | 135 | 28.969 | 48.595 | 30.078 | 1.00 | 25.69 |
| ATOM | 1041 ND2 | ASN | 135 | 29.423 | 48.095 | 32.239 | 1.00 | 22.57 |
| ATOM | 1042 N | ILE | 136 | 24.444 | 46.052 | 31.362 | 1.00 | 18.14 |
| ATOM | 1043 CA | ILE | 136 | 23.494 | 44.924 | 31.368 | 1.00 | 19.78 |
| ATOM | 1044 C | ILE | 136 | 22.331 | 45.086 | 30.384 | 1.00 | 23.76 |
| ATOM | 1045 O | ILE | 136 | 22.178 | 44.313 | 29.395 | 1.00 | 22.53 |
| ATOM | 1046 CB | ILE | 136 | 23.078 | 44.500 | 32.804 | 1.00 | 21.24 |
| ATOM | 1047 CG1 | ILE | 136 | 24.230 | 43.728 | 33.423 | 1.00 | 28.44 |
| ATOM | 1048 CG2 | ILE | 136 | 21.899 | 43.543 | 32.770 | 1.00 | 22.77 |
| ATOM | 1049 CD1 | ILE | 136 | 25.346 | 44.596 | 33.935 | 1.00 | 12.39 |
| ATOM | 1050 N | LEU | 137 | 21.543 | 46.117 | 30.640 | 1.00 | 18.21 |
| ATOM | 1051 CA | LEU | 137 | 20.394 | 46.415 | 29.815 | 1.00 | 23.30 |
| ATOM | 1052 C | LEU | 137 | 20.828 | 46.875 | 28.470 | 1.00 | 27.26 |
| ATOM | 1053 O | LEU | 137 | 20.181 | 46.619 | 27.488 | 1.00 | 27.00 |
| ATOM | 1054 CB | LEU | 137 | 19.442 | 47.430 | 30.490 | 1.00 | 21.74 |
| ATOM | 1055 CG | LEU | 137 | 18.828 | 46.852 | 31.762 | 1.00 | 22.56 |
| ATOM | 1056 CD1 | LEU | 137 | 17.856 | 47.837 | 32.415 | 1.00 | 22.27 |
| ATOM | 1057 CD2 | LEU | 137 | 18.118 | 45.554 | 31.424 | 1.00 | 37.52 |
| ATOM | 1058 N | GLY | 138 | 21.979 | 47.527 | 28.432 | 1.00 | 22.14 |
| ATOM | 1059 CA | GLY | 138 | 22.510 | 48.033 | 27.187 | 1.00 | 20.03 |
| ATOM | 1060 C | GLY | 138 | 23.157 | 46.959 | 26.368 | 1.00 | 20.16 |

*FIG. 5Z*

| | | | | | | | |
|---|---|---|---|---|---|---|---|
| ATOM | 1061 | O | GLY | 138 | 23.600 | 47.202 | 25.264 | 1.00 22.44 |
| ATOM | 1062 | N | HIS | 139 | 23.246 | 45.756 | 26.903 | 1.00 18.27 |
| ATOM | 1063 | CA | HIS | 139 | 23.859 | 44.655 | 26.148 | 1.00 20.24 |
| ATOM | 1064 | C | HIS | 139 | 25.301 | 44.929 | 25.616 | 1.00 20.13 |
| ATOM | 1065 | O | HIS | 139 | 25.605 | 44.745 | 24.439 | 1.00 17.97 |
| ATOM | 1066 | CB | HIS | 139 | 22.931 | 44.207 | 25.018 | 1.00 22.20 |
| ATOM | 1067 | CG | HIS | 139 | 21.708 | 43.551 | 25.550 | 1.00 25.52 |
| ATOM | 1068 | ND1 | HIS | 139 | 21.666 | 42.182 | 25.785 | 1.00 25.67 |
| ATOM | 1069 | CD2 | HIS | 139 | 20.525 | 44.092 | 25.927 | 1.00 28.09 |
| ATOM | 1070 | CE1 | HIS | 139 | 20.474 | 41.918 | 26.275 | 1.00 27.50 |
| ATOM | 1071 | NE2 | HIS | 139 | 19.766 | 43.044 | 26.382 | 1.00 29.53 |
| ATOM | 1072 | N | LYS | 140 | 26.187 | 45.311 | 26.525 | 1.00 23.51 |
| ATOM | 1073 | CA | LYS | 140 | 27.569 | 45.638 | 26.197 | 1.00 25.82 |
| ATOM | 1074 | C | LYS | 140 | 28.600 | 44.537 | 26.560 | 1.00 26.28 |
| ATOM | 1075 | O | LYS | 140 | 29.824 | 44.730 | 26.391 | 1.00 22.29 |
| ATOM | 1076 | CB | LYS | 140 | 27.977 | 46.937 | 26.911 | 1.00 27.56 |
| ATOM | 1077 | CG | LYS | 140 | 27.269 | 48.217 | 26.445 | 1.00 31.19 |
| ATOM | 1078 | CD | LYS | 140 | 27.234 | 49.254 | 27.582 | 1.00 51.32 |
| ATOM | 1079 | CE | LYS | 140 | 26.924 | 50.696 | 27.169 | 1.00 47.92 |
| ATOM | 1080 | NZ | LYS | 140 | 27.112 | 51.663 | 28.284 | 1.00 73.76 |
| ATOM | 1081 | N | LEU | 141 | 28.116 | 43.403 | 27.115 | 1.00 19.33 |
| ATOM | 1082 | CA | LEU | 141 | 28.987 | 42.296 | 27.559 | 1.00 14.32 |
| ATOM | 1083 | C | LEU | 141 | 29.366 | 41.401 | 26.427 | 1.00 20.75 |
| ATOM | 1084 | O | LEU | 141 | 28.526 | 41.087 | 25.620 | 1.00 19.01 |
| ATOM | 1085 | CB | LEU | 141 | 28.313 | 41.488 | 28.676 | 1.00 12.53 |
| ATOM | 1086 | CG | LEU | 141 | 27.979 | 42.352 | 29.875 | 1.00 17.54 |
| ATOM | 1087 | CD1 | LEU | 141 | 27.700 | 41.469 | 31.070 | 1.00 24.81 |
| ATOM | 1088 | CD2 | LEU | 141 | 29.116 | 43.310 | 30.182 | 1.00 27.50 |
| ATOM | 1089 | N | GLU | 142 | 30.644 | 40.987 | 26.346 | 1.00 14.76 |
| ATOM | 1090 | CA | GLU | 142 | 31.040 | 40.059 | 25.311 | 1.00 13.43 |
| ATOM | 1091 | C | GLU | 142 | 30.462 | 38.691 | 25.641 | 1.00 15.69 |
| ATOM | 1092 | O | GLU | 142 | 30.175 | 38.393 | 26.787 | 1.00 16.43 |
| ATOM | 1093 | CB | GLU | 142 | 32.558 | 39.866 | 25.204 | 1.00 14.73 |
| ATOM | 1094 | CG | GLU | 142 | 33.290 | 41.077 | 24.624 | 1.00 29.30 |
| ATOM | 1095 | CD | GLU | 142 | 34.787 | 41.003 | 24.825 | 1.00 56.32 |
| ATOM | 1096 | OE1 | GLU | 142 | 35.340 | 40.098 | 25.420 | 1.00 31.70 |
| ATOM | 1097 | OE2 | GLU | 142 | 35.430 | 42.015 | 24.321 | 1.00 34.10 |
| ATOM | 1098 | N | TYR | 143 | 30.365 | 37.873 | 24.632 | 1.00 16.30 |
| ATOM | 1099 | CA | TYR | 143 | 29.837 | 36.542 | 24.764 | 1.00 20.04 |
| ATOM | 1100 | C | TYR | 143 | 30.925 | 35.559 | 25.049 | 1.00 12.46 |
| ATOM | 1101 | O | TYR | 143 | 31.327 | 34.792 | 24.193 | 1.00 16.99 |

*FIG. 5AA*

| ATOM | 1102 CB  | TYR | 143 | 29.035 | 36.118 | 23.498 | 1.00 20.96 |
| ATOM | 1103 CG  | TYR | 143 | 28.187 | 34.857 | 23.674 | 1.00 16.12 |
| ATOM | 1104 CD1 | TYR | 143 | 27.040 | 34.859 | 24.472 | 1.00 18.24 |
| ATOM | 1105 CD2 | TYR | 143 | 28.512 | 33.684 | 22.986 | 1.00 12.87 |
| ATOM | 1106 CE1 | TYR | 143 | 26.257 | 33.708 | 24.615 | 1.00 17.91 |
| ATOM | 1107 CE2 | TYR | 143 | 27.735 | 32.530 | 23.104 | 1.00 16.58 |
| ATOM | 1108 CZ  | TYR | 143 | 26.603 | 32.551 | 23.914 | 1.00 17.35 |
| ATOM | 1109 OH  | TYR | 143 | 25.861 | 31.432 | 24.035 | 1.00 23.40 |
| ATOM | 1110 N   | ASN | 144 | 31.392 | 35.597 | 26.251 | 1.00 12.40 |
| ATOM | 1111 CA  | ASN | 144 | 32.428 | 34.703 | 26.689 | 1.00 12.05 |
| ATOM | 1112 C   | ASN | 144 | 32.433 | 34.675 | 28.193 | 1.00 15.75 |
| ATOM | 1113 O   | ASN | 144 | 31.637 | 35.369 | 28.837 | 1.00 14.58 |
| ATOM | 1114 CB  | ASN | 144 | 33.823 | 35.038 | 26.068 | 1.00 18.45 |
| ATOM | 1115 CG  | ASN | 144 | 34.310 | 36.445 | 26.374 | 1.00 18.98 |
| ATOM | 1116 OD1 | ASN | 144 | 34.150 | 36.951 | 27.488 | 1.00 20.34 |
| ATOM | 1117 ND2 | ASN | 144 | 34.891 | 37.085 | 25.382 | 1.00 23.02 |
| ATOM | 1118 N   | TYR | 145 | 33.311 | 33.876 | 28.773 | 1.00 12.16 |
| ATOM | 1119 CA  | TYR | 145 | 33.343 | 33.765 | 30.195 | 1.00 10.63 |
| ATOM | 1120 C   | TYR | 145 | 34.765 | 33.458 | 30.730 | 1.00 14.58 |
| ATOM | 1121 O   | TYR | 145 | 35.510 | 32.751 | 30.090 | 1.00 18.83 |
| ATOM | 1122 CB  | TYR | 145 | 32.404 | 32.627 | 30.571 | 1.00  9.76 |
| ATOM | 1123 CG  | TYR | 145 | 31.698 | 32.916 | 31.826 | 1.00 11.86 |
| ATOM | 1124 CD1 | TYR | 145 | 30.515 | 33.658 | 31.808 | 1.00  9.04 |
| ATOM | 1125 CD2 | TYR | 145 | 32.188 | 32.419 | 33.030 | 1.00 10.07 |
| ATOM | 1126 CE1 | TYR | 145 | 29.860 | 33.948 | 32.999 | 1.00  8.36 |
| ATOM | 1127 CE2 | TYR | 145 | 31.544 | 32.707 | 34.235 | 1.00 15.32 |
| ATOM | 1128 CZ  | TYR | 145 | 30.375 | 33.469 | 34.206 | 1.00 11.69 |
| ATOM | 1129 OH  | TYR | 145 | 29.730 | 33.735 | 35.376 | 1.00 15.23 |
| ATOM | 1130 N   | ASN | 146 | 35.086 | 33.931 | 31.933 | 1.00 15.36 |
| ATOM | 1131 CA  | ASN | 146 | 36.415 | 33.737 | 32.560 | 1.00 17.00 |
| ATOM | 1132 C   | ASN | 146 | 36.426 | 32.618 | 33.589 | 1.00 19.68 |
| ATOM | 1133 O   | ASN | 146 | 35.395 | 32.043 | 33.848 | 1.00 14.71 |
| ATOM | 1134 CB  | ASN | 146 | 36.844 | 35.062 | 33.235 | 1.00 11.89 |
| ATOM | 1135 CG  | ASN | 146 | 37.013 | 36.147 | 32.215 | 1.00 35.45 |
| ATOM | 1136 OD1 | ASN | 146 | 37.533 | 35.890 | 31.105 | 1.00 31.63 |
| ATOM | 1137 ND2 | ASN | 146 | 36.547 | 37.349 | 32.553 | 1.00 19.74 |
| ATOM | 1138 N   | SER | 147 | 37.630 | 32.338 | 34.201 | 1.00 12.09 |
| ATOM | 1139 CA  | SER | 147 | 37.804 | 31.320 | 35.266 | 1.00  8.55 |
| ATOM | 1140 C   | SER | 147 | 37.769 | 31.999 | 36.575 | 1.00 11.70 |
| ATOM | 1141 O   | SER | 147 | 38.219 | 33.125 | 36.671 | 1.00 16.56 |
| ATOM | 1142 CB  | SER | 147 | 39.148 | 30.540 | 35.129 | 1.00  9.87 |
| ATOM | 1143 OG  | SER | 147 | 39.212 | 29.980 | 33.828 | 1.00 33.20 |

*FIG. 5AB*

| | | | | | | | |
|---|---|---|---|---|---|---|---|
| ATOM | 1144 | N   | HIS | 148 | 37.195 | 31.365 | 37.583 | 1.00  5.53 |
| ATOM | 1145 | CA  | HIS | 148 | 37.090 | 31.998 | 38.850 | 1.00  8.06 |
| ATOM | 1146 | C   | HIS | 148 | 37.346 | 31.038 | 39.949 | 1.00 11.30 |
| ATOM | 1147 | O   | HIS | 148 | 37.328 | 29.844 | 39.754 | 1.00 16.87 |
| ATOM | 1148 | CB  | HIS | 148 | 35.648 | 32.608 | 39.067 | 1.00 11.29 |
| ATOM | 1149 | CG  | HIS | 148 | 35.215 | 33.554 | 37.972 | 1.00 10.84 |
| ATOM | 1150 | ND1 | HIS | 148 | 34.548 | 33.121 | 36.836 | 1.00 12.77 |
| ATOM | 1151 | CD2 | HIS | 148 | 35.403 | 34.887 | 37.851 | 1.00  8.82 |
| ATOM | 1152 | CE1 | HIS | 148 | 34.389 | 34.178 | 36.060 | 1.00  8.84 |
| ATOM | 1153 | NE2 | HIS | 148 | 34.882 | 35.242 | 36.647 | 1.00  8.82 |
| ATOM | 1154 | N   | ASN | 149 | 37.534 | 31.579 | 41.125 | 1.00 10.80 |
| ATOM | 1155 | CA  | ASN | 149 | 37.626 | 30.805 | 42.345 | 1.00 13.35 |
| ATOM | 1156 | C   | ASN | 149 | 36.409 | 31.157 | 43.205 | 1.00 14.47 |
| ATOM | 1157 | O   | ASN | 149 | 36.099 | 32.320 | 43.387 | 1.00 18.17 |
| ATOM | 1158 | CB  | ASN | 149 | 38.890 | 31.093 | 43.184 | 1.00 12.67 |
| ATOM | 1159 | CG  | ASN | 149 | 40.148 | 30.822 | 42.424 | 1.00 20.21 |
| ATOM | 1160 | OD1 | ASN | 149 | 40.993 | 31.713 | 42.281 | 1.00 56.34 |
| ATOM | 1161 | ND2 | ASN | 149 | 40.210 | 29.641 | 41.818 | 1.00 16.44 |
| ATOM | 1162 | N   | VAL | 150 | 35.773 | 30.144 | 43.741 | 1.00 14.65 |
| ATOM | 1163 | CA  | VAL | 150 | 34.588 | 30.262 | 44.552 | 1.00 12.92 |
| ATOM | 1164 | C   | VAL | 150 | 34.910 | 29.806 | 45.943 | 1.00 16.30 |
| ATOM | 1165 | O   | VAL | 150 | 35.257 | 28.665 | 46.147 | 1.00 17.83 |
| ATOM | 1166 | CB  | VAL | 150 | 33.482 | 29.382 | 43.914 | 1.00 15.22 |
| ATOM | 1167 | CG1 | VAL | 150 | 32.252 | 29.297 | 44.765 | 1.00 14.09 |
| ATOM | 1168 | CG2 | VAL | 150 | 33.172 | 29.791 | 42.464 | 1.00 10.94 |
| ATOM | 1169 | N   | TYR | 151 | 34.796 | 30.716 | 46.900 | 1.00 17.64 |
| ATOM | 1170 | CA  | TYR | 151 | 35.139 | 30.440 | 48.275 | 1.00 18.31 |
| ATOM | 1171 | C   | TYR | 151 | 34.003 | 29.917 | 49.117 | 1.00 24.35 |
| ATOM | 1172 | O   | TYR | 151 | 32.963 | 30.536 | 49.239 | 1.00 20.83 |
| ATOM | 1173 | CB  | TYR | 151 | 35.793 | 31.681 | 48.920 | 1.00 20.15 |
| ATOM | 1174 | CG  | TYR | 151 | 37.025 | 32.033 | 48.141 | 1.00 25.86 |
| ATOM | 1175 | CD1 | TYR | 151 | 37.003 | 32.989 | 47.127 | 1.00 26.00 |
| ATOM | 1176 | CD2 | TYR | 151 | 38.200 | 31.315 | 48.355 | 1.00 28.66 |
| ATOM | 1177 | CE1 | TYR | 151 | 38.151 | 33.234 | 46.369 | 1.00 33.73 |
| ATOM | 1178 | CE2 | TYR | 151 | 39.360 | 31.550 | 47.619 | 1.00 29.01 |
| ATOM | 1179 | CZ  | TYR | 151 | 39.325 | 32.512 | 46.618 | 1.00 29.55 |
| ATOM | 1180 | OH  | TYR | 151 | 40.449 | 32.737 | 45.877 | 1.00 38.69 |
| ATOM | 1181 | N   | ILE | 152 | 34.250 | 28.791 | 49.753 | 1.00 17.71 |
| ATOM | 1182 | CA  | ILE | 152 | 33.255 | 28.159 | 50.572 | 1.00 14.12 |
| ATOM | 1183 | C   | ILE | 152 | 33.619 | 28.056 | 52.000 | 1.00 18.51 |
| ATOM | 1184 | O   | ILE | 152 | 34.728 | 27.703 | 52.336 | 1.00 22.05 |

*FIG. 5AC*

| | | | | | | | |
|---|---|---|---|---|---|---|---|
| ATOM | 1185 CB | ILE | 152 | 32.979 | 26.776 | 50.060 | 1.00 16.66 |
| ATOM | 1186 CG1 | ILE | 152 | 32.431 | 26.875 | 48.638 | 1.00 11.30 |
| ATOM | 1187 CG2 | ILE | 152 | 32.017 | 26.078 | 51.021 | 1.00 17.96 |
| ATOM | 1188 CD1 | ILE | 152 | 32.377 | 25.559 | 47.949 | 1.00 13.48 |
| ATOM | 1189 N | MSE | 153 | 32.623 | 28.278 | 52.841 | 1.00 17.41 |
| ATOM | 1190 AC | MSE | 153 | 32.789 | 28.162 | 54.269 | 1.00 22.61 |
| ATOM | 1191 C | MSE | 153 | 31.534 | 27.648 | 54.916 | 1.00 27.31 |
| ATOM | 1192 O | MSE | 153 | 30.433 | 27.831 | 54.396 | 1.00 20.50 |
| ATOM | 1193 CB | MSE | 153 | 33.145 | 29.490 | 54.855 | 1.00 19.11 |
| ATOM | 1194 CG | MSE | 153 | 34.010 | 30.302 | 53.957 | 1.00 100.00 |
| ATOM | 1195 SE | MSE | 153 | 34.060 | 32.117 | 54.524 | 1.00 100.00 |
| ATOM | 1196 CE | MSE | 153 | 33.463 | 31.798 | 56.330 | 1.00 30.27 |
| ATOM | 1197 N | ALA | 154 | 31.733 | 26.983 | 56.053 | 1.00 22.29 |
| ATOM | 1198 CA | ALA | 154 | 30.669 | 26.389 | 56.796 | 1.00 22.66 |
| ATOM | 1199 C | ALA | 154 | 29.820 | 27.401 | 57.552 | 1.00 29.00 |
| ATOM | 1200 O | ALA | 154 | 30.274 | 28.457 | 57.960 | 1.00 27.02 |
| ATOM | 1201 CB | ALA | 154 | 31.224 | 25.336 | 57.744 | 1.00 19.78 |
| ATOM | 1202 N | ASP | 155 | 28.566 | 27.063 | 57.726 | 1.00 29.48 |
| ATOM | 1203 CA | ASP | 155 | 27.669 | 27.887 | 58.484 | 1.00 32.18 |
| ATOM | 1204 C | ASP | 155 | 26.976 | 27.019 | 59.511 | 1.00 44.51 |
| ATOM | 1205 O | ASP | 155 | 25.898 | 26.492 | 59.274 | 1.00 39.56 |
| ATOM | 1206 CB | ASP | 155 | 26.659 | 28.617 | 57.597 | 1.00 31.70 |
| ATOM | 1207 CG | ASP | 155 | 26.140 | 29.851 | 58.247 | 1.00 49.89 |
| ATOM | 1208 OD1 | ASP | 155 | 26.595 | 30.297 | 59.277 | 1.00 46.67 |
| ATOM | 1209 OD2 | ASP | 155 | 25.187 | 30.422 | 57.565 | 1.00 76.07 |
| ATOM | 1210 N | LYS | 156 | 27.646 | 26.816 | 60.629 | 1.00 46.37 |
| ATOM | 1211 CA | LYS | 156 | 27.116 | 25.954 | 61.654 | 1.00 53.23 |
| ATOM | 1212 C | LYS | 156 | 25.750 | 26.369 | 62.224 | 1.00 65.62 |
| ATOM | 1213 O | LYS | 156 | 25.012 | 25.520 | 62.703 | 1.00 65.54 |
| ATOM | 1214 CB | LYS | 156 | 28.147 | 25.612 | 62.725 | 1.00 59.51 |
| ATOM | 1215 N | GLN | 157 | 25.398 | 27.655 | 62.138 | 1.00 68.32 |
| ATOM | 1216 CA | GLN | 157 | 24.119 | 28.135 | 62.670 | 1.00 73.00 |
| ATOM | 1217 C | GLN | 157 | 22.891 | 27.767 | 61.817 | 1.00 87.53 |
| ATOM | 1218 O | GLN | 157 | 21.778 | 27.547 | 62.325 | 1.00 96.16 |
| ATOM | 1219 N | LYS | 158 | 23.095 | 27.725 | 60.506 | 1.00 72.49 |
| ATOM | 1220 CA | LYS | 158 | 22.040 | 27.386 | 59.593 | 1.00 66.19 |
| ATOM | 1221 C | LYS | 158 | 22.235 | 25.985 | 59.040 | 1.00 58.21 |
| ATOM | 1222 O | LYS | 158 | 21.447 | 25.524 | 58.226 | 1.00 59.85 |
| ATOM | 1223 N | ASN | 159 | 23.303 | 25.294 | 59.502 | 1.00 40.00 |
| ATOM | 1224 CA | ASN | 159 | 23.582 | 23.944 | 59.012 | 1.00 36.67 |
| ATOM | 1225 C | ASN | 159 | 23.755 | 24.002 | 57.500 | 1.00 34.11 |

*FIG. 5AD*

| | | | | | | | |
|---|---|---|---|---|---|---|---|
| ATOM | 1226 | CO | ASN | 159 | 23.223 | 23.167 | 56.754 | 1.00 31.69 |
| ATOM | 1227 | CB | ASN | 159 | 22.431 | 22.952 | 59.367 | 1.00 46.42 |
| ATOM | 1228 | CG | ASN | 159 | 22.842 | 21.485 | 59.428 | 1.00 80.46 |
| ATOM | 1229 | OD1 | ASN | 159 | 23.850 | 21.121 | 60.054 | 1.00 100.00 |
| ATOM | 1230 | ND2 | ASN | 159 | 22.003 | 20.620 | 58.854 | 1.00 58.09 |
| ATOM | 1231 | N | GLY | 160 | 24.474 | 25.044 | 57.062 | 1.00 22.34 |
| ATOM | 1232 | CA | GLY | 160 | 24.686 | 25.247 | 55.663 | 1.00 17.58 |
| ATOM | 1233 | C | GLY | 160 | 26.055 | 25.791 | 55.433 | 1.00 26.75 |
| ATOM | 1234 | O | GLY | 160 | 26.960 | 25.664 | 56.271 | 1.00 25.57 |
| ATOM | 1235 | N | ILE | 161 | 26.200 | 26.395 | 54.277 | 1.00 23.28 |
| ATOM | 1236 | CA | ILE | 161 | 27.442 | 26.975 | 53.909 | 1.00 16.45 |
| ATOM | 1237 | C | ILE | 161 | 27.200 | 28.354 | 53.395 | 1.00 15.77 |
| ATOM | 1238 | O | ILE | 161 | 26.118 | 28.680 | 52.962 | 1.00 15.95 |
| ATOM | 1239 | CB | ILE | 161 | 28.129 | 26.117 | 52.864 | 1.00 19.27 |
| ATOM | 1240 | CG1 | ILE | 161 | 27.237 | 26.016 | 51.619 | 1.00 18.53 |
| ATOM | 1241 | CG2 | ILE | 161 | 28.351 | 24.735 | 53.445 | 1.00 21.96 |
| ATOM | 1242 | CD1 | ILE | 161 | 28.009 | 25.614 | 50.350 | 1.00 14.44 |
| ATOM | 1243 | N | LYS | 162 | 28.226 | 29.169 | 53.471 | 1.00 17.86 |
| ATOM | 1244 | CA | LYS | 162 | 28.187 | 30.508 | 52.948 | 1.00 14.42 |
| ATOM | 1245 | C | LYS | 162 | 29.216 | 30.524 | 51.857 | 1.00 17.73 |
| ATOM | 1246 | O | LYS | 162 | 30.249 | 29.875 | 51.991 | 1.00 19.16 |
| ATOM | 1247 | CB | LYS | 162 | 28.480 | 31.540 | 54.055 | 1.00 18.15 |
| ATOM | 1248 | CG | LYS | 162 | 27.221 | 31.963 | 54.796 | 1.00 42.08 |
| ATOM | 1249 | CD | LYS | 162 | 27.493 | 32.787 | 56.039 | 1.00 70.42 |
| ATOM | 1250 | N | VAL | 163 | 28.911 | 31.176 | 50.759 | 1.00 13.74 |
| ATOM | 1251 | CA | VAL | 163 | 29.798 | 31.201 | 49.629 | 1.00 11.95 |
| ATOM | 1252 | C | VAL | 163 | 29.928 | 32.610 | 49.103 | 1.00 19.30 |
| ATOM | 1253 | O | VAL | 163 | 28.944 | 33.318 | 48.983 | 1.00 19.84 |
| ATOM | 1254 | CB | VAL | 163 | 29.249 | 30.268 | 48.532 | 1.00 15.89 |
| ATOM | 1255 | CG1 | VAL | 163 | 30.105 | 30.277 | 47.261 | 1.00 12.09 |
| ATOM | 1256 | CG2 | VAL | 163 | 29.029 | 28.852 | 49.077 | 1.00 15.86 |
| ATOM | 1257 | N | ASN | 164 | 31.146 | 32.999 | 48.733 | 1.00 14.03 |
| ATOM | 1258 | CA | ASN | 164 | 31.382 | 34.310 | 48.195 | 1.00 15.58 |
| ATOM | 1259 | C | ASN | 164 | 32.396 | 34.271 | 47.050 | 1.00 20.08 |
| ATOM | 1260 | O | ASN | 164 | 33.268 | 33.386 | 46.988 | 1.00 23.49 |
| ATOM | 1261 | CB | ASN | 164 | 31.732 | 35.325 | 49.308 | 1.00 20.52 |
| ATOM | 1262 | CG | ASN | 164 | 33.196 | 35.697 | 49.330 | 1.00 89.21 |
| ATOM | 1263 | OD1 | ASN | 164 | 34.020 | 34.987 | 49.929 | 1.00 100.00 |
| ATOM | 1264 | ND2 | ASN | 164 | 33.515 | 36.831 | 48.700 | 1.00 91.46 |
| ATOM | 1265 | N | PHE | 165 | 32.244 | 35.207 | 46.109 | 1.00 17.37 |
| ATOM | 1266 | CA | PHE | 165 | 33.133 | 35.301 | 44.953 | 1.00 10.86 |

*FIG. 5AE*

| | | | | | | | |
|---|---|---|---|---|---|---|---|
| ATOM | 1267 | C | PHE | 165 | 32.751 | 36.445 | 44.071 | 1.00 15.53 |
| ATOM | 1268 | O | PHE | 165 | 31.686 | 37.020 | 44.251 | 1.00 17.16 |
| ATOM | 1269 | CB | PHE | 165 | 33.207 | 33.960 | 44.187 | 1.00 12.86 |
| ATOM | 1270 | CG | PHE | 165 | 31.862 | 33.486 | 43.622 | 1.00 14.35 |
| ATOM | 1271 | CD1 | PHE | 165 | 31.510 | 33.749 | 42.293 | 1.00 14.61 |
| ATOM | 1272 | CD2 | PHE | 165 | 30.978 | 32.757 | 44.413 | 1.00 13.56 |
| ATOM | 1273 | CE1 | PHE | 165 | 30.300 | 33.297 | 41.759 | 1.00 22.67 |
| ATOM | 1274 | CE2 | PHE | 165 | 29.774 | 32.282 | 43.893 | 1.00 15.78 |
| ATOM | 1275 | CZ | PHE | 165 | 29.426 | 32.572 | 42.573 | 1.00 16.20 |
| ATOM | 1276 | N | LYS | 166 | 33.641 | 36.799 | 43.132 | 1.00 10.79 |
| ATOM | 1277 | CA | LYS | 166 | 33.417 | 37.864 | 42.162 | 1.00 10.74 |
| ATOM | 1278 | C | LYS | 166 | 33.603 | 37.344 | 40.774 | 1.00 15.95 |
| ATOM | 1279 | O | LYS | 166 | 34.602 | 36.727 | 40.470 | 1.00 22.80 |
| ATOM | 1280 | CB | LYS | 166 | 34.387 | 39.055 | 42.249 | 1.00 16.61 |
| ATOM | 1281 | CG | LYS | 166 | 34.573 | 39.688 | 43.573 | 1.00 18.11 |
| ATOM | 1282 | CD | LYS | 166 | 35.540 | 40.875 | 43.454 | 1.00 32.56 |
| ATOM | 1283 | CE | LYS | 166 | 35.272 | 41.966 | 44.476 | 1.00 48.19 |
| ATOM | 1284 | NZ | LYS | 166 | 34.823 | 41.435 | 45.782 | 1.00 85.81 |
| ATOM | 1285 | N | ILE | 167 | 32.703 | 37.704 | 39.911 | 1.00 9.75 |
| ATOM | 1286 | CA | ILE | 167 | 32.768 | 37.340 | 38.558 | 1.00 9.35 |
| ATOM | 1287 | C | ILE | 167 | 33.203 | 38.542 | 37.823 | 1.00 14.36 |
| ATOM | 1288 | O | ILE | 167 | 32.811 | 39.640 | 38.170 | 1.00 16.22 |
| ATOM | 1289 | CB | ILE | 167 | 31.379 | 36.929 | 38.005 | 1.00 13.16 |
| ATOM | 1290 | CG1 | ILE | 167 | 30.909 | 35.624 | 38.669 | 1.00 13.02 |
| ATOM | 1291 | CG2 | ILE | 167 | 31.423 | 36.786 | 36.472 | 1.00 7.91 |
| ATOM | 1292 | CD1 | ILE | 167 | 31.773 | 34.415 | 38.344 | 1.00 19.57 |
| ATOM | 1293 | N | ARG | 168 | 34.005 | 38.299 | 36.815 | 1.00 12.19 |
| ATOM | 1294 | CA | ARG | 168 | 34.500 | 39.308 | 35.945 | 1.00 15.07 |
| ATOM | 1295 | C | ARG | 168 | 33.948 | 39.122 | 34.528 | 1.00 16.64 |
| ATOM | 1296 | O | ARG | 168 | 34.278 | 38.156 | 33.836 | 1.00 17.70 |
| ATOM | 1297 | CB | ARG | 168 | 36.024 | 39.287 | 35.944 | 1.00 16.54 |
| ATOM | 1298 | CG | ARG | 168 | 36.580 | 39.632 | 37.321 | 1.00 25.54 |
| ATOM | 1299 | CD | ARG | 168 | 37.894 | 38.910 | 37.601 | 1.00 63.52 |
| ATOM | 1300 | NE | ARG | 168 | 38.380 | 38.191 | 36.416 | 1.00 73.52 |
| ATOM | 1301 | CZ | ARG | 168 | 38.764 | 36.926 | 36.416 | 1.00 67.92 |
| ATOM | 1302 | NH1 | ARG | 168 | 38.795 | 36.192 | 37.527 | 1.00 57.44 |
| ATOM | 1303 | NH2 | ARG | 168 | 39.192 | 36.375 | 35.271 | 1.00 59.15 |
| ATOM | 1304 | N | HIS | 169 | 33.090 | 40.064 | 34.098 | 1.00 14.88 |
| ATOM | 1305 | CA | HIS | 169 | 32.505 | 40.025 | 32.758 | 1.00 13.24 |
| ATOM | 1306 | C | HIS | 169 | 33.214 | 41.001 | 31.839 | 1.00 12.64 |
| ATOM | 1307 | O | HIS | 169 | 33.306 | 42.203 | 32.121 | 1.00 14.99 |

*FIG. 5AF*

| | | | | | | | |
|---|---|---|---|---|---|---|---|
| ATOM | 1308 | CB | HIS | 169 | 30.970 | 40.374 | 32.760 | 1.00 10.46 |
| ATOM | 1309 | CG | HIS | 169 | 30.097 | 39.474 | 33.573 | 1.00 6.54 |
| ATOM | 1310 | ND1 | HIS | 169 | 29.724 | 38.246 | 33.111 | 1.00 12.63 |
| ATOM | 1311 | CD2 | HIS | 169 | 29.474 | 39.695 | 34.764 | 1.00 10.21 |
| ATOM | 1312 | CE1 | HIS | 169 | 28.892 | 37.718 | 34.031 | 1.00 10.53 |
| ATOM | 1313 | NE2 | HIS | 169 | 28.734 | 38.566 | 35.063 | 1.00 11.84 |
| ATOM | 1314 | N | ASN | 170 | 33.691 | 40.513 | 30.737 | 1.00 10.66 |
| ATOM | 1315 | CA | ASN | 170 | 34.349 | 41.368 | 29.812 | 1.00 15.87 |
| ATOM | 1316 | C | ASN | 170 | 33.356 | 42.224 | 29.067 | 1.00 25.06 |
| ATOM | 1317 | O | ASN | 170 | 32.386 | 41.701 | 28.537 | 1.00 16.60 |
| ATOM | 1318 | CB | ASN | 170 | 35.110 | 40.550 | 28.755 | 1.00 19.60 |
| ATOM | 1319 | CG | ASN | 170 | 36.245 | 39.717 | 29.312 | 1.00 18.70 |
| ATOM | 1320 | OD1 | ASN | 170 | 36.702 | 38.752 | 28.684 | 1.00 48.29 |
| ATOM | 1321 | ND2 | ASN | 170 | 36.695 | 40.073 | 30.480 | 1.00 19.13 |
| ATOM | 1322 | N | ILE | 171 | 33.662 | 43.527 | 28.947 | 1.00 18.75 |
| ATOM | 1323 | CA | ILE | 171 | 32.848 | 44.460 | 28.168 | 1.00 16.74 |
| ATOM | 1324 | C | ILE | 171 | 33.459 | 44.638 | 26.791 | 1.00 19.51 |
| ATOM | 1325 | O | ILE | 171 | 34.643 | 44.596 | 26.642 | 1.00 21.06 |
| ATOM | 1326 | CB | ILE | 171 | 32.713 | 45.804 | 28.842 | 1.00 20.46 |
| ATOM | 1327 | CG1 | ILE | 171 | 32.089 | 45.617 | 30.193 | 1.00 24.79 |
| ATOM | 1328 | CG2 | ILE | 171 | 31.852 | 46.727 | 27.997 | 1.00 19.03 |
| ATOM | 1329 | CD1 | ILE | 171 | 32.630 | 46.599 | 31.229 | 1.00 41.65 |
| ATOM | 1330 | N | GLU | 172 | 32.632 | 44.818 | 25.804 | 1.00 16.54 |
| ATOM | 1331 | CA | GLU | 172 | 33.034 | 44.933 | 24.420 | 1.00 17.00 |
| ATOM | 1332 | C | GLU | 172 | 34.110 | 45.967 | 24.147 | 1.00 26.80 |
| ATOM | 1333 | O | GLU | 172 | 34.776 | 45.898 | 23.125 | 1.00 29.20 |
| ATOM | 1334 | CB | GLU | 172 | 31.813 | 45.165 | 23.509 | 1.00 22.46 |
| ATOM | 1335 | CG | GLU | 172 | 31.122 | 46.531 | 23.786 | 1.00 58.53 |
| ATOM | 1336 | CD | GLU | 172 | 29.871 | 46.783 | 22.933 | 1.00 100.00 |
| ATOM | 1337 | OE1 | GLU | 172 | 29.415 | 45.970 | 22.156 | 1.00 100.00 |
| ATOM | 1338 | OE2 | GLU | 172 | 29.370 | 47.982 | 23.149 | 1.00 100.00 |
| ATOM | 1339 | N | ASP | 173 | 34.277 | 46.934 | 25.034 | 1.00 24.41 |
| ATOM | 1340 | CA | ASP | 173 | 35.292 | 47.978 | 24.852 | 1.00 25.03 |
| ATOM | 1341 | C | ASP | 173 | 36.651 | 47.624 | 25.455 | 1.00 33.40 |
| ATOM | 1342 | O | ASP | 173 | 37.561 | 48.451 | 25.518 | 1.00 30.42 |
| ATOM | 1343 | CB | ASP | 173 | 34.822 | 49.319 | 25.401 | 1.00 23.30 |
| ATOM | 1344 | CG | ASP | 173 | 34.743 | 49.358 | 26.912 | 1.00 32.47 |
| ATOM | 1345 | OD1 | ASP | 173 | 34.406 | 50.355 | 27.513 | 1.00 37.58 |
| ATOM | 1346 | OD2 | ASP | 173 | 34.949 | 48.196 | 27.504 | 1.00 49.22 |
| ATOM | 1347 | N | GLY | 174 | 36.766 | 46.410 | 25.956 | 1.00 23.87 |
| ATOM | 1348 | CA | GLY | 174 | 38.019 | 45.994 | 26.537 | 1.00 21.30 |

*FIG. 5AG*

| | | | | | | | |
|---|---|---|---|---|---|---|---|
| ATOM | 1349 C | GLY | 174 | 38.012 | 46.090 | 28.044 | 1.00 19.99 |
| ATOM | 1350 O | GLY | 174 | 38.927 | 45.585 | 28.709 | 1.00 20.45 |
| ATOM | 1351 N | SER | 175 | 36.972 | 46.767 | 28.598 | 1.00 13.88 |
| ATOM | 1352 CA | SER | 175 | 36.898 | 46.931 | 30.034 | 1.00 8.70 |
| ATOM | 1353 C | SER | 175 | 36.296 | 45.728 | 30.765 | 1.00 17.30 |
| ATOM | 1354 O | SER | 175 | 36.136 | 44.655 | 30.175 | 1.00 18.77 |
| ATOM | 1355 CB | SER | 175 | 36.288 | 48.235 | 30.450 | 1.00 14.07 |
| ATOM | 1356 OG | SER | 175 | 36.360 | 48.316 | 31.865 | 1.00 24.79 |
| ATOM | 1357 N | VAL | 176 | 35.963 | 45.912 | 32.051 | 1.00 13.74 |
| ATOM | 1358 CA | VAL | 176 | 35.415 | 44.826 | 32.864 | 1.00 16.46 |
| ATOM | 1359 C | VAL | 176 | 34.191 | 45.204 | 33.703 | 1.00 22.46 |
| ATOM | 1360 O | VAL | 176 | 34.159 | 46.254 | 34.334 | 1.00 21.31 |
| ATOM | 1361 CB | VAL | 176 | 36.477 | 44.285 | 33.818 | 1.00 24.43 |
| ATOM | 1362 CG1 | VAL | 176 | 35.847 | 43.344 | 34.827 | 1.00 27.45 |
| ATOM | 1363 CG2 | VAL | 176 | 37.532 | 43.536 | 33.035 | 1.00 25.65 |
| ATOM | 1364 N | GLN | 177 | 33.234 | 44.269 | 33.787 | 1.00 15.47 |
| ATOM | 1365 CA | GLN | 177 | 32.048 | 44.430 | 34.647 | 1.00 15.40 |
| ATOM | 1366 C | GLN | 177 | 32.102 | 43.457 | 35.813 | 1.00 10.60 |
| ATOM | 1367 O | GLN | 177 | 32.027 | 42.243 | 35.634 | 1.00 13.65 |
| ATOM | 1368 CB | GLN | 177 | 30.709 | 44.283 | 33.872 | 1.00 15.57 |
| ATOM | 1369 CG | GLN | 177 | 29.468 | 44.294 | 34.828 | 1.00 19.13 |
| ATOM | 1370 CD | GLN | 177 | 29.108 | 45.678 | 35.361 | 1.00 14.91 |
| ATOM | 1371 OE1 | GLN | 177 | 28.759 | 46.588 | 34.574 | 1.00 20.17 |
| ATOM | 1372 NE2 | GLN | 177 | 29.128 | 45.821 | 36.690 | 1.00 17.28 |
| ATOM | 1373 N | LEU | 178 | 32.227 | 43.993 | 37.018 | 1.00 8.17 |
| ATOM | 1374 CA | LEU | 178 | 32.313 | 43.180 | 38.181 | 1.00 16.66 |
| ATOM | 1375 C | LEU | 178 | 30.954 | 42.786 | 38.712 | 1.00 20.93 |
| ATOM | 1376 O | LEU | 178 | 30.033 | 43.608 | 38.753 | 1.00 14.66 |
| ATOM | 1377 CB | LEU | 178 | 33.089 | 43.896 | 39.293 | 1.00 20.63 |
| ATOM | 1378 CG | LEU | 178 | 34.286 | 43.110 | 39.815 | 1.00 39.28 |
| ATOM | 1379 CD1 | LEU | 178 | 33.831 | 42.087 | 40.852 | 1.00 45.14 |
| ATOM | 1380 CD2 | LEU | 178 | 35.018 | 42.426 | 38.648 | 1.00 39.52 |
| ATOM | 1381 N | ALA | 179 | 30.869 | 41.550 | 39.171 | 1.00 16.72 |
| ATOM | 1382 CA | ALA | 179 | 29.652 | 41.033 | 39.754 | 1.00 15.55 |
| ATOM | 1383 C | ALA | 179 | 29.932 | 40.277 | 41.040 | 1.00 15.70 |
| ATOM | 1384 O | ALA | 179 | 30.337 | 39.119 | 41.028 | 1.00 15.91 |
| ATOM | 1385 CB | ALA | 179 | 28.853 | 40.197 | 38.731 | 1.00 14.08 |
| ATOM | 1386 N | ASP | 180 | 29.694 | 40.946 | 42.155 | 1.00 8.88 |
| ATOM | 1387 CA | ASP | 180 | 29.897 | 40.407 | 43.480 | 1.00 7.18 |
| ATOM | 1388 C | ASP | 180 | 28.802 | 39.460 | 43.891 | 1.00 17.07 |
| ATOM | 1389 O | ASP | 180 | 27.651 | 39.844 | 43.987 | 1.00 18.22 |

*FIG. 5AH*

| | | | | | | | |
|---|---|---|---|---|---|---|---|
| ATOM | 1390 | CB  | ASP | 180 | 29.934 | 41.509 | 44.509 | 1.00 13.06 |
| ATOM | 1391 | CG  | ASP | 180 | 31.285 | 41.902 | 44.935 | 1.00 46.28 |
| ATOM | 1392 | OD1 | ASP | 180 | 31.981 | 41.206 | 45.655 | 1.00 60.46 |
| ATOM | 1393 | OD2 | ASP | 180 | 31.574 | 43.121 | 44.560 | 1.00 46.61 |
| ATOM | 1394 | N   | HIS | 181 | 29.173 | 38.242 | 44.197 | 1.00 14.51 |
| ATOM | 1395 | CA  | HIS | 181 | 28.213 | 37.223 | 44.575 | 1.00 10.49 |
| ATOM | 1396 | C   | HIS | 181 | 28.218 | 36.897 | 46.049 | 1.00 14.28 |
| ATOM | 1397 | O   | HIS | 181 | 29.255 | 36.580 | 46.607 | 1.00 17.40 |
| ATOM | 1398 | CB  | HIS | 181 | 28.450 | 35.915 | 43.769 | 1.00  9.89 |
| ATOM | 1399 | CG  | HIS | 181 | 28.077 | 35.972 | 42.328 | 1.00 10.38 |
| ATOM | 1400 | ND1 | HIS | 181 | 28.606 | 36.926 | 41.455 | 1.00 12.24 |
| ATOM | 1401 | CD2 | HIS | 181 | 27.279 | 35.146 | 41.606 | 1.00 10.42 |
| ATOM | 1402 | CE1 | HIS | 181 | 28.093 | 36.678 | 40.269 | 1.00  9.97 |
| ATOM | 1403 | NE2 | HIS | 181 | 27.314 | 35.594 | 40.316 | 1.00  9.38 |
| ATOM | 1404 | N   | TYR | 182 | 27.029 | 36.897 | 46.668 | 1.00 10.40 |
| ATOM | 1405 | CA  | TYR | 182 | 26.848 | 36.518 | 48.062 | 1.00 13.86 |
| ATOM | 1406 | C   | TYR | 182 | 25.871 | 35.393 | 48.089 | 1.00 20.61 |
| ATOM | 1407 | O   | TYR | 182 | 24.819 | 35.520 | 47.532 | 1.00 16.35 |
| ATOM | 1408 | CB  | TYR | 182 | 26.359 | 37.664 | 48.934 | 1.00 21.12 |
| ATOM | 1409 | CG  | TYR | 182 | 27.421 | 38.693 | 49.062 | 1.00 34.16 |
| ATOM | 1410 | CD1 | TYR | 182 | 27.521 | 39.715 | 48.120 | 1.00 46.06 |
| ATOM | 1411 | CD2 | TYR | 182 | 28.389 | 38.616 | 50.064 | 1.00 38.56 |
| ATOM | 1412 | CE1 | TYR | 182 | 28.532 | 40.674 | 48.197 | 1.00 57.53 |
| ATOM | 1413 | CE2 | TYR | 182 | 29.418 | 39.559 | 50.147 | 1.00 40.76 |
| ATOM | 1414 | CZ  | TYR | 182 | 29.480 | 40.594 | 49.216 | 1.00 54.61 |
| ATOM | 1415 | OH  | TYR | 182 | 30.461 | 41.534 | 49.308 | 1.00 61.92 |
| ATOM | 1416 | N   | GLN | 183 | 26.246 | 34.277 | 48.686 | 1.00 17.63 |
| ATOM | 1417 | CA  | GLN | 183 | 25.410 | 33.104 | 48.583 | 1.00 16.37 |
| ATOM | 1418 | C   | GLN | 183 | 25.289 | 32.311 | 49.863 | 1.00 21.39 |
| ATOM | 1419 | O   | GLN | 183 | 26.260 | 32.174 | 50.623 | 1.00 19.86 |
| ATOM | 1420 | CB  | GLN | 183 | 25.984 | 32.219 | 47.422 | 1.00 13.33 |
| ATOM | 1421 | CG  | GLN | 183 | 25.651 | 30.688 | 47.457 | 1.00 17.38 |
| ATOM | 1422 | CD  | GLN | 183 | 26.411 | 29.884 | 46.389 | 1.00 17.27 |
| ATOM | 1423 | OE1 | GLN | 183 | 26.975 | 30.454 | 45.456 | 1.00 13.80 |
| ATOM | 1424 | NE2 | GLN | 183 | 26.361 | 28.553 | 46.473 | 1.00 13.94 |
| ATOM | 1425 | N   | GLN | 184 | 24.080 | 31.739 | 50.055 | 1.00 19.74 |
| ATOM | 1426 | CA  | GLN | 184 | 23.760 | 30.829 | 51.168 | 1.00 16.55 |
| ATOM | 1427 | C   | GLN | 184 | 23.033 | 29.582 | 50.658 | 1.00 13.60 |
| ATOM | 1428 | O   | GLN | 184 | 22.219 | 29.640 | 49.747 | 1.00 18.01 |
| ATOM | 1429 | CB  | GLN | 184 | 22.949 | 31.444 | 52.330 | 1.00 20.11 |
| ATOM | 1430 | CG  | GLN | 184 | 23.364 | 32.855 | 52.768 | 1.00 74.84 |

*FIG. 5AI*

| | | | | | | | |
|---|---|---|---|---|---|---|---|
| ATOM | 1431 | CD | GLN | 184 | 22.312 | 33.517 | 53.657 | 1.00 100.00 |
| ATOM | 1432 | OE1 | GLN | 184 | 21.159 | 33.054 | 53.752 | 1.00 97.99 |
| ATOM | 1433 | NE2 | GLN | 184 | 22.689 | 34.625 | 54.286 | 1.00 100.00 |
| ATOM | 1434 | N | ASN | 185 | 23.418 | 28.446 | 51.207 | 1.00 14.76 |
| ATOM | 1435 | CA | ASN | 185 | 22.831 | 27.155 | 50.887 | 1.00 13.86 |
| ATOM | 1436 | C | ASN | 185 | 22.421 | 26.463 | 52.166 | 1.00 16.06 |
| ATOM | 1437 | O | ASN | 185 | 23.176 | 26.402 | 53.172 | 1.00 17.39 |
| ATOM | 1438 | CB | ASN | 185 | 23.761 | 26.212 | 50.119 | 1.00 15.20 |
| ATOM | 1439 | CG | ASN | 185 | 24.110 | 26.696 | 48.748 | 1.00 12.75 |
| ATOM | 1440 | OD1 | ASN | 185 | 24.704 | 27.758 | 48.592 | 1.00 22.56 |
| ATOM | 1441 | ND2 | ASN | 185 | 23.830 | 25.868 | 47.763 | 1.00 17.70 |
| ATOM | 1442 | N | THR | 186 | 21.227 | 25.941 | 52.139 | 1.00 18.01 |
| ATOM | 1443 | CA | THR | 186 | 20.707 | 25.227 | 53.288 | 1.00 17.40 |
| ATOM | 1444 | C | THR | 186 | 19.976 | 24.010 | 52.824 | 1.00 23.63 |
| ATOM | 1445 | O | THR | 186 | 19.389 | 23.991 | 51.730 | 1.00 24.57 |
| ATOM | 1446 | CB | THR | 186 | 19.856 | 26.100 | 54.206 | 1.00 28.82 |
| ATOM | 1447 | OG1 | THR | 186 | 18.874 | 26.752 | 53.446 | 1.00 35.65 |
| ATOM | 1448 | CG2 | THR | 186 | 20.753 | 27.121 | 54.903 | 1.00 28.86 |
| ATOM | 1449 | N | PRO | 187 | 20.101 | 22.951 | 53.620 | 1.00 22.40 |
| ATOM | 1450 | CA | PRO | 187 | 19.504 | 21.683 | 53.269 | 1.00 20.28 |
| ATOM | 1451 | C | PRO | 187 | 17.988 | 21.757 | 53.288 | 1.00 22.41 |
| ATOM | 1452 | O | PRO | 187 | 17.390 | 22.518 | 54.071 | 1.00 25.07 |
| ATOM | 1453 | CB | PRO | 187 | 19.977 | 20.682 | 54.337 | 1.00 19.79 |
| ATOM | 1454 | CG | PRO | 187 | 20.840 | 21.449 | 55.338 | 1.00 26.98 |
| ATOM | 1455 | CD | PRO | 187 | 20.786 | 22.918 | 54.949 | 1.00 22.04 |
| ATOM | 1456 | N | ILE | 188 | 17.382 | 20.957 | 52.453 | 1.00 18.77 |
| ATOM | 1457 | CA | ILE | 188 | 15.907 | 20.855 | 52.407 | 1.00 20.12 |
| ATOM | 1458 | C | ILE | 188 | 15.470 | 19.766 | 53.389 | 1.00 31.58 |
| ATOM | 1459 | O | ILE | 188 | 14.596 | 19.966 | 54.202 | 1.00 38.58 |
| ATOM | 1460 | CB | ILE | 188 | 15.385 | 20.574 | 50.991 | 1.00 21.52 |
| ATOM | 1461 | CG1 | ILE | 188 | 15.555 | 21.775 | 50.102 | 1.00 16.10 |
| ATOM | 1462 | CG2 | ILE | 188 | 13.916 | 20.141 | 50.981 | 1.00 28.85 |
| ATOM | 1463 | CD1 | ILE | 188 | 15.139 | 21.471 | 48.660 | 1.00 15.31 |
| ATOM | 1464 | N | GLY | 189 | 16.142 | 18.618 | 53.352 | 1.00 32.39 |
| ATOM | 1465 | CA | GLY | 189 | 15.833 | 17.531 | 54.283 | 1.00 32.94 |
| ATOM | 1466 | C | GLY | 189 | 16.339 | 17.817 | 55.702 | 1.00 40.20 |
| ATOM | 1467 | O | GLY | 189 | 17.016 | 18.810 | 55.967 | 1.00 35.57 |
| ATOM | 1468 | N | ASP | 190 | 16.003 | 19.928 | 56.617 | 1.00 49.41 |
| ATOM | 1469 | CA | ASP | 190 | 16.392 | 17.047 | 58.021 | 1.00 55.01 |
| ATOM | 1470 | C | ASP | 190 | 17.556 | 16.115 | 58.338 | 1.00 56.16 |
| ATOM | 1471 | O | ASP | 190 | 18.083 | 16.100 | 59.463 | 1.00 58.30 |

*FIG. 5AJ*

| ATOM | 1472 | CB  | ASP | 190 | 15.195 | 16.734 | 58.955 | 1.00 | 63.89 |
|------|------|-----|-----|-----|--------|--------|--------|------|-------|
| ATOM | 1473 | CG  | ASP | 190 | 14.592 | 15.365 | 58.686 | 1.00 | 99.67 |
| ATOM | 1474 | OD1 | ASP | 190 | 14.599 | 14.466 | 59.514 | 1.00 | 100.00 |
| ATOM | 1475 | OD2 | ASP | 190 | 14.088 | 15.240 | 57.470 | 1.00 | 100.00 |
| ATOM | 1476 | N   | GLY | 191 | 17.921 | 15.312 | 57.323 | 1.00 | 47.20 |
| ATOM | 1477 | CA  | GLY | 191 | 19.015 | 14.347 | 57.419 | 1.00 | 44.96 |
| ATOM | 1478 | C   | GLY | 191 | 20.359 | 15.044 | 57.587 | 1.00 | 34.43 |
| ATOM | 1479 | O   | GLY | 191 | 20.452 | 16.266 | 57.438 | 1.00 | 29.96 |
| ATOM | 1480 | N   | PRO | 192 | 21.402 | 14.264 | 57.905 | 1.00 | 27.26 |
| ATOM | 1481 | CA  | PRO | 192 | 22.737 | 14.834 | 58.100 | 1.00 | 24.01 |
| ATOM | 1482 | C   | PRO | 192 | 23.444 | 15.274 | 56.787 | 1.00 | 20.55 |
| ATOM | 1483 | O   | PRO | 192 | 23.323 | 14.648 | 55.740 | 1.00 | 23.84 |
| ATOM | 1484 | CB  | PRO | 192 | 23.583 | 13.764 | 58.825 | 1.00 | 21.00 |
| ATOM | 1485 | CG  | PRO | 192 | 22.739 | 12.501 | 58.915 | 1.00 | 27.49 |
| ATOM | 1486 | CD  | PRO | 192 | 21.330 | 12.863 | 58.448 | 1.00 | 27.26 |
| ATOM | 1487 | N   | VAL | 193 | 24.193 | 16.363 | 56.892 | 1.00 | 17.87 |
| ATOM | 1488 | CA  | VAL | 193 | 24.964 | 16.902 | 55.792 | 1.00 | 19.51 |
| ATOM | 1489 | C   | VAL | 193 | 26.380 | 17.108 | 56.249 | 1.00 | 22.37 |
| ATOM | 1490 | O   | VAL | 193 | 26.663 | 17.189 | 57.443 | 1.00 | 23.84 |
| ATOM | 1491 | CB  | VAL | 193 | 24.449 | 18.245 | 55.256 | 1.00 | 25.24 |
| ATOM | 1492 | CG1 | VAL | 193 | 23.059 | 18.118 | 54.632 | 1.00 | 21.90 |
| ATOM | 1493 | CG2 | VAL | 193 | 24.497 | 19.322 | 56.346 | 1.00 | 24.81 |
| ATOM | 1494 | N   | LEU | 194 | 27.253 | 17.241 | 55.277 | 1.00 | 19.04 |
| ATOM | 1495 | CA  | LEU | 194 | 28.654 | 17.438 | 55.516 | 1.00 | 20.29 |
| ATOM | 1496 | C   | LEU | 194 | 29.006 | 18.930 | 55.571 | 1.00 | 18.71 |
| ATOM | 1497 | O   | LEU | 194 | 28.907 | 19.615 | 54.591 | 1.00 | 20.13 |
| ATOM | 1498 | CB  | LEU | 194 | 29.412 | 16.806 | 54.327 | 1.00 | 22.92 |
| ATOM | 1499 | CG  | LEU | 194 | 29.994 | 15.423 | 54.542 | 1.00 | 30.60 |
| ATOM | 1500 | CD1 | LEU | 194 | 29.227 | 14.642 | 55.595 | 1.00 | 35.19 |
| ATOM | 1501 | CD2 | LEU | 194 | 30.048 | 14.672 | 53.211 | 1.00 | 25.61 |
| ATOM | 1502 | N   | LEU | 195 | 29.453 | 19.430 | 56.713 | 1.00 | 17.39 |
| ATOM | 1503 | CA  | LEU | 195 | 29.881 | 20.808 | 56.785 | 1.00 | 18.83 |
| ATOM | 1504 | C   | LEU | 195 | 31.389 | 20.837 | 56.579 | 1.00 | 28.32 |
| ATOM | 1505 | O   | LEU | 195 | 32.161 | 20.152 | 57.281 | 1.00 | 21.98 |
| ATOM | 1506 | CB  | LEU | 195 | 29.489 | 21.525 | 58.072 | 1.00 | 22.20 |
| ATOM | 1507 | CG  | LEU | 195 | 28.055 | 21.349 | 58.444 | 1.00 | 26.40 |
| ATOM | 1508 | CD1 | LEU | 195 | 27.937 | 21.508 | 59.941 | 1.00 | 31.99 |
| ATOM | 1509 | CD2 | LEU | 195 | 27.225 | 22.395 | 57.726 | 1.00 | 26.90 |
| ATOM | 1510 | N   | PRO | 196 | 31.789 | 21.610 | 55.597 | 1.00 | 21.58 |
| ATOM | 1511 | CA  | PRO | 196 | 33.177 | 21.666 | 55.154 | 1.00 | 22.17 |
| ATOM | 1512 | C   | PRO | 196 | 34.080 | 22.623 | 55.892 | 1.00 | 29.56 |

*FIG. 5AK*

| | | | | | | | |
|---|---|---|---|---|---|---|---|
| ATOM | 1513 O | PRO | 196 | 33.635 | 23.588 | 56.490 | 1.00 29.04 |
| ATOM | 1514 CB | PRO | 196 | 33.054 | 22.265 | 53.752 | 1.00 22.77 |
| ATOM | 1515 CG | PRO | 196 | 31.761 | 23.104 | 53.735 | 1.00 18.99 |
| ATOM | 1516 CD | PRO | 196 | 30.910 | 22.567 | 54.861 | 1.00 16.42 |
| ATOM | 1517 N | ASP | 197 | 35.379 | 22.410 | 55.716 | 1.00 22.95 |
| ATOM | 1518 CA | ASP | 197 | 36.364 | 23.370 | 56.134 | 1.00 19.71 |
| ATOM | 1519 C | ASP | 197 | 36.556 | 24.295 | 54.931 | 1.00 24.74 |
| ATOM | 1520 O | ASP | 197 | 36.251 | 23.913 | 53.800 | 1.00 24.88 |
| ATOM | 1521 CB | ASP | 197 | 37.711 | 22.730 | 56.446 | 1.00 22.28 |
| ATOM | 1522 CG | ASP | 197 | 37.690 | 21.913 | 57.687 | 1.00 43.93 |
| ATOM | 1523 OD1 | ASP | 197 | 36.912 | 22.117 | 58.608 | 1.00 53.47 |
| ATOM | 1524 OD2 | ASP | 197 | 38.634 | 21.006 | 57.694 | 1.00 31.58 |
| ATOM | 1525 N | ASN | 198 | 37.062 | 25.501 | 55.168 | 1.00 19.74 |
| ATOM | 1526 CA | ASN | 198 | 37.254 | 26.470 | 54.118 | 1.00 15.38 |
| ATOM | 1527 C | ASN | 198 | 37.974 | 25.889 | 52.971 | 1.00 19.61 |
| ATOM | 1528 O | ASN | 198 | 38.958 | 25.236 | 53.134 | 1.00 22.69 |
| ATOM | 1529 CB | ASN | 198 | 38.013 | 27.704 | 54.614 | 1.00 24.48 |
| ATOM | 1530 CG | ASN | 198 | 37.236 | 28.504 | 55.632 | 1.00 52.21 |
| ATOM | 1531 OD1 | ASN | 198 | 36.107 | 28.174 | 55.961 | 1.00 34.54 |
| ATOM | 1532 ND2 | ASN | 198 | 37.854 | 29.556 | 56.150 | 1.00 55.11 |
| ATOM | 1533 N | HIS | 199 | 37.462 | 26.125 | 51.801 | 1.00 16.30 |
| ATOM | 1534 CA | HIS | 199 | 38.071 | 25.627 | 50.616 | 1.00 15.80 |
| ATOM | 1535 C | HIS | 199 | 37.496 | 26.357 | 49.450 | 1.00 14.85 |
| ATOM | 1536 O | HIS | 199 | 36.757 | 27.295 | 49.643 | 1.00 16.45 |
| ATOM | 1537 CB | HIS | 199 | 37.988 | 24.103 | 50.471 | 1.00 16.53 |
| ATOM | 1538 CG | HIS | 199 | 36.597 | 23.628 | 50.218 | 1.00 16.65 |
| ATOM | 1539 ND1 | HIS | 199 | 35.695 | 23.491 | 51.244 | 1.00 17.85 |
| ATOM | 1540 CD2 | HIS | 199 | 35.987 | 23.282 | 49.048 | 1.00 18.67 |
| ATOM | 1541 CE1 | HIS | 199 | 34.561 | 23.052 | 50.688 | 1.00 19.45 |
| ATOM | 1542 NE2 | HIS | 199 | 34.716 | 22.905 | 49.364 | 1.00 18.74 |
| ATOM | 1543 N | TYR | 200 | 37.879 | 25.998 | 48.247 | 1.00 12.56 |
| ATOM | 1544 CA | TYR | 200 | 37.334 | 26.689 | 47.100 | 1.00 14.01 |
| ATOM | 1545 C | TYR | 200 | 37.207 | 25.824 | 45.870 | 1.00 15.57 |
| ATOM | 1546 O | TYR | 200 | 37.793 | 24.751 | 45.768 | 1.00 20.20 |
| ATOM | 1547 CB | TYR | 200 | 38.030 | 28.011 | 46.779 | 1.00 19.79 |
| ATOM | 1548 CG | TYR | 200 | 39.382 | 27.745 | 46.202 | 1.00 22.25 |
| ATOM | 1549 CD1 | TYR | 200 | 39.543 | 27.526 | 44.835 | 1.00 22.53 |
| ATOM | 1550 CD2 | TYR | 200 | 40.473 | 27.605 | 47.057 | 1.00 25.73 |
| ATOM | 1551 CE1 | TYR | 200 | 40.800 | 27.222 | 44.317 | 1.00 35.51 |
| ATOM | 1552 CE2 | TYR | 200 | 41.739 | 27.314 | 46.559 | 1.00 29.34 |
| ATOM | 1553 CZ | TYR | 200 | 41.896 | 27.132 | 45.186 | 1.00 54.14 |

*FIG. 5AL*

| | | | | | | | |
|---|---|---|---|---|---|---|---|
| ATOM | 1554 OH | TYR | 200 | 43.153 | 26.820 | 44.703 | 1.00 62.66 |
| ATOM | 1555 N | LEU | 201 | 36.393 | 26.309 | 44.946 | 1.00 15.07 |
| ATOM | 1556 CA | LEU | 201 | 36.147 | 25.680 | 43.678 | 1.00 11.01 |
| ATOM | 1557 C | LEU | 201 | 36.753 | 26.532 | 42.593 | 1.00 17.30 |
| ATOM | 1558 O | LEU | 201 | 36.619 | 27.753 | 42.610 | 1.00 20.19 |
| ATOM | 1559 CB | LEU | 201 | 34.628 | 25.518 | 43.354 | 1.00 10.09 |
| ATOM | 1560 CG | LEU | 201 | 33.749 | 25.027 | 44.480 | 1.00 13.41 |
| ATOM | 1561 CD1 | LEU | 201 | 32.293 | 24.938 | 43.954 | 1.00 17.11 |
| ATOM | 1562 CD2 | LEU | 201 | 34.196 | 23.635 | 44.927 | 1.00 23.03 |
| ATOM | 1563 N | SER | 202 | 37.407 | 25.868 | 41.651 | 1.00 10.75 |
| ATOM | 1564 CA | SER | 202 | 38.047 | 26.490 | 40.528 | 1.00 8.51 |
| ATOM | 1565 C | SER | 202 | 37.222 | 26.189 | 39.294 | 1.00 11.56 |
| ATOM | 1566 O | SER | 202 | 36.919 | 25.038 | 38.996 | 1.00 14.58 |
| ATOM | 1567 CB | SER | 202 | 39.485 | 25.987 | 40.442 | 1.00 15.68 |
| ATOM | 1568 OG | SER | 202 | 40.067 | 26.353 | 39.228 | 1.00 36.44 |
| ATOM | 1569 N | THR | 203 | 36.798 | 27.241 | 38.601 | 1.00 12.36 |
| ATOM | 1570 CA | THR | 203 | 35.879 | 27.067 | 37.499 | 1.00 15.60 |
| ATOM | 1571 C | THR | 203 | 36.417 | 27.521 | 36.195 | 1.00 20.19 |
| ATOM | 1572 O | THR | 203 | 37.192 | 28.472 | 36.114 | 1.00 18.29 |
| ATOM | 1573 CB | THR | 203 | 34.565 | 27.892 | 37.757 | 1.00 20.51 |
| ATOM | 1574 OG1 | THR | 203 | 34.911 | 29.260 | 37.780 | 1.00 20.39 |
| ATOM | 1575 CG2 | THR | 203 | 33.935 | 27.557 | 39.093 | 1.00 6.80 |
| ATOM | 1576 N | GLN | 204 | 35.913 | 26.883 | 35.164 | 1.00 10.30 |
| ATOM | 1577 CA | GLN | 204 | 36.173 | 27.271 | 33.807 | 1.00 14.85 |
| ATOM | 1578 C | GLN | 204 | 34.956 | 26.980 | 32.921 | 1.00 23.14 |
| ATOM | 1579 O | GLN | 204 | 34.334 | 25.932 | 33.056 | 1.00 21.66 |
| ATOM | 1580 CB | GLN | 204 | 37.475 | 26.696 | 33.237 | 1.00 20.33 |
| ATOM | 1581 CG | GLN | 204 | 37.271 | 25.371 | 32.518 | 1.00 40.16 |
| ATOM | 1582 CD | GLN | 204 | 38.588 | 24.722 | 32.193 | 1.00 59.76 |
| ATOM | 1583 OE1 | GLN | 204 | 39.011 | 24.716 | 31.035 | 1.00 41.80 |
| ATOM | 1584 NE2 | GLN | 204 | 39.276 | 24.241 | 33.235 | 1.00 34.80 |
| ATOM | 1585 N | SER | 205 | 34.619 | 27.913 | 32.021 | 1.00 15.83 |
| ATOM | 1586 CA | SER | 205 | 33.447 | 27.762 | 31.172 | 1.00 14.60 |
| ATOM | 1587 C | SER | 205 | 33.654 | 28.307 | 29.783 | 1.00 20.21 |
| ATOM | 1588 O | SER | 205 | 34.282 | 29.337 | 29.581 | 1.00 17.82 |
| ATOM | 1589 CB | SER | 205 | 32.197 | 28.445 | 31.758 | 1.00 11.88 |
| ATOM | 1590 OG | SER | 205 | 32.121 | 28.406 | 33.177 | 1.00 15.45 |
| ATOM | 1591 N | ALA | 206 | 33.065 | 27.630 | 28.827 | 1.00 13.00 |
| ATOM | 1592 CA | ALA | 206 | 33.079 | 28.029 | 27.426 | 1.00 9.99 |
| ATOM | 1593 C | ALA | 206 | 31.623 | 28.192 | 26.924 | 1.00 21.23 |
| ATOM | 1594 O | ALA | 206 | 30.809 | 27.306 | 27.139 | 1.00 14.10 |

*FIG. 5AM*

| | | | | | | | |
|---|---|---|---|---|---|---|---|
| ATOM | 1595 CB | ALA | 206 | 33.751 | 26.936 | 26.596 | 1.00 13.45 |
| ATOM | 1596 N | LEU | 207 | 31.335 | 29.320 | 26.263 | 1.00 16.09 |
| ATOM | 1597 CA | LEU | 207 | 30.036 | 29.167 | 25.706 | 1.00 12.07 |
| ATOM | 1598 C | LEU | 207 | 30.070 | 29.445 | 24.235 | 1.00 19.76 |
| ATOM | 1599 O | LEU | 207 | 31.014 | 29.840 | 23.576 | 1.00 20.82 |
| ATOM | 1600 CB | LEU | 207 | 29.580 | 31.057 | 26.004 | 1.00  8.24 |
| ATOM | 1601 CG | LEU | 207 | 29.744 | 31.493 | 27.457 | 1.00 16.35 |
| ATOM | 1602 CD1 | LEU | 207 | 28.955 | 32.790 | 27.707 | 1.00 13.78 |
| ATOM | 1603 CD2 | LEU | 207 | 29.268 | 30.406 | 28.400 | 1.00 18.79 |
| ATOM | 1604 N | SER | 208 | 29.011 | 28.863 | 23.698 | 1.00 15.35 |
| ATOM | 1605 CA | SER | 208 | 28.914 | 28.692 | 22.270 | 1.00 13.74 |
| ATOM | 1606 C | SER | 208 | 27.449 | 28.852 | 21.794 | 1.00 20.16 |
| ATOM | 1607 O | SER | 208 | 26.548 | 29.085 | 22.594 | 1.00 15.81 |
| ATOM | 1608 CB | SER | 208 | 29.495 | 27.367 | 21.822 | 1.00 17.82 |
| ATOM | 1609 OG | SER | 208 | 28.769 | 26.311 | 22.431 | 1.00 31.45 |
| ATOM | 1610 N | LYS | 209 | 27.242 | 28.738 | 20.485 | 1.00 16.50 |
| ATOM | 1611 CA | LYS | 209 | 25.907 | 28.828 | 19.906 | 1.00 18.02 |
| ATOM | 1612 C | LYS | 209 | 25.637 | 27.610 | 19.031 | 1.00 29.99 |
| ATOM | 1613 O | LYS | 209 | 26.578 | 27.004 | 18.502 | 1.00 32.55 |
| ATOM | 1614 CB | LYS | 209 | 25.783 | 30.100 | 19.082 | 1.00 20.96 |
| ATOM | 1615 CG | LYS | 209 | 24.746 | 31.055 | 19.606 | 1.00 34.50 |
| ATOM | 1616 CD | LYS | 209 | 25.262 | 31.964 | 20.666 | 1.00 22.72 |
| ATOM | 1617 CE | LYS | 209 | 24.370 | 33.159 | 290.896 | 1.00 18.96 |
| ATOM | 1618 NZ | LYS | 209 | 23.565 | 33.067 | 22.116 | 1.00 27.39 |
| ATOM | 1619 N | ASP | 210 | 24.347 | 27.241 | 18.912 | 1.00 27.01 |
| ATOM | 1620 CA | ASP | 210 | 23.890 | 26.159 | 18.038 | 1.00 24.62 |
| ATOM | 1621 C | ASP | 210 | 23.465 | 26.793 | 16.705 | 1.00 26.77 |
| ATOM | 1622 O | ASP | 210 | 22.468 | 27.514 | 16.605 | 1.00 23.00 |
| ATOM | 1623 CB | ASP | 210 | 22.744 | 25.361 | 18.691 | 1.00 24.43 |
| ATOM | 1624 CG | ASP | 210 | 22.197 | 24.249 | 17.839 | 1.00 35.55 |
| ATOM | 1625 OD1 | ASP | 210 | 22.333 | 24.185 | 16.631 | 1.00 36.53 |
| ATOM | 1626 OD2 | ASP | 210 | 21.499 | 23.400 | 18.535 | 1.00 45.51 |
| ATOM | 1627 N | PRO | 211 | 24.306 | 26.618 | 15.708 | 1.00 30.25 |
| ATOM | 1628 CA | PRO | 211 | 24.120 | 27.224 | 14.397 | 1.00 30.30 |
| ATOM | 1629 C | PRO | 211 | 22.733 | 26.982 | 13.770 | 1.00 39.72 |
| ATOM | 1630 O | PRO | 211 | 22.253 | 27.782 | 12.959 | 1.00 37.65 |
| ATOM | 1631 CB | PRO | 211 | 25.197 | 26.620 | 13.500 | 1.00 29.99 |
| ATOM | 1632 CG | PRO | 211 | 25.782 | 25.418 | 14.255 | 1.00 38.59 |
| ATOM | 1633 CD | PRO | 211 | 25.158 | 25.405 | 15.647 | 1.00 35.05 |
| ATOM | 1634 N | ASN | 212 | 22.102 | 25.868 | 14.140 | 1.00 39.64 |
| ATOM | 1635 CA | ASN | 212 | 20.808 | 25.515 | 13.592 | 1.00 39.60 |

*FIG. 5AN*

| | | | | | | | |
|---|---|---|---|---|---|---|---|
| ATOM | 1636 | C | ASN | 212 | 19.642 | 25.894 | 14.497 | 1.00 41.92 |
| ATOM | 1637 | O | ASN | 212 | 18.485 | 25.518 | 14.263 | 1.00 42.30 |
| ATOM | 1638 | CB | ASN | 212 | 20.788 | 24.028 | 13.236 | 1.00 48.64 |
| ATOM | 1639 | CG | ASN | 212 | 21.883 | 23.678 | 12.230 | 1.00 53.61 |
| ATOM | 1640 | N | GLU | 213 | 19.947 | 26.675 | 15.520 | 1.00 27.84 |
| ATOM | 1641 | CA | GLU | 213 | 18.953 | 27.080 | 16.478 | 1.00 20.43 |
| ATOM | 1642 | C | GLU | 213 | 18.485 | 28.527 | 16.241 | 1.00 29.95 |
| ATOM | 1643 | O | GLU | 213 | 19.247 | 29.475 | 16.324 | 1.00 32.77 |
| ATOM | 1644 | CB | GLU | 213 | 19.535 | 26.878 | 17.894 | 1.00 16.45 |
| ATOM | 1645 | CG | GLU | 213 | 18.594 | 27.326 | 18.995 | 1.00 18.29 |
| ATOM | 1646 | CD | GLU | 213 | 17.229 | 26.703 | 18.853 | 1.00 38.01 |
| ATOM | 1647 | OE1 | GLU | 213 | 16.238 | 27.334 | 18.508 | 1.00 25.07 |
| ATOM | 1648 | OE2 | GLU | 213 | 17.223 | 25.423 | 19.122 | 1.00 19.17 |
| ATOM | 1649 | N | LYS | 214 | 17.223 | 28.713 | 15.963 | 1.00 22.99 |
| ATOM | 1650 | CA | LYS | 214 | 16.721 | 30.081 | 15.726 | 1.00 22.84 |
| ATOM | 1651 | C | LYS | 214 | 16.252 | 30.778 | 16.982 | 1.00 21.50 |
| ATOM | 1652 | O | LYS | 214 | 16.130 | 32.016 | 17.032 | 1.00 28.15 |
| ATOM | 1653 | CB | LYS | 214 | 15.653 | 30.197 | 14.606 | 1.00 27.58 |
| ATOM | 1654 | CG | LYS | 214 | 16.153 | 29.816 | 13.209 | 1.00 32.71 |
| ATOM | 1655 | CD | LYS | 214 | 16.752 | 30.979 | 12.431 | 1.00 55.31 |
| ATOM | 1656 | N | ARG | 215 | 15.947 | 30.028 | 18.014 | 1.00 14.52 |
| ATOM | 1657 | CA | ARG | 215 | 15.518 | 30.726 | 19.209 | 1.00 15.58 |
| ATOM | 1658 | C | ARG | 215 | 16.719 | 31.382 | 19.892 | 1.00 21.87 |
| ATOM | 1659 | O | ARG | 215 | 17.848 | 31.075 | 19.572 | 1.00 26.69 |
| ATOM | 1660 | CB | ARG | 215 | 14.808 | 29.804 | 20.159 | 1.00 18.82 |
| ATOM | 1661 | CG | ARG | 215 | 13.660 | 29.067 | 19.475 | 1.00 23.30 |
| ATOM | 1662 | CD | ARG | 215 | 13.220 | 27.806 | 20.205 | 1.00 15.45 |
| ATOM | 1663 | NE | ARG | 215 | 14.107 | 26.668 | 19.929 | 1.00 28.08 |
| ATOM | 1664 | CZ | ARG | 215 | 14.022 | 25.473 | 20.543 | 1.00 21.38 |
| ATOM | 1665 | NH1 | ARG | 215 | 13.074 | 25.215 | 21.455 | 1.00 23.92 |
| ATOM | 1666 | NH2 | ARG | 215 | 14.893 | 24.514 | 20.225 | 1.00 20.46 |
| ATOM | 1667 | N | ASP | 216 | 16.466 | 32.275 | 20.830 | 1.00 16.72 |
| ATOM | 1668 | CA | ASP | 216 | 17.556 | 32.895 | 21.617 | 1.00 19.06 |
| ATOM | 1669 | C | ASP | 216 | 18.047 | 31.817 | 22.607 | 1.00 20.02 |
| ATOM | 1670 | O | ASP | 216 | 17.261 | 31.214 | 23.350 | 1.00 18.45 |
| ATOM | 1671 | CB | ASP | 216 | 17.066 | 34.169 | 22.383 | 1.00 21.33 |
| ATOM | 1672 | CG | ASP | 216 | 18.138 | 35.140 | 22.893 | 1.00 20.97 |
| ATOM | 1673 | OD1 | ASP | 216 | 17.869 | 36.079 | 23.620 | 1.00 28.46 |
| ATOM | 1674 | OD2 | ASP | 216 | 19.342 | 34.900 | 22.441 | 1.00 20.37 |
| ATOM | 1675 | N | HIS | 217 | 19.332 | 31.537 | 22.589 | 1.00 13.18 |
| ATOM | 1676 | CA | HIS | 217 | 19.813 | 30.482 | 23.433 | 1.00 11.21 |

FIG. 5AO

| | | | | | | | |
|---|---|---|---|---|---|---|---|
| ATOM | 1677 | C | HIS | 217 | 21.313 | 30.614 | 23.723 | 1.00 21.35 |
| ATOM | 1678 | O | HIS | 217 | 22.014 | 31.471 | 23.163 | 1.00 15.03 |
| ATOM | 1679 | CB | HIS | 217 | 19.587 | 29.168 | 22.690 | 1.00 13.03 |
| ATOM | 1680 | CG | HIS | 217 | 20.525 | 29.025 | 21.542 | 1.00 15.49 |
| ATOM | 1681 | ND1 | HIS | 217 | 20.463 | 29.871 | 20.449 | 1.00 17.88 |
| ATOM | 1682 | CD2 | HIS | 217 | 21.589 | 28.172 | 21.361 | 1.00 17.51 |
| ATOM | 1683 | CE1 | HIS | 217 | 21.457 | 29.524 | 19.635 | 1.00 17.94 |
| ATOM | 1684 | NE2 | HIS | 217 | 22.152 | 28.501 | 20.151 | 1.00 17.59 |
| ATOM | 1685 | N | MSE | 218 | 21.794 | 29.725 | 24.576 | 1.00 11.26 |
| ATOM | 1686 | CA | MSE | 218 | 23.186 | 29.642 | 24.887 | 1.00 11.49 |
| ATOM | 1687 | C | MSE | 218 | 23.560 | 28.198 | 25.094 | 1.00 24.15 |
| ATOM | 1688 | O | MSE | 218 | 22.822 | 27.446 | 25.751 | 1.00 20.70 |
| ATOM | 1689 | CB | MSE | 218 | 23.539 | 30.421 | 26.172 | 1.00 12.84 |
| ATOM | 1690 | CG | MSE | 218 | 24.809 | 30.004 | 26.907 | 1.00 12.59 |
| ATOM | 1691 | SE | MSE | 218 | 25.267 | 31.128 | 28.434 | 1.00 29.94 |
| ATOM | 1692 | CE | MSE | 218 | 24.039 | 30.502 | 29.781 | 1.00 13.54 |
| ATOM | 1693 | N | VAL | 219 | 24.727 | 27.824 | 24.558 | 1.00 15.62 |
| ATOM | 1694 | CA | VAL | 219 | 25.309 | 26.518 | 24.782 | 1.00 10.58 |
| ATOM | 1695 | C | VAL | 219 | 26.473 | 26.689 | 25.753 | 1.00 16.54 |
| ATOM | 1696 | O | VAL | 219 | 27.280 | 27.604 | 25.585 | 1.00 15.54 |
| ATOM | 1697 | CB | VAL | 219 | 25.774 | 25.883 | 23.498 | 1.00 15.08 |
| ATOM | 1698 | CG1 | VAL | 219 | 26.330 | 24.495 | 23.824 | 1.00 14.34 |
| ATOM | 1699 | CG2 | VAL | 219 | 24.599 | 25.766 | 22.512 | 1.00 15.78 |
| ATOM | 1700 | N | LEU | 220 | 26.523 | 25.836 | 26.783 | 1.00 10.95 |
| ATOM | 1701 | CA | LEU | 220 | 27.490 | 25.939 | 27.850 | 1.00 11.01 |
| ATOM | 1702 | C | LEU | 220 | 28.206 | 24.643 | 28.184 | 1.00 21.26 |
| ATOM | 1703 | O | LEU | 220 | 27.592 | 23.577 | 28.324 | 1.00 15.94 |
| ATOM | 1704 | CB | LEU | 220 | 26.807 | 26.545 | 29.100 | 1.00 13.75 |
| ATOM | 1705 | CG | LEU | 220 | 27.624 | 26.578 | 30.402 | 1.00 21.10 |
| ATOM | 1706 | CD1 | LEU | 220 | 28.433 | 27.875 | 30.483 | 1.00 23.53 |
| ATOM | 1707 | CD2 | LEU | 220 | 26.663 | 26.556 | 31.586 | 1.00 22.04 |
| ATOM | 1708 | N | LEU | 221 | 29.570 | 24.758 | 28.273 | 1.00 19.04 |
| ATOM | 1709 | CA | LEU | 221 | 30.498 | 23.666 | 28.697 | 1.00 13.22 |
| ATOM | 1710 | C | LEU | 221 | 31.309 | 24.178 | 29.887 | 1.00 10.73 |
| ATOM | 1711 | O | LEU | 221 | 31.846 | 25.267 | 29.857 | 1.00 12.98 |
| ATOM | 1712 | CB | LEU | 221 | 31.382 | 23.102 | 27.549 | 1.00 13.74 |
| ATOM | 1713 | CG | LEU | 221 | 32.580 | 22.257 | 28.045 | 1.00 18.64 |
| ATOM | 1714 | CD1 | LEU | 221 | 32.149 | 20.868 | 28.496 | 1.00 17.38 |
| ATOM | 1715 | CD2 | LEU | 221 | 33.571 | 22.109 | 26.911 | 1.00 26.97 |
| ATOM | 1716 | N | GLU | 222 | 31.316 | 23.446 | 30.963 | 1.00 9.31 |
| ATOM | 1717 | CA | GLU | 222 | 31.936 | 23.929 | 32.144 | 1.00 9.97 |

*FIG. 5AP*

| | | | | | | | |
|---|---|---|---|---|---|---|---|
| ATOM | 1718 | C | GLU | 222 | 32.548 | 22.803 | 32.951 | 1.00 12.94 |
| ATOM | 1719 | O | GLU | 222 | 32.072 | 21.662 | 32.966 | 1.00 13.38 |
| ATOM | 1720 | CB | GLU | 222 | 30.836 | 24.762 | 32.896 | 1.00 12.14 |
| ATOM | 1721 | CG | GLU | 222 | 31.092 | 25.119 | 34.364 | 1.00 13.88 |
| ATOM | 1722 | CD | GLU | 222 | 29.895 | 25.891 | 34.934 | 1.00 13.57 |
| ATOM | 1723 | OE1 | GLU | 222 | 29.128 | 26.477 | 34.240 | 1.00 19.47 |
| ATOM | 1724 | OE2 | GLU | 222 | 29.752 | 25.789 | 36.207 | 1.00 18.51 |
| ATOM | 1725 | N | PHE | 223 | 33.687 | 23.123 | 33.542 | 1.00 15.86 |
| ATOM | 1726 | CA | PHE | 223 | 34.476 | 22.227 | 34.373 | 1.00 9.34 |
| ATOM | 1727 | C | PHE | 223 | 34.711 | 22.864 | 35.722 | 1.00 11.08 |
| ATOM | 1728 | O | PHE | 223 | 35.028 | 24.055 | 35.828 | 1.00 19.86 |
| ATOM | 1729 | CB | PHE | 223 | 35.847 | 21.919 | 33.684 | 1.00 8.30 |
| ATOM | 1730 | CG | PHE | 223 | 35.703 | 21.134 | 32.431 | 1.00 10.50 |
| ATOM | 1731 | CD1 | PHE | 223 | 35.570 | 19.747 | 32.469 | 1.00 13.56 |
| ATOM | 1732 | CD2 | PHE | 223 | 35.750 | 21.750 | 31.184 | 1.00 11.32 |
| ATOM | 1733 | CE1 | PHE | 223 | 35.481 | 19.010 | 31.287 | 1.00 12.58 |
| ATOM | 1734 | CE2 | PHE | 223 | 35.667 | 21.032 | 29.995 | 1.00 12.17 |
| ATOM | 1735 | CZ | PHE | 223 | 35.521 | 19.648 | 30.050 | 1.00 10.87 |
| ATOM | 1736 | N | VAL | 224 | 34.542 | 22.081 | 36.765 | 1.00 9.28 |
| ATOM | 1737 | CA | VAL | 224 | 34.708 | 22.587 | 38.080 | 1.00 11.18 |
| ATOM | 1738 | C | VAL | 224 | 35.324 | 21.553 | 39.010 | 1.00 17.52 |
| ATOM | 1739 | O | VAL | 224 | 34.848 | 20.418 | 39.137 | 1.00 13.17 |
| ATOM | 1740 | CB | VAL | 224 | 33.370 | 23.078 | 38.662 | 1.00 16.61 |
| ATOM | 1741 | CG1 | VAL | 224 | 33.622 | 23.736 | 40.022 | 1.00 13.90 |
| ATOM | 1742 | CG2 | VAL | 224 | 32.674 | 24.048 | 37.697 | 1.00 13.85 |
| ATOM | 1743 | N | THR | 225 | 36.380 | 21.965 | 39.676 | 1.00 11.71 |
| ATOM | 1744 | CA | THR | 225 | 37.026 | 21.099 | 40.617 | 1.00 11.61 |
| ATOM | 1745 | C | THR | 225 | 37.366 | 21.798 | 41.927 | 1.00 14.76 |
| ATOM | 1746 | O | THR | 225 | 37.702 | 23.002 | 41.962 | 1.00 16.64 |
| ATOM | 1747 | CB | THR | 225 | 38.162 | 20.279 | 40.014 | 1.00 20.38 |
| ATOM | 1748 | OG1 | THR | 225 | 39.288 | 20.337 | 40.822 | 1.00 30.44 |
| ATOM | 1749 | CG2 | THR | 225 | 38.468 | 20.722 | 38.631 | 1.00 10.89 |
| ATOM | 1750 | N | ALA | 226 | 37.222 | 21.065 | 43.011 | 1.00 7.89 |
| ATOM | 1751 | CA | ALA | 226 | 37.478 | 21.595 | 44.352 | 1.00 11.63 |
| ATOM | 1752 | C | ALA | 226 | 38.969 | 21.558 | 44.677 | 1.00 16.61 |
| ATOM | 1753 | O | ALA | 226 | 39.687 | 20.699 | 44.199 | 1.00 15.60 |
| ATOM | 1754 | CB | ALA | 226 | 36.695 | 20.847 | 45.444 | 1.00 12.17 |
| ATOM | 1755 | N | ALA | 227 | 39.395 | 22.490 | 45.479 | 1.00 13.95 |
| ATOM | 1756 | CA | ALA | 227 | 40.789 | 22.550 | 45.871 | 1.00 19.64 |
| ATOM | 1757 | C | ALA | 227 | 40.987 | 23.299 | 47.170 | 1.00 26.33 |
| ATOM | 1758 | O | ALA | 227 | 40.042 | 23.715 | 47.840 | 1.00 25.39 |

*FIG. 5AQ*

| ATOM | 1759 | CB  | ALA | 227 | 41.557 | 23.246 | 44.760 | 1.00 | 18.42 |
| ---- | ---- | --- | --- | --- | ------ | ------ | ------ | ---- | ----- |
| ATOM | 1760 | N   | GLY | 228 | 42.245 | 23.476 | 47.523 | 1.00 | 23.28 |
| ATOM | 1761 | CA  | GLY | 228 | 42.616 | 24.292 | 48.658 | 1.00 | 21.61 |
| ATOM | 1762 | C   | GLY | 228 | 42.805 | 23.562 | 49.939 | 1.00 | 32.93 |
| ATOM | 1763 | O   | GLY | 228 | 42.948 | 24.201 | 51.009 | 1.00 | 32.53 |
| ATOM | 1764 | N   | ILE | 229 | 42.803 | 22.231 | 49.842 | 1.00 | 33.59 |
| ATOM | 1765 | CA  | ILE | 229 | 43.006 | 21.375 | 50.998 | 1.00 | 31.81 |
| ATOM | 1766 | C   | ILE | 229 | 44.016 | 20.291 | 50.633 | 1.00 | 28.78 |
| ATOM | 1767 | O   | ILE | 229 | 45.090 | 20.176 | 51.246 | 1.00 | 96.02 |
| ATOM | 1768 | CB  | ILE | 229 | 41.691 | 20.772 | 51.519 | 1.00 | 35.70 |
| ATOM | 1769 | CG1 | ILE | 229 | 40.890 | 21.807 | 52.325 | 1.00 | 30.66 |
| ATOM | 1770 | CG2 | ILE | 229 | 41.990 | 19.549 | 52.392 | 1.00 | 33.37 |
| ATOM | 1771 | CD1 | ILE | 229 | 39.386 | 21.715 | 52.092 | 1.00 | 38.74 |
| ATOM | 1772 | O   | HOH | 301 | 27.530 | 12.735 | 38.010 | 1.00 | 15.09 |
| ATOM | 1773 | O   | HOH | 302 | 23.919 | 34.589 | 37.331 | 1.00 | 10.29 |
| ATOM | 1774 | O   | HOH | 303 | 27.229 | 34.816 | 35.487 | 1.00 | 11.12 |
| ATOM | 1775 | O   | HOH | 304 | 29.914 | 18.943 | 44.692 | 1.00 | 16.10 |
| ATOM | 1776 | O   | HOH | 305 | 30.956 | 21.886 | 49.900 | 1.00 | 21.47 |
| ATOM | 1777 | O   | HOH | 306 | 20.072 | 31.196 | 43.592 | 1.00 | 16.85 |
| ATOM | 1778 | O   | HOH | 307 | 26.660 | 48.630 | 33.797 | 1.00 | 24.67 |
| ATOM | 1779 | O   | HOH | 308 | 22.329 | 33.239 | 41.399 | 1.00 | 14.11 |
| ATOM | 1780 | O   | HOH | 309 | 22.465 | 48.025 | 32.810 | 1.00 | 18.51 |
| ATOM | 1781 | O   | HOH | 310 | 31.012 | 39.126 | 29.118 | 1.00 | 16.01 |
| ATOM | 1782 | O   | HOH | 311 | 33.067 | 35.809 | 33.010 | 1.00 | 19.92 |
| ATOM | 1783 | O   | HOH | 312 | 31.130 | 37.076 | 30.841 | 1.00 | 12.68 |
| ATOM | 1784 | O   | HOH | 313 | 40.304 | 30.058 | 38.616 | 1.00 | 56.07 |
| ATOM | 1785 | O   | HOH | 314 | 34.166 | 26.379 | 57.222 | 1.00 | 22.58 |
| ATOM | 1786 | O   | HOH | 315 | 36.215 | 35.320 | 43.598 | 1.00 | 22.30 |
| ATOM | 1787 | O   | HOH | 316 | 33.866 | 29.786 | 34.671 | 1.00 | 12.21 |
| ATOM | 1865 | O   | HOH | 317 | 42.341 | 20.166 | 43.534 | 1.00 | 26.67 |
| ATOM | 1788 | O   | HOH | 318 | 10.270 | 28.684 | 30.403 | 1.00 | 43.66 |
| ATOM | 1789 | O   | HOH | 319 | 28.448 | 16.822 | 30.655 | 1.00 | 25.44 |
| ATOM | 1790 | O   | HOH | 320 | 30.612 | 20.922 | 37.231 | 1.00 | 21.57 |
| ATOM | 1791 | O   | HOH | 321 | 11.639 | 37.421 | 26.801 | 1.00 | 34.12 |
| ATOM | 1792 | O   | HOH | 322 | 27.030 | 37.308 | 36.869 | 1.00 | 13.10 |
| ATOM | 1793 | O   | HOH | 323 | 33.119 | 14.524 | 43.070 | 1.00 | 30.93 |
| ATOM | 1794 | O   | HOH | 324 | 37.973 | 14.036 | 53.352 | 1.00 | 35.39 |
| ATOM | 1795 | O   | HOH | 235 | 32.015 | 49.100 | 37.028 | 1.00 | 59.37 |
| ATOM | 1796 | O   | HOH | 326 | 11.959 | 12.020 | 43.429 | 1.00 | 29.06 |
| ATOM | 1797 | O   | HOH | 327 | 36.760 | 29.941 | 31.666 | 1.00 | 22.03 |
| ATOM | 1864 | O   | HOH | 328 | 15.305 | 26.513 | 15.694 | 1.00 | 39.62 |

*FIG. 5AR*

| | | | | | | | |
|---|---|---|---|---|---|---|---|
| ATOM | 1798 O | HOH | 329 | 33.005 | 46.924 | 36.994 | 1.00 22.07 |
| ATOM | 1863 O | HOH | 330 | 23.801 | 36.134 | 22.715 | 1.00 45.30 |
| ATOM | 1799 O | HOH | 331 | 33.609 | 31.296 | 26.261 | 1.00 23.65 |
| ATOM | 1862 O | HOH | 332 | 34.942 | 24.780 | 29.532 | 1.00 38.93 |
| ATOM | 1800 O | HOH | 333 | 25.235 | 12.919 | 54.611 | 1.00 36.20 |
| ATOM | 1861 O | HOH | 334 | 38.048 | 23.467 | 36.645 | 1.00 37.73 |
| ATOM | 1801 O | HOH | 335 | 12.284 | 43.511 | 38.338 | 1.00 33.79 |
| ATOM | 1802 O | HOH | 336 | 9.826 | 47.020 | 32.568 | 1.00 46.67 |
| ATOM | 1803 O | HOH | 337 | 7.671 | 41.532 | 29.806 | 1.00 40.88 |
| ATOM | 1804 O | HOH | 338 | 15.430 | 23.713 | 26.808 | 1.00 34.73 |
| ATOM | 1805 O | HOH | 339 | 24.344 | 20.385 | 25.121 | 1.00 53.42 |
| ATOM | 1806 O | HOH | 340 | 31.550 | 10.656 | 40.819 | 1.00 47.85 |
| ATOM | 1807 O | HOH | 341 | 17.569 | 23.030 | 25.796 | 1.00 28.17 |
| ATOM | 1808 O | HOH | 342 | 19.174 | 38.552 | 23.965 | 1.00 45.54 |
| ATOM | 1809 O | HOH | 343 | 24.268 | 37.527 | 25.415 | 1.00 30.97 |
| ATOM | 1810 O | HOH | 344 | 21.266 | 29.482 | 41.551 | 1.00 19.69 |
| ATOM | 1811 O | HOH | 345 | 20.668 | 26.999 | 41.933 | 1.00 11.81 |
| ATOM | 1812 O | HOH | 346 | 24.780 | 24.795 | 43.460 | 1.00 20.95 |
| ATOM | 1813 O | HOH | 347 | 42.962 | 13.170 | 46.312 | 1.00 31.00 |
| ATOM | 1814 O | HOH | 348 | 32.322 | 14.088 | 47.013 | 1.00 28.20 |
| ATOM | 1815 O | HOH | 349 | 31.708 | 13.186 | 49.679 | 1.00 35.57 |
| ATOM | 1816 O | HOH | 350 | 22.408 | 35.801 | 50.514 | 1.00 40.71 |
| ATOM | 1817 O | HOH | 351 | 25.366 | 47.090 | 42.583 | 1.00 38.15 |
| ATOM | 1818 O | HOH | 352 | 27.243 | 47.647 | 43.977 | 1.00 41.55 |
| ATOM | 1819 O | HOH | 353 | 29.868 | 45.076 | 42.906 | 1.00 29.32 |
| ATOM | 1820 O | HOH | 354 | 14.175 | 22.269 | 42.680 | 1.00 74.11 |
| ATOM | 1821 O | HOH | 355 | 13.414 | 10.739 | 35.791 | 1.00 29.92 |
| ATOM | 1822 O | HOH | 356 | 20.338 | 9.974 | 37.765 | 1.00 30.46 |
| ATOM | 1823 O | HOH | 357 | 23.520 | 40.420 | 24.953 | 1.00 29.75 |
| ATOM | 1824 O | HOH | 358 | 25.718 | 41.692 | 26.023 | 1.00 30.43 |
| ATOM | 1825 O | HOH | 359 | 26.826 | 38.466 | 25.345 | 1.00 31.72 |
| ATOM | 1826 O | HOH | 360 | 37.768 | 42.373 | 25.123 | 1.00 41.53 |
| ATOM | 1827 O | HOH | 361 | 40.078 | 42.268 | 25.852 | 1.00 37.12 |
| ATOM | 1828 O | HOH | 362 | 31.483 | 38.677 | 22.083 | 1.00 54.21 |
| ATOM | 1829 O | HOH | 363 | 33.891 | 37.723 | 30.126 | 1.00 23.35 |
| ATOM | 1860 O | HOH | 364 | 39.936 | 26.543 | 36.329 | 1.00 47.93 |
| ATOM | 1830 O | HOH | 365 | 36.631 | 34.210 | 41.636 | 1.00 62.74 |
| ATOM | 1831 O | HOH | 366 | 37.038 | 29.783 | 52.197 | 1.00 40.07 |
| ATOM | 1832 O | HOH | 367 | 37.289 | 37.407 | 40.231 | 1.00 37.59 |
| ATOM | 1833 O | HOH | 368 | 18.930 | 17.517 | 52.472 | 1.00 35.80 |
| ATOM | 1834 O | HOH | 369 | 19.506 | 18.914 | 57.913 | 1.00 45.72 |

*FIG. 5AS*

| ATOM | 1835 | O | HOH | 370 | 30.903 | 26.708 | 41.139 | 1.00 | 21.54 |
|---|---|---|---|---|---|---|---|---|---|
| ATOM | 1836 | O | HOH | 371 | 30.369 | 25.678 | 24.583 | 1.00 | 22.46 |
| ATOM | 1837 | O | HOH | 372 | 21.000 | 33.705 | 20.826 | 1.00 | 26.00 |
| ATOM | 1838 | O | HOH | 373 | 13.648 | 32.794 | 21.329 | 1.00 | 27.98 |
| ATOM | 1839 | O | HOH | 374 | 29.735 | 25.683 | 38.707 | 1.00 | 21.00 |
| ATOM | 1859 | O | HOH | 375 | 33.670 | 24.419 | 60.503 | 1.00 | 50.04 |
| ATOM | 1840 | O | HOH | 376 | 30.034 | 11.047 | 37.420 | 1.00 | 43.28 |
| ATOM | 1841 | O | HOH | 377 | 8.662 | 35.846 | 35.068 | 1.00 | 51.94 |
| ATOM | 1842 | O | HOH | 378 | 10.847 | 36.466 | 39.503 | 1.00 | 42.32 |
| ATOM | 1843 | O | HOH | 379 | 14.395 | 48.943 | 39.085 | 1.00 | 29.72 |
| ATOM | 1844 | O | HOH | 380 | 36.676 | 11.660 | 40.172 | 1.00 | 39.81 |
| ATOM | 1845 | O | HOH | 381 | 35.968 | 7.212 | 34.763 | 1.00 | 58.66 |
| ATOM | 1846 | O | HOH | 382 | 17.426 | 21.988 | 21.077 | 1.00 | 41.69 |
| ATOM | 1847 | O | HOH | 383 | 29.837 | 22.623 | 39.378 | 1.00 | 32.82 |
| ATOM | 1848 | O | HOH | 384 | 23.855 | 29.386 | 55.164 | 1.00 | 55.00 |
| ATOM | 1849 | O | HOH | 385 | 17.408 | 35.360 | 47.495 | 1.00 | 61.61 |
| ATOM | 1850 | O | HOH | 386 | 27.900 | 49.720 | 42.445 | 1.00 | 47.70 |
| ATOM | 1851 | O | HOH | 387 | 13.932 | 36.230 | 44.385 | 1.00 | 45.08 |
| ATOM | 1852 | O | HOH | 388 | 12.650 | 28.021 | 43.288 | 1.00 | 49.86 |
| ATOM | 1853 | O | HOH | 389 | 16.974 | 42.367 | 43.435 | 1.00 | 34.38 |
| ATOM | 1854 | O | HOH | 390 | 37.335 | 42.653 | 28.295 | 1.00 | 64.46 |
| ATOM | 1855 | O | HOH | 391 | 29.701 | 49.856 | 35.323 | 1.00 | 62.61 |
| ATOM | 1856 | O | HOH | 392 | 27.267 | 50.835 | 33.976 | 1.00 | 66.60 |
| ATOM | 1857 | O | HOH | 393 | 19.661 | 29.181 | 51.537 | 1.00 | 34.01 |
| ATOM | 1858 | O | HOH | 394 | 29.412 | 17.505 | 59.089 | 1.00 | 51.78 |
| TER | | | | | | | | | |
| END | | | | | | | | | |

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 716 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1..714

(xi) SEQUENCE DESCRIPTION: SEQ ID NO:1:

```
ATG AGT AAA GGA GAA GAA CTT TTC ACT GCA GTT GTC CCA ATT CTT GTT        48
Met Ser Lys Gly Glu Glu Leu Phe Thr Ala Val Val Pro Ile Leu Val
 1               5                  10                  15

GAA TTA GAT GGT GAT GTT AAT GGG CAC AAA TTT TCT GTC AGT GGA GAG        96
Glu Leu Asp Gly Asp Val Asn Gly His Lys Phe Ser Val Ser Gly Glu
             20                  25                  30

GGT GAA GGT GAT GTA ACA TAC GGA AAA CTT ACC CTT AAA TTT ATT TGC       144
Gly Glu Gly Asp Val Thr Tyr Gly Lys Leu Thr Leu Lys Phe Ile Cys
         35                  40                  45

ACT ACT GGA AAA CTA CCT GTT CCA TGG CCA ACA CTT GTC ACT ACT TTC       192
Thr Thr Gly Lys Leu Pro Val Pro Trp Pro Thr Leu Val Thr Thr Phe
     50                  55                  60

TCT TAT GGT GTT CAA TGC TTT TCA AGA TAC CCA GAT CAT ATG AAA CGG       240
Ser Tyr Gly Val Gln Cys Phe Ser Arg Tyr Pro Asp His Met Lys Arg
 65                  70                  75                  80

CAT GAC TTT TTC AAG AGT GCC ATG CCC GAA GGT TAT GTA CAG CAA AGA       288
His Asp Phe Phe Lys Ser Ala Met Pro Glu Gly Tyr Val Gln Gln Arg
                 85                  90                  95

ACT ATA TTT TTC AAA GAT GAC GGG AAC TAC AAG ACA CGT GCT GAA GTC       336
Thr Ile Phe Phe Lys Asp Asp Gly Asn Tyr Lys Thr Arg Ala Glu Val
            100                 105                 110

AAG TTT GAA GGT GAT ACC CTT GTT AAT AGA ATC GAG TTA AAA GGT ATT       384
Lys Phe Glu Gly Asp Thr Leu Val Asn Arg Ile Glu Leu Lys Gly Ile
        115                 120                 125

GAT TTT AAA GAA GAT GGA AAC ATT CTT GGA CAT AAA TTG GAA TAC AAC       432
Asp Phe Lys Glu Asp Gly Asn Ile Leu Gly His Lys Leu Glu Tyr Asn
    130                 135                 140

TAT AAC TCA CAC AAT GTA TAC ATC ATG GCA GAC AAA CAA AAG AAT GGA       480
```

```
Tyr Asn Ser His Asn Val Tyr Ile Met Ala Asp Lys Gln Lys Asn Gly
145                 150                 155                 160

ATC AAA GTT AAC TTC AAA ATT AGA CAC AAC ATT GAA GAT GGA AGC GTT     528
Ile Lys Val Asn Phe Lys Ile Arg His Asn Ile Glu Asp Gly Ser Val
            165                 170                 175

CAA CTA GCA GAC TAT TAT CAA CAA AAT ACT CCA ATT CTC GAT GGC CCT     576
Gln Leu Ala Asp Tyr Tyr Gln Gln Asn Thr Pro Ile Leu Asp Gly Pro
        180                 185                 190

GTC CTT TTA CCA GAC AAC CAT TAC CTG TCC ACA CAA TCT GCC CTT TCG     624
Val Leu Leu Pro Asp Asn His Tyr Leu Ser Thr Gln Ser Ala Leu Ser
            195                 200                 205

AAA GAT CCC AAC GAA AAG AGA GAC CAC ATG GTC CTT CTT GAG TTT GTA     672
Lys Asp Pro Asn Glu Lys Arg Asp His Met Val Leu Leu Glu Phe Val
        210                 215                 220

ACA GCT GCT GGG ATT ACA CAT GGC ATG GAT GAA CTA TAC AAA             714
Thr Ala Ala Gly Ile Thr His Gly Met Asp Glu Leu Tyr Lys
225                 230                 235

TA                                                                  716

(2) INFORMATION FOR SEQ ID NO:2:

(i) SEQUENCE CHARACTERISTICS:
        (A) LENGTH: 238 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Lys Gly Glu Glu Leu Phe Thr Ala Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Val Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Gln Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp Tyr Tyr Gln Gln Asn Thr Pro Ile Leu Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220
```

```
Thr Ala Ala Gly Ile Thr His Gly Met Asp Glu Leu Tyr Lys
225                 230                 235
```

(2) INFORMATION FOR SEQ ID NO:3:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..720

(xi) SEQUENCE DESCRIPTION: SEQ ID NO:3:

```
ATG GTG AGC AAG GGC GAG GAG CTG TTC ACC GGG GTG GTG CCC ATC CTG      48
Met Val Ser Lys Gly Glu Glu Leu Phe Thr Gly Val Val Pro Ile Leu
    240                 245                 250

GTC GAG CTG GAC GGC GAC GTA AAC GGC CAC AAG TTC AGC GTG TCC GGC      96
Val Glu Leu Asp Gly Asp Val Asn Gly His Lys Phe Ser Val Ser Gly
255                 260                 265                 270

GAG GGC GAG GGC GAT GCC ACC TAC GGC AAG CTG ACC CTG AAG TTC ATC     144
Glu Gly Glu Gly Asp Ala Thr Tyr Gly Lys Leu Thr Leu Lys Phe Ile
                275                 280                 285

TGC ACC ACC GGC AAG CTG CCC GTG CCC TGG CCC ACC CTC GTG ACC ACC     192
Cys Thr Thr Gly Lys Leu Pro Val Pro Trp Pro Thr Leu Val Thr Thr
            290                 295                 300

TTC GGC TAC GGC GTG CAG TGC TTC GCC CGC TAC CCC GAC CAC ATG AAG     240
Phe Gly Tyr Gly Val Gln Cys Phe Ala Arg Tyr Pro Asp His Met Lys
        305                 310                 315

CAG CAG GAC TTC TTC AAG TCC GCC ATG CCC GAA GGC TAC GTC CAG GAG     288
Gln Gln Asp Phe Phe Lys Ser Ala Met Pro Glu Gly Tyr Val Gln Glu
    320                 325                 330

CGC ACC ATC TTC TTC AAG GAC GAC GGC AAC TAC AAG ACC CGC GCC GAG     336
Arg Thr Ile Phe Phe Lys Asp Asp Gly Asn Tyr Lys Thr Arg Ala Glu
335                 340                 345                 350

GTG AAG TTC GAG GGC GAC ACC CTG GTG AAC CGC ATC GAG CTG AAG GGC     384
Val Lys Phe Glu Gly Asp Thr Leu Val Asn Arg Ile Glu Leu Lys Gly
                355                 360                 365

ATC GAC TTC AAG GAC GAC GGC AAC ATC CTG GGG CAC AAG CTG GAG TAC     432
Ile Asp Phe Lys Asp Asp Gly Asn Ile Leu Gly His Lys Leu Glu Tyr
            370                 375                 380

AAC TAC AAC AGC CAC AAC GTC TAT ATC ATG GCC GAC AAG CAG AAG AAC     480
Asn Tyr Asn Ser His Asn Val Tyr Ile Met Ala Asp Lys Gln Lys Asn
        385                 390                 395

GGC ATC AAG GTG AAC TTC AAG ATC CGC CAC AAC ATC GAG GAC GGC AGC     528
Gly Ile Lys Val Asn Phe Lys Ile Arg His Asn Ile Glu Asp Gly Ser
    400                 405                 410

GTG CAG CCC GCC GAC CAC TAC CAG CAG AAC ACC CCC ATC GGC GAC GGC     576
Val Gln Pro Ala Asp His Tyr Gln Gln Asn Thr Pro Ile Gly Asp Gly
415                 420                 425                 430

CCC GTG CTG CTG CCC GAC AAC CAC TAC CTG AGC TAC CAG TCC GCC CTG     624
Pro Val Leu Leu Pro Asp Asn His Tyr Leu Ser Tyr Gln Ser Ala Leu
                435                 440                 445

AGC AAA GAC CCC AAC GAG AAG CGC GAT CAC ATG GTC CTG CTG GAG TTC     672
Ser Lys Asp Pro Asn Glu Lys Arg Asp His Met Val Leu Leu Glu Phe
            450                 455                 460

GTG ACC GCC GCC GGG ATC ACT CAC GGC ATG GAC GAG CTG TAC AAG TAA     720
Val Thr Ala Ala Gly Ile Thr His Gly Met Asp Glu Leu Tyr Lys  *
        465                 470                 475
```

```
(2) INFORMATION FOR SEQ ID NO:4:

(i) SEQUENCE CHARACTERISTICS:
        (A) LENGTH:  239 amino acids
        (B) TYPE: amino acid
        (D) TOPOLOGY: linear (ii) MOLECULE TYPE: protein (xi) SEQUENCE DESCRIPTION: SEQ ID NO:4:

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
        50                  55                  60

Phe Gly Tyr Gly Val Gln Cys Phe Ala Arg Tyr Pro Asp His Met Lys
 65                  70                  75                  80

Gln Gln Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
               100                 105                 110

Val Lys Phe Glu Gly Asp Thr Leu Val Asn Arg Ile Glu Leu Lys Gly
           115                 120                 125

Ile Asp Phe Lys Asp Asp Gly Asn Ile Leu Gly His Lys Leu Glu Tyr
       130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
               165                 170                 175

Val Gln Pro Ala Asp His Tyr Gln Gln Asn Thr Pro Ile Gly Asp Gly
           180                 185                 190

Pro Val Leu Leu Pro Asp Asn His Tyr Leu Ser Tyr Gln Ser Ala Leu
       195                 200                 205

Ser Lys Asp Pro Asn Glu Lys Arg Asp His Met Val Leu Leu Glu Phe
   210                 215                 220

Val Thr Ala Ala Gly Ile Thr His Gly Met Asp Glu Leu Tyr Lys
225                 230                 235                 240
```

LONG WAVELENGTH ENGINEERED FLUORESCENT PROTEINS

This application is a continuation of and claims priority under 35 U.S.C. § 120 to U.S. patent application Ser. No. 08/974,737, filed Nov. 19, 1997, now U.S. Pat. No. 6,077,707, which is a continuation of U.S. patent application Ser. No. 08/911,825, filed Aug. 15, 1997, now U.S. Pat. No. 6,054,321, which is a continuation-in-part of U.S. patent application Ser. No. 08/706,408, filed Aug. 30, 1996, now U.S. Pat. No. 6,124,128, which claims priority to Provisional Application Ser. No. 60/024,050, filed Aug. 16, 1996, the entire contents of which are hereby incorporated by reference herein.

This invention was made in part with Government support under grant no. MCB 9418479 awarded by the National Science Foundation. The Government may have rights in this invention.

BACKGROUND OF THE INVENTION

Fluorescent molecules are attractive as reporter molecules in many assay systems because of their high sensitivity and ease of quantification. Recently, fluorescent proteins have been the focus of much attention because they can be produced in vivo by biological systems, and can be used to trace intracellular events without the need to be introduced into the cell through microinjection or permeabilization. The green fluorescent protein of *Aequorea victoria* is particularly interesting as a fluorescent protein. A cDNA for the protein has been cloned. (D. C. Prasher et al., "Primary structure of the *Aequorea victoria* green-fluorescent protein," *Gene* (1992) 111:229–33.) Not only can the primary amino acid sequence of the protein be expressed from the cDNA, but the expressed protein can fluoresce. This indicates that the protein can undergo the cyclization and oxidation believed to be necessary for fluorescence. Aequorea green fluorescent protein ("GFP") is a stable, proteolysis-resistant single chain of 238 residues and has two absorption maxima at around 395 and 475 nm. The relative amplitudes of these two peaks is sensitive to environmental factors (W. W. Ward. *Bioluminescence and Chemiluminescence* (M. A. DeLuca and W. D. McElroy, eds) Academic Press pp.235–242 (1981); W. W. Ward & S. H. Bokman Biochemistry 21:4535–4540 (1982); W. W. Ward et al. *Photochem. Photobiol.* 35:803–808 (1982)) and illumination history (A. B. Cubitt et al. *Trends Biochem. Sci.* 20:448–455 (1995)), presumably reflecting two or more ground states. Excitation at the primary absorption peak of 395 nm yields an emission maximum at 508 nm with a quantum yield of 0.72–0.85 (O. Shimomura and F. H. Johnson *J. Cell. Comp. Physiol* 59:223 (1962); J. G. Morin and J. W. Hastings, *J. Cell. Physiol.* 77:313 (1971); H. Morise et al. *Biochemistry* 13:2656 (1974); W. W. Ward *Photochem. Photobiol. Reviews* (Smith, K. C. ed.) 4:1 (1979); A. B. Cubitt et al. *Trends Biochem. Sci.* 20:448–455 (1995); D. C. Prasher *Trends Genet.* 11:320–323 (1995); M. Chalfie *Photochem. Photobiol.* 62:651–656 (1995); W. W. Ward. *Bioluminescence and Chemiluminescence* (M. A. DeLuca and W. D. McElroy, eds) Academic Press pp. 235–242 (1981); W. W. Ward & S. H. Bokman *Biochemistry* 21:4535–4540 (1982); W. W. Ward et al. *Photochem. Photobiol.* 35:803–808 (1982)). The fluorophore results from the autocatalytic cyclization of the polypeptide backbone between residues Ser$^{65}$ and Gly$^{67}$ and oxidation of the α-β bond of Tyr$^{66}$ (A. B. Cubitt et al. *Trends Biochem. Sci.* 20:448–455 (1995); C. W. Cody et al. *Biochemisty* 32:1212–1218 (1993); R. Heim et al. *Proc. Natl. Acad. Sci. USA* 91:12501–12504 (1994)). Mutation of Ser$^{65}$ to Thr (S65T) simplifies the excitation spectrum to a single peak at 488 nm of enhanced amplitude (R. Heim et al. *Nature* 373:664–665 (1995)), which no longer gives signs of conformational isomers (A. B. Cubitt et al. *Trends Biochem. Sci.* 20:448–455 (1995)).

Fluorescent proteins have been used as markers of gene expression, tracers of cell lineage and as fusion tags to monitor protein localization within living cells. (M. Chalfie et al., "Green fluorescent protein as a marker for gene expression," *Science* 263:802–805; A. B. Cubitt et al., "Understanding, improving and using green fluorescent proteins," *TIBS* 20, November 1995, pp. 448–455. U.S. Pat. No. 5,491,084, M. Chalfie and D. Prasher. Furthermore, engineered versions of Aequorea green fluorescent protein have been identified that exhibit altered fluorescence characteristics, including altered excitation and emission maxima, as well as excitation and emission spectra of different shapes. (R. Heim et al., "Wavelength mutations and posttranslational autoxidation of green fluorescent protein," *Proc. Natl. Acad. Sci. USA,* (1994) 91:12501–04; R. Heim et al., "Improved green fluorescence," *Nature* (1995) 373:663–665.) These properties add variety and utility to the arsenal of biologically based fluorescent indicators.

There is a need for engineered fluorescent proteins with varied fluorescent properties.

BRIEF DESCRIPTION OF THE DRAWINGS

FIG. 3 depicts the nucleotide sequence (SEQ ID NO:1) and deduced amino acid sequence (SEQ ID NO:2) of an Aequorea green fluorescent protein.

FIG. 4 depicts the nucleotide sequence (SEQ ID NO:3) and deduced amino acid sequence (SEQ ID NO:4) of the engineered Aequorea-related fluorescent protein S65G/S72A/T203Y utilizing preferred mammalian codons and optimal Kozak sequence.

FIGS. 5-A to 5-AT present the coordinates for the crystal structure of Aequorea-related green fluorescent protein S65T.

SUMMARY OF THE INVENTION

Figure 1A:
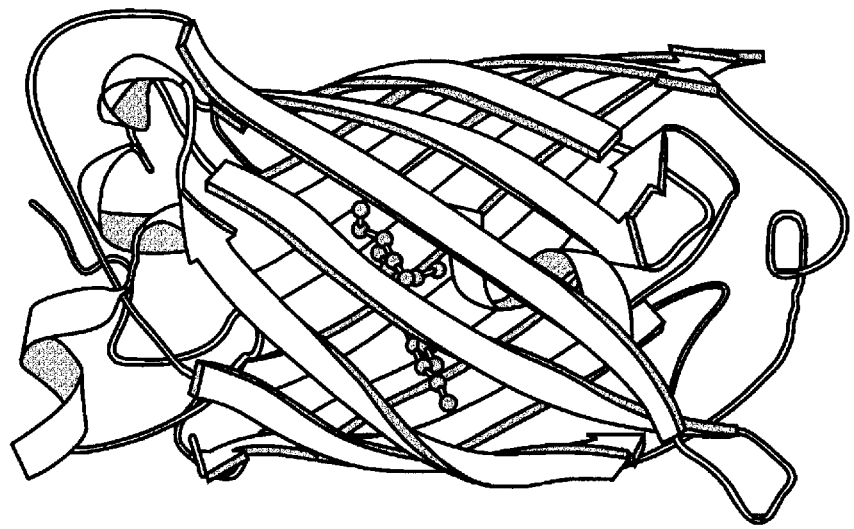
FIGS. 1A–1B. (A) Schematic drawing of the backbone of GFP produced by Molscript (J. P. Kraulis, *J. Appl. Cryst.,* 24:946 (1991)). The chromophore is shown as a ball and stick model. (B) Schematic drawing of the overall fold of GFP. Approximate residue numbers mark the beginning and ending of the secondary structure elements.

This invention provides functional engineered fluorescent proteins with varied fluorescence characteristics that can be easily distinguished from currently existing green and blue fluorescent proteins. Such engineered fluorescent proteins enable the simultaneous measurement of two or more processes within cells and can be used as fluorescence energy donors or acceptors when used to monitor protein-protein interactions through FRET. Longer wavelength engineered fluorescent proteins are particularly useful because photodynamic toxicity and auto-fluorescence of cells are significantly reduced at longer wavelengths. In particular, the introduction of the substitution T203X, wherein X is an aromatic amino acid, results in an increase in the excitation and emission wavelength maxima of Aequorea-related fluorescent proteins.

In one aspect, this invention provides a nucleic acid molecule comprising a nucleotide sequence encoding a functional engineered fluorescent protein whose amino acid sequence is substantially identical to the amino acid sequence of Aequorea green fluorescent protein (SEQ ID NO:2) and which differs from SEQ ID NO:2 by at least an amino acid substitution located no more than about 0.5 nm from the chromophore of the engineered fluorescent protein, wherein the substitution alters the electronic environment of the chromophore, whereby the functional engineered fluorescent protein has a different fluorescent property than Aequorea green fluorescent protein.

In one aspect this invention provides a nucleic acid molecule comprising a nucleotide sequence encoding a functional engineered fluorescent protein whose amino acid sequence is substantially identical to the amino acid sequence of Aequorea green fluorescent protein (SEQ ID NO:2) and which differs from SEQ ID NO:2 by at least a substitution at T203 and, in particular, T203X, wherein X is an aromatic amino acid selected from H, Y, W or F, said functional engineered fluorescent protein having a different fluorescent property than Aequorea green fluorescent protein. In one embodiment, the amino acid sequence further comprises a substitution at S65, wherein the substitution is selected from S65G, S65T, S65A, S65L, S65C, S65V and S65I. In another embodiment, the amino acid sequence differs by no more than the substitutions S65T/T203H; S65T/T203Y; S72A/F64L/S65G/T203Y; S65G/V68L/Q69K/S72A/T203Y; S72A/S65G/V68L/T203Y; S65G/S72A/T203Y; or S65G/S72A/T203W. In another embodiment, the amino acid sequence further comprises a substitution at Y66, wherein the substitution is selected from Y66H, Y66F, and Y66W. In another embodiment, the amino acid sequence further comprises a mutation from Table A. In another embodiment, the amino acid sequence further comprises a folding mutation. In another embodiment, the nucleotide sequence encoding the protein differs from the nucleotide sequence of SEQ ID NO:1 by the substitution of at least one codon by a preferred mammalian codon. In another embodiment, the nucleic acid molecule encodes a fusion protein wherein the fusion protein comprises a polypeptide of interest and the functional engineered fluorescent protein.

In another aspect, this invention provides a nucleic acid molecule comprising a nucleotide sequence encoding a functional engineered fluorescent protein whose amino acid sequence is substantially identical to the amino acid sequence of Aequorea green fluorescent protein (SEQ ID NO:2) and which differs from SEQ ID NO:2 by at least an amino acid substitution at L42, V61, T62, V68, Q69, Q94, N121, Y145, H148, V150, F165, I167, Q183, N185, L220, E222 (not E222G), or V224, said functional engineered fluorescent protein having a different fluorescent property than Aequorea green fluorescent protein. In one embodiment, amino acid substitution is:

L42X, wherein X is selected from C, F, H, W and Y,
V61X, wherein X is selected from F, Y, H and C,
T62X, wherein X is selected from A, V, F, S, D, N, Q, Y, H and C,
V68X, wherein X is selected from F, Y and H,
Q69X, wherein X is selected from K, R, E and G,
Q94X, wherein X is selected from D, E, H, K and N,
N121X, wherein X is selected from F, H, W and Y,
Y145X, wherein X is selected from W, C, F, L, E, H, K and Q,
H148X, wherein X is selected from F, Y, N, K, Q and R,
V150X, wherein X is selected from F, Y and H,
F165X, wherein X is selected from H, Q, W and Y,
I167X, wherein X is selected from F, Y and H,
Q183X, wherein X is selected from H, Y, E and K,
N185X, wherein X is selected from D, E, H, K and Q,
L220X, wherein X is selected from H, N, Q and T,
E222X, wherein X is selected from N and Q, or
V224X, wherein X is selected from H, N, Q, T, F, W and Y.

In a further aspect, this invention provides an expression vector comprising expression control sequences operatively linked to any of the aforementioned nucleic acid molecules. In a further aspect, this invention provides a recombinant host cell comprising the aforementioned expression vector.

In another aspect, this invention provides a functional engineered fluorescent protein whose amino acid sequence is substantially identical to the amino acid sequence of Aequorea green fluorescent protein (SEQ ID NO:2) and which differs from SEQ ID NO:2 by at least an amino acid substitution located no more than about 0.5 nm from the chromophore of the engineered fluorescent protein, wherein the substitution alters the electronic environment of the chromophore, whereby the functional engineered fluorescent protein has a different fluorescent property than Aequorea green fluorescent protein.

In another aspect, this invention provides a functional engineered fluorescent protein whose amino acid sequence is substantially identical to the amino acid sequence of Aequorea green fluorescent protein (SEQ ID NO:2) and which differs from SEQ ID NO:2 by at least the amino acid substitution at T203, and in particular, T203X, wherein X is an aromatic amino acid selected from H, Y, W or F, said functional engineered fluorescent protein having a different fluorescent property than Aequorea green fluorescent protein. In one embodiment, the amino acid sequence further comprises a substitution at S65, wherein the substitution is selected from S65G, S65T, S65A, S65L, S65C, S65V and S65I. In another embodiment, the amino acid sequence differs by no more than the substitutions S65T/T203H; S65T/T203Y; S72A/F64L/S65G/T203Y; S72A/S65G/V68L/T203Y; S65G/V68L/Q69K/S72A/T203Y; S65G/S72A/T203Y; or S65G/S72A/T203W. In another embodiment, the amino acid sequence further comprises a substitution at Y66, wherein the substitution is selected from Y66H, Y66F, and Y66W. In another embodiment, the amino acid sequence further comprises a folding mutation. In another embodiment, the engineered fluorescent protein is part of a fusion protein wherein the fusion protein comprises a polypeptide of interest and the functional engineered fluorescent protein.

In another aspect this invention provides a functional engineered fluorescent protein whose amino acid sequence is substantially identical to the amino acid sequence of Aequorea green fluorescent protein (SEQ ID NO:2) and which differs from SEQ ID NO:2 by at least an amino acid substitution at L42, V61, T62, V68, Q69, Q94, N121, Y145, H148, V150, F165, I167, Q183, N185, L220, E222, or V224, said functional engineered fluorescent protein having a different fluorescent property than Aequorea green fluorescent protein.

In another aspect, this invention provides a fluorescently labelled antibody comprising an antibody coupled to any of the aforementioned functional engineered fluorescent proteins. In one embodiment, the fluorescently labelled antibody is a fusion protein wherein the fusion protein comprises the antibody fused to the functional engineered fluorescent protein.

In another aspect, this invention provides a nucleic acid molecule comprising a nucleotide sequence encoding an antibody fused to a nucleotide sequence encoding a functional engineered fluorescent protein of this invention.

In another aspect, this invention provides a fluorescently labelled nucleic acid probe comprising a nucleic acid probe coupled to a functional engineered fluorescent protein whose amino acid sequence of this invention. The fusion can be through a linker peptide.

In another aspect, this invention provides a method for determining whether a mixture contains a target comprising contacting the mixture with a fluorescently labelled probe comprising a probe and a functional engineered fluorescent protein of this invention; and determining whether the target has bound to the probe. In one embodiment, the target molecule is captured on a solid matrix.

In another aspect, this invention provides a method for engineering a functional engineered fluorescent protein having a fluorescent property different than Aequorea green fluorescent protein, comprising substituting an amino acid that is located no more than 0.5 nm from any atom in the chromophore of an Aequorea-related green fluorescent protein with another amino acid; whereby the substitution alters a fluorescent property of the protein. In one embodiment, the amino acid substitution alters the electronic environment of the chromophore.

In another aspect, this invention provides a method for engineering a factional engineered fluorescent protein having a different fluorescent property than Aequorea green fluorescent protein comprising substituting amino acids in a loop domain of an Aequorea-related green fluorescent protein with amino acids so as to create a consensus sequence for phosphorylation or for proteolysis.

In another aspect, this invention provides a method for producing fluorescence resonance energy transfer comprising providing a donor molecule comprising a functional engineered fluorescent protein this invention; providing an appropriate acceptor molecule for the fluorescent protein; and bringing the donor molecule and the acceptor molecule into sufficiently close contact to allow fluorescence resonance energy transfer.

In another aspect, this invention provides a method for producing fluorescence resonance energy transfer comprising providing an acceptor molecule comprising a functional engineered fluorescent protein of this invention; providing an appropriate donor molecule for the fluorescent protein; and bringing the donor molecule and the acceptor molecule into sufficiently close contact to allow fluorescence resonance energy transfer. In one embodiment, the donor molecule is a engineered fluorescent protein whose amino acid sequence comprises the substitution T203I and the acceptor molecule is an engineered fluorescent protein whose amino acid sequence comprises the substitution T203X, wherein X is an aromatic amino acid selected from H, Y, W or F, said functional engineered fluorescent protein having a different fluorescent property than Aequorea green fluorescent protein.

In another aspect, this invention provides a crystal of a protein comprising a fluorescent protein with an amino acid sequence substantially identical to SEQ ID NO: 2, wherein said crystal diffracts with at least a 2.0 to 3.0 angstrom resolution.

In another embodiment, this invention provides computational method of designing a fluoresent protein comprising determining from a three dimensional model of a crystallized fluorescent protein comprising a fluorescent protein with a bound ligand, at least one interacting amino acid of the fluorescent protein that interacts with at least one first chemical moiety of the ligand, and selecting at least one chemical modification of the first chemical moiety to produce a second chemical moiety with a structure to either decrease or increase an interaction between the interacting amino acid and the second chemical moiety compared to the interaction between the interacting amino acid and the first chemical moiety.

In another embodiment, this invention provides a computational method of modeling the three dimensional structure of a fluorescent protein comprising determining a three dimensional relationship between at least two atoms listed in the atomic coordinates of FIGS. 5-A to 5-AT.

In another embodiment, this invention provides a device comprising a storage device and, stored in the device, at least 10 atomic coordinates selected from the atomic coordinates listed in FIGS. 5-A to 5AT. In one embodiment, the storage device is a computer readable device that stores code that receives as input the atomic coordinates. In another embodiment, the computer readable device is a floppy disk or a hard drive.

DETAILED DESCRIPTION OF THE INVENTION

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. For purposes of the present invention, the following terms are defined below.

"Binding pair" refers to two moieties (e.g. chemical or biochemical) that have an affinity for one another. Examples of binding pairs include antigen/antibodies, lectin/avidin, target polynucleotide/probe oligonucleotide, antibody/anti-antibody, receptor/ligand, enzyme/ligand and the like. "One member of a binding pair" refers to one moiety of the pair, such as an antigen or ligand.

"Nucleic acid" refers to a deoxyribonucleotide or ribonucleotide polymer in either single- or double-stranded form, and, unless otherwise limited, encompasses known analogs of natural nucleotides that can function in a similar manner as naturally occurring nucleotides. It will be understood that when a nucleic acid molecule is represented by a DNA sequence, this also includes RNA molecules having the corresponding RNA sequence in which "U" replaces "T."

"Recombinant nucleic acid molecule" refers to a nucleic acid molecule which is not naturally occurring, and which comprises two nucleotide sequences which are not naturally joined together. Recombinant nucleic acid molecules are produced by artificial recombination, e.g., genetic engineering techniques or chemical synthesis.

Reference to a nucleotide sequence "encoding" a polypeptide means that the sequence, upon transcription and translation of mRNA, produces the polypeptide. This includes both the coding strand, whose nucleotide sequence is identical to mRNA and whose sequence is usually provided in the sequence listing, as well as its complementary strand, which is used as the template for transcription. As any person skilled in the art recognizes, this also includes all degenerate nucleotide sequences encoding the same amino acid sequence. Nucleotide sequences encoding a polypeptide include sequences containing introns.

"Expression control sequences" refers to nucleotide sequences that regulate the expression of a nucleotide sequence to which they are operatively linked. Expression control sequences are "operatively linked" to a nucleotide sequence when the expression control sequences control and regulate the transcription and, as appropriate, translation of the nucleotide sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

"Naturally-occurring" as used herein, as applied to an object, refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

"Control sequence" refers to polynucleotide sequences which are necessary to effect the expression of coding and non-coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, components whose presence can influence expression, and can also include additional components whose presence is advantageous, for example, leader sequences and fusion partner sequences.

"Isolated polynucleotide" refers a polynucleotide of genomic, cDNA, or synthetic origin or some combination there of, which by virtue of its origin the "isolated polynucleotide" (1) is not associated with the cell in which the "isolated polynucleotide" is found in nature, or (2) is operably linked to a polynucleotide which it is not linked to in nature.

"Polynucleotide" refers to a polymeric form of nucleotides of at least 10 bases in length, either ribonucleotides or deoxynucleotides or a modified form of either type of nucleotide. The term includes single and double stranded forms of DNA.

The term "probe" refers to a substance that specifically binds to another substance (a "target"). Probes include, for example, antibodies, nucleic acids, receptors and their ligands.

"Modulation" refers to the capacity to either enhance or inhibit a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "modulator" refers to a chemical (naturally occurring or non-naturally occurring), such as a synthetic molecule (e.g., nucleic acid, protein, non-peptide, or organic molecule), or an extract made from biological materials such as bacteria, plants, fungi, or animal (particularly mammalian) cells or tissues. Modulators can be evaluated for potential activity as inhibitors or activators (directly or indirectly) of a biological process or processes (e.g., agonist, partial antagonist, partial agonist, inverse agonist, antagonist, antineoplastic agents, cytotoxic agents, inhibitors of neoplastic transformation or cell proliferation, cell proliferation-promoting agents, and the like) by inclusion in screening assays described herein. The activity of a modulator may be known, unknown or partially known.

The term "test chemical" refers to a chemical to be tested by one or more screening method(s) of the invention as a putative modulator. A test chemical is usually not known to bind to the target of interest. The term "control test chemical" refers to a chemical known to bind to the target (e.g,. a known agonist, antagonist, partial agonist or inverse agonist). Usually, various predetermined concentrations of test chemicals are used for screening, such as 0.01 $\mu$M, 0.1 $\mu$M, 1.0 $\mu$M, and 10.0 $\mu$M.

The term "target" refers to a biochemical entity involved a biological process. Targets are typically proteins that play a useful role in the physiology or biology of an organism. A therapeutic chemical binds to target to alter or modulate its function. As used herein targets can include cell surface receptors, G-proteins, kinases, ion channels, phopholipases and other proteins mentioned herein.

The term "label" refers to a composition detectable by spectroscopic, photochemical, biochemical, immunochemical, or chemical means. For example, useful labels include $^{32}$P, fluorescent dyes, fluorescent proteins, electron-dense reagents, enzymes (e.g., as commonly used in an ELISA), biotin, dioxigenin, or haptens and proteins for which antisera or monoclonal antibodies are available. For example, polypeptides of this invention can be made as detectible labels, by e.g., incorporating a them as into a polypeptide, and used to label antibodies specifically reactive with the polypeptide. A label often generates a measurable signal, such as radioactivity, fluorescent light or enzyme activity, which can be used to quantitate the amount of bound label.

The term "nucleic acid probe" refers to a nucleic acid molecule that binds to a specific sequence or sub-sequence of another nucleic acid molecule. A probe is preferably a nucleic acid molecule that binds through complementary base pairing to the full sequence or to a sub-sequence of a target nucleic acid. It will be understood that probes may bind target sequences lacking complete complementarity with the probe sequence depending upon the stringency of the hybridization conditions. Probes are preferably directly labelled as with isotopes, chromophores, lumiphores, chromogens, fluorescent proteins, or indirectly labelled such as with biotin to which a streptavidin complex may later bind. By assaying for the presence or absence of the probe, one can detect the presence or absence of the select sequence or sub-sequence.

A "labeled nucleic acid probe" is a nucleic acid probe that is bound, either covalently, through a linker, or through ionic, van der Waals or hydrogen bonds to a label such that the presence of the probe may be detected by detecting the presence of the label bound to the probe.

The terms "polypeptide" and "protein" refers to a polymer of amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "recombinant host cell" refers to a cell that comprises a recombinant nucleic acid molecule. Thus, for example, recombinant host cells can express genes that are not found within the native (non-recombinant) form of the cell.

The terms "isolated" "purified" or "biologically pure" refer to material which is substantially or essentially free from components which normally accompany it as found in its native state. Purity and homogeneity are typically determined using analytical chemistry techniques such as polyacrylamide gel electrophoresis or high performance liquid chromatography. A protein or nucleic acid molecule which is the predominant protein or nucleic acid species present in a preparation is substantially purified. Generally, an isolated protein or nucleic acid molecule will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies.

The term "immunoassay" refers to an assay that utilizes an antibody to specifically bind an analyte. The immunoassay is characterized by the use of specific binding properties of a particular antibody to isolate, target, and/or quantify the analyte.

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers and Miller, Computer Applic. Biol. Sci., 4: 11–17 (1988); Smith and Waterman (1981) *Adv. Appl. Math.* 2: 482; Needleman and Wunsch (1970) *J. Mol. Biol.* 48: 443; Pearson and Lipman (1988) *Proc. Natl. Acad. Sci. USA* 85: 2444; Higgins and Sharp (1988) *Gene,* 73: 237–244 and Higgins and Sharp (1989) *CABIOS* 5: 151–153; Corpet, et al. (1988) *Nucleic Acids Research* 16, 10881–90; Huang, et al. (1992) *Computer Applications in the Biosciences* 8, 155–65, and Pearson, et al. (1994) *Methods in Molecular Biology* 24, 307–31. Alignment is also often performed by inspection and manual alignment.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative amino acid substitutions providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);

4) Arginine (R), Lysine (K);
5) Isoleucine (I), Leucine (L), Methionine (M), Valine (V); and
6) Phenylalanine (F), Tyrosine (Y), Tryptophan (W).

The term "complementary" means that one nucleic acid molecule has the sequence of the binding partner of another nucleic acid molecule. Thus, the sequence 5'-ATGC-3' is complementary to the sequence 5'-GCAT-3'.

An amino acid sequence or a nucleotide sequence is "substantially identical" or "substantially similar" to a reference sequence if the amino acid sequence or nucleotide sequence has at least 80% sequence identity with the reference sequence over a given comparison window. Thus, substantially similar sequences include those having, for example, at least 85% sequence identity, at least 90% sequence identity, at least 95% sequence identity or at least 99% sequence identity. Two sequences that are identical to each other are, of course, also substantially identical.

A subject nucleotide sequence is "substantially complementary" to a reference nucleotide sequence if the complement of the subject nucleotide sequence is substantially identical to the reference nucleotide sequence.

The term "stringent conditions" refers to a temperature and ionic conditions used in nucleic acid hybridization. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

The term "allelic variants" refers to polymorphic forms of a gene at a particular genetic locus, as well as cDNAs derived from mRNA transcripts of the genes and the polypeptides encoded by them.

The term "preferred mammalian codon" refers to the subset of codons from among the set of codons encoding an amino acid that are most frequently used in proteins expressed in mammalian cells as chosen from the following list:

| Amino Acid | Preferred codons for high level mammalian expression |
|---|---|
| Gly | GGC, GGG |
| Glu | GAG |
| Asp | GAC |
| Val | GUG, GUC |
| Ala | GCC, GCU |
| Ser | AGC, UCC |
| Lys | AAG |
| Asn | AAC |
| Met | AUG |
| Ile | AUC |
| Thr | ACC |
| Trp | UGG |
| Cys | UGC |
| Tyr | UAU, UAC |
| Leu | CUG |
| Phe | UUC |
| Arg | CGC, AGG, AGA |
| Gln | CAG |
| His | CAC |
| Pro | CCC |

Fluorescent molecules are useful in fluorescence resonance energy transfer ("FRET"). FRET involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should likewise be as high as possible to maximize $R_0$, the distance at which energy transfer efficiency is 50%. However, the excitation spectra of the donor and acceptor should overlap as little as possible so that a wavelength region can be found at which the donor can be excited efficiently without directly exciting the acceptor. Fluorescence arising from direct excitation of the acceptor is difficult to distinguish from fluorescence arising from FRET. Similarly, the emission spectra of the donor and acceptor should overlap as little as possible so that the two emissions can be clearly distinguished. High fluorescence quantum yield of the acceptor moiety is desirable if the emission from the acceptor is to be measured either as the sole readout or as part of an emission ratio. One factor to be considered in choosing the donor and acceptor pair is the efficiency of fluorescence resonance energy transfer between them. Preferably, the efficiency of FRET between the donor and acceptor is at least 10%, more preferably at least 50% and even more preferably at least 80%.

The term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between wild-type Aequorea GFP and the mutant form is useful. A measurable difference can be determined by determining the amount of any quantitative fluorescent property, e.g., the amount of fluorescence at a particular wavelength, or the integral of fluorescence over the emission spectrum. Determining ratios of excitation amplitude or emission amplitude at two different wavelengths ("excitation amplitude ratioing" and "emission amplitude ratioing", respectively) are particularly advantageous because the ratioing process provides an internal reference and cancels out variations in the absolute brightness of the excitation source, the sensitivity of the detector, and light scattering or quenching by the sample.

II. Long Wavelength Engineered Fluorescent Proteins

A. Fluorescent Proteins

As used herein, the term "fluorescent protein" refers to any protein capable of fluorescence when excited with appropriate electromagnetic radiation. This includes fluorescent proteins whose amino acid sequences are either naturally occurring or engineered (i.e., analogs or mutants). Many cnidarians use green fluorescent proteins ("GFPs") as energy-transfer acceptors in bioluminescence. A "green fluorescent protein," as used herein, is a protein that fluoresces green light. Similarly, "blue fluorescent proteins" fluoresce blue light and "red fluorescent proteins" fluoresce red light. GFPs have been isolated from the Pacific Northwest jellyfish, *Aequorea victoria*, the sea pansy, *Renilla reniformis*, and *Phialidium gregarium*. W. W. Ward et al., *Photochem. Photobiol.*, 35:803–808 (1982); L. D. Levine et al., *Comp. Biochem. Physiol.*, 72B:77–85 (1982).

A variety of Aequorea-related fluorescent proteins having useful excitation and emission spectra have been engineered by modifying the amino acid sequence of a naturally occurring GFP from *Aequorea Victoria*. (D. C. Prasher et al., Gene, 111:229–233 (1992); R. Heim et al., Proc. Natl. Acad. Sci., USA, 91:12501–04 (1994); U.S. patent application Ser. No. 08/337,915, filed Nov. 10, 1994; International application PCT/US95/14692, filed Nov. 10, 1995.)

As used herein, a fluorescent protein is an "Aequorea-related fluorescent protein" if any contiguous sequence of 150 amino acids of the fluorescent protein has at least 85% sequence identity with an amino acid sequence, either contiguous or non-contiguous, from the 238 amino-acid wild-type Aequorea green fluorescent protein of FIG. 3 (SEQ ID NO:2). More preferably, a fluorescent protein is Aequorea-related fluorescent protein if any contiguous sequence of 200 amino acids of the fluorescent protein has at least 95% sequence identity with an amino acid sequence, either contiguous or non-contiguous, from the wild type Aequorea green fluorescent protein of FIG. 3 (SEQ ID NO:2). Similarly, the fluorescent protein may be related to Renilla or Phialidium wild-type fluorescent proteins using the same standards.

Aequorea-related fluorescent proteins include, for example and without limitation, wild-type (native) *Aequorea victoria* GFP (D. C. Prasher et al., "Primary structure of the *Aequorea victoria* green fluorescent protein," Gene, (1992) 111:229–33), whose nucleotide sequence (SEQ ID NO:1) and deduced amino acid sequence (SEQ ID NO:2) are presented in FIG. 3; allelic variants of this sequence, e.g., Q80R, which has the glutamine residue at position 80 substituted with arginine (M. Chalfie et al., Science, (1994) 263:802–805); those engineered Aequorea-related fluorescent proteins described herein, e.g., in Table A or Table F, variants that include one or more folding mutations and fragments of these proteins that are fluorescent, such as Aequorea green fluorescent protein from which the two amino-terminal amino acids have been removed. Several of these contain different aromatic amino acids within the central chromophore and fluoresce at a distinctly shorter wavelength than wild type species. For example, engineered proteins P4 and P4-3 contain (in addition to other mutations) the substitution Y66H, whereas W2 and W7 contain (in addition to other mutations) Y66W. Other mutations both close to the chromophore region of the protein and remote from it in primary sequence may affect the spectral properties of GFP and are listed in the first part of the table below.

TABLE A

| Clone | Mutation(s) | Excitation max (nm) | Emission max (nm) | Extinct. Coeff. $M^{-1}cm^{-1}$ | Quantum yield |
|---|---|---|---|---|---|
| Wild type | None | 395 (475) | 508 | 21,000 (7,150) | 0.77 |
| P4 | Y66H | 383 | 447 | 13,500 | 0.21 |
| P4-3 | Y66H Y145F | 381 | 445 | 14,000 | 0.38 |
| W7 | Y66W N146I M153T V163A N212K | 433 (453) | 475 (501) | 18,000 (17,100) | 0.67 |
| W2 | Y66W I123V Y145H H148R M153T V163A N212K | 432 (453) | 480 | 10,000 (9,600) | 0.72 |
| S65T | S65T | 489 | 511 | 39,200 | 0.68 |
| P4-1 | S65T M153A K238E | 504 (396) | 514 | 14,500 (8,600) | 0.53 |

TABLE A-continued

| Clone | Mutation(s) | Excitation max (nm) | Emission max (nm) | Extinct. Coeff. $M^{-1}cm^{-1}$ | Quantum yield |
|---|---|---|---|---|---|
| S65A | S65A | 471 | 504 | | |
| S65C | S65C | 479 | 507 | | |
| S65L | S65L | 484 | 510 | | |
| Y66F | Y66F | 360 | 442 | | |
| Y66W | Y66W | 458 | 480 | | |

Additional mutations in Aequorea-related fluorescent proteins, referred to as "folding mutations," improve the ability of fluorescent proteins to fold at higher temperatures, and to be more fluorescent when expressed in mammalian cells, but have little or no effect on the peak wavelengths of excitation and emission. It should be noted that these may be combined with mutations that influence the spectral properties of GFP to produce proteins with altered spectral and folding properties. Folding mutations include: F64L, V68L, S72A, and also T44A, F99S, Y145F, N146I, M153T or A, V163A, I167T, S175G, S205T and N212K.

Figure 1B:
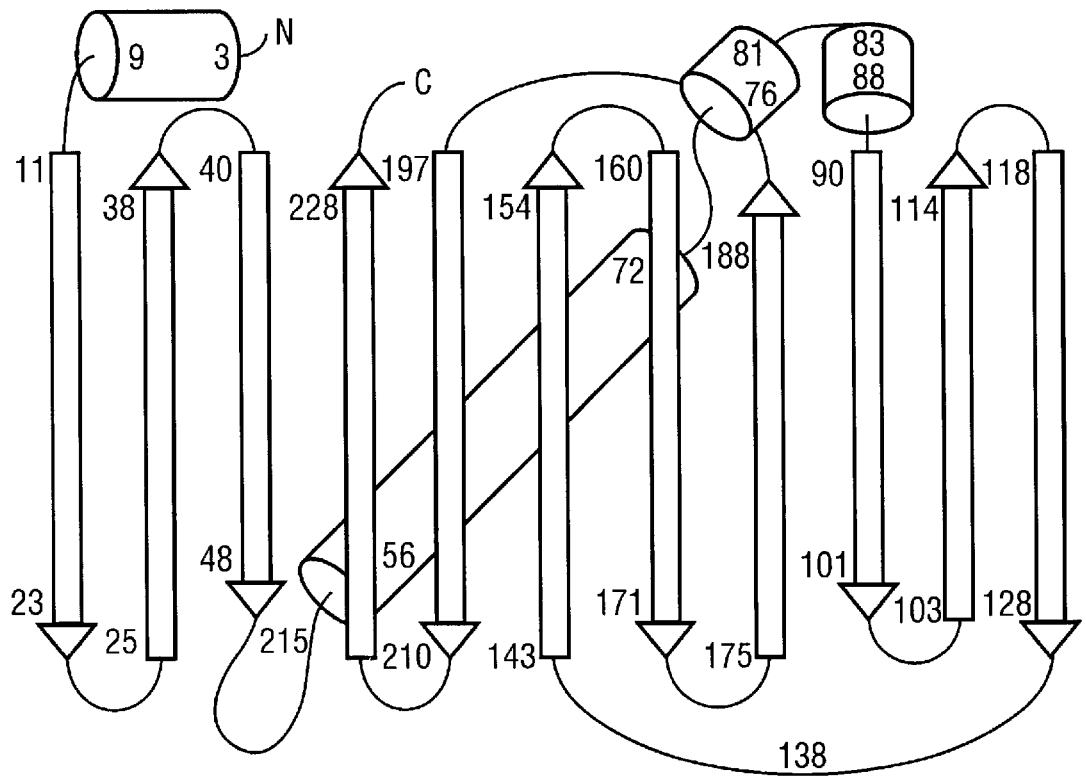

As used herein, the term "loop domain" refers to an amino acid sequence of an Aequorea-related fluorescent protein that connects the amino acids involved in the secondary structure of the eleven strands of the β-barrel or the central α-helix (residues 56–72) (see FIGS. 1A and 1B).

As used herein, the "fluorescent protein moiety" of a fluorescent protein is that portion of the amino acid sequence of a fluorescent protein which, when the amino acid sequence of the fluorescent protein substrate is optimally aligned with the amino acid sequence of a naturally occurring fluorescent protein, lies between the amino terminal and carboxy terminal amino acids, inclusive, of the amino acid sequence of the naturally occurring fluorescent protein.

It has been found that fluorescent proteins can be genetically fused to other target proteins and used as markers to identify the location and amount of the target protein produced. Accordingly, this invention provides fusion proteins comprising a fluorescent protein moiety and additional amino acid sequences. Such sequences can be, for example, up to about 15, up to about 50, up to about 150 or up to about 1000 amino acids long. The fusion proteins possess the ability to fluoresce when excited by electromagnetic radiation. In one embodiment, the fusion protein comprises a polyhistidine tag to aid in purification of the protein.

B. Use of the Crystal Structure of Green Fluorescent Protein to Design Mutants Having Altered Fluorescent Characteristics Using X-ray crystallography and computer processing, we have created a model of the crystal structure of Aequorea green fluorescent protein showing the relative location of the atoms in the molecule. This information is useful in identifying amino acids whose substitution alters fluorescent properties of the protein.

Fluorescent characteristics of Aequorea-related fluorescent proteins depend, in part, on the electronic environment of the chromophore. In general, amino acids that are within about 0.5 nm of the chromophore influence the electronic environment of the chromophore. Therefore, substitution of such amino acids can produce fluorescent proteins with altered fluorescent characteristics. In the excited state, electron density tends to shift from the phenolate towards the carbonyl end of the chromophore. Therefore, placement of increasing positive charge near the carbonyl end of the chromophore tends to decrease the energy of the excited state and cause a red-shift in the absorbance and emission wavelength maximum of the protein. Decreasing positive charge near the carbonyl end of the chromophore tends to have the opposte effect, causing a blue-shift in the protein's wavelengths.

Amino acids with charged (ionized D, E, K, and R), dipolar (H, N, Q, S, T, and uncharged D, E and K), and polarizable side groups (e.g., C, F, H, M, W and Y) are useful for altering the electronic environment of the chromophore, especially when they substitute an amino acid with an uncharged, nonpolar or non-polarizable side chain. In general, amino acids with polarizable side groups alter the electronic environment least, and, consequently, are expected to cause a comparatively smaller change in a fluorescent property. Amino acids with charged side groups alter the environment most, and, consequently, are expected to cause a comparatively larger change in a fluorescent property. However, amino acids with charged side groups are more likely to disrupt the structure of the protein and to prevent proper folding if buried next to the chromophore without any additional solvation or salt bridging. Therefore charged amino acids are most likely to be tolerated and to give useful effects when they replace other charged or highly polar amino acids that are already solvated or involved in salt bridges. In certain cases, where substitution with a polarizable amino acid is chosen, the structure of the protein may make selection of a larger amino acid, e.g., W, less appropriate. Alternatively, positions occupied by amino acids with charged or polar side groups that are unfavorably oriented may be substituted with amino acids that have less charged or polar side groups. In another alternative, an amino acid whose side group has a dipole oriented in one direction in the protein can be substituted with an amino acid having a dipole oriented in a different direction.

More particularly, Table B lists several amino acids located within about 0.5 nm from the chromophore whose substitution can result in altered fluorescent characteristics. The table indicates, underlined, preferred amino acid substitutions at the indicated location to alter a fluorescent characteristic of the protein. In order to introduce such substitutions, the table also provides codons for primers used in site directed mutagenesis involving amplification. These primers have been selected to encode economically the preferred amino acids, but they encode other amino acids as well, as indicated, or even a stop codon, denoted by Z. In introducing substitutions using such degenerate primers the most efficient strategy is to screen the collection to identify mutants with the desired properties and then sequence their DNA to find out which of the possible substitutions is responsible. Codons are shown in double-stranded form with sense strand above, antisense stand below. In nucleic acid sequences, R=(A or g); Y=(C or T); M=(A or C); K=(g or T); S=(g or C); W=(A or T); H=(A, T, or C); B=(g, T, or C); V=(g, A, or C); D=(g, A, or T); N=(A, C, g, or T).

TABLE B

| Original position and presumed role | | Change to | Codon |
|---|---|---|---|
| L42 | Aliphatic residue near C=N of chromophore | C<u>FH</u>LQR<u>W</u>YZ | 5'YDS 3' 3'RHS 5' |
| V61 | Aliphatic residue near central —CH= of chromophore | <u>FYH</u>CLR | YDC RHg |
| T62 | Almost directly above center of chromophore bridge | A<u>V</u>FS | KYC MRg |
| | | DEHK<u>N</u>Q | VAS BTS |
| | | <u>FYH</u>CLR | YDC RHg |

TABLE B-continued

| Original position and presumed role | | Change to | Codon |
|---|---|---|---|
| V68 | Aliphatic residue near carbonyl and G67 | <u>FYH</u>L | YWC RWg |
| N121 | Near C-N Site of ring closure between T65 and G67 | C<u>FH</u>LQR<u>W</u>YZ | YDS RHS |
| Y145 | Packs near tyrosine ring of chromophore | <u>WCF</u>L | TKS AMS |
| | | DEH<u>N</u>KQ | VAS BTS |
| H148 | H-bonds to phenolate oxygen | <u>FY</u>NI | WWC WWg |
| | | KQR | MRg KYC |
| V150 | Aliphatic residue near tyrosine ring of chromophore | <u>FYH</u>L | YWC RWg |
| F165 | Packs near tyrosine ring | C<u>H</u>QR<u>W</u>YZ | YRS RYS |
| I167 | Aliphatic residue near phenolate; I167T has effects | <u>FYH</u>L | YWC RWg |
| T203 | H-bonds to phenolic oxygen of chromophore | <u>FH</u>LQR<u>W</u>YZ | YDS RHS |
| E222 | Protonation regulates ionization of chromophore | HK<u>N</u>Q | MAS KTS |

Examples of amino acids with polar side groups that can be substituted with polarizable side groups include, for example, those in Table C.

TABLE C

| Original position and presumed role | | Change to | Codon |
|---|---|---|---|
| Q69 | Terminates chain of H-bonding waters | K<u>REG</u> | RRg YYC |
| Q94 | H-bonds to carbonyl terminus of chromophore | D<u>EH</u>K<u>N</u>Q | VAS BTS |
| Q183 | Bridges Arg96 and center of chromophore bridge | <u>HY</u> | YAC RTG |
| | | <u>EK</u> | RAg YTC |
| N185 | Part of H-bond network near carbonyl of chromophore | DEH<u>N</u>KQ | VAS BTS |

In another embodiment, an amino acid that is close to a second amino acid within about 0.5 nm of the chromophore can, upon substitution, alter the electronic properties of the second amino acid, in turn altering the electronic environment of the chromphore. Table D presents two such amino acids. The amino acids, L220 and V224, are close to E222 and oriented in the same direction in the β pleated sheet.

TABLE D

| Original position and presumed role | | Change to | Codon |
|---|---|---|---|
| L220 | Packs next to Glu222; to make GFP pH sensitive | <u>H</u>K<u>NPQT</u> | MMS KKS |
| Y224 | Packs next to Glu222; to make GFP pH sensitive | <u>H</u>K<u>NPQT</u> | MMS KKS |
| | | C<u>FH</u>LQR<u>W</u>YZ | YDS RHS |

One embodiment of the invention includes a nucleic acid molecule comprising a nucleotide sequence encoding a functional engineered fluorescent protein whose amino acid sequence is substantially identical to the amino acid sequence of Aequorea green fluorescent protein (SEQ ID NO:2) and which differs from SEQ ID NO:2 by at least a substitution at Q69, wherein the functional engineered fluorescent protein has a different fluorescent property than Aequorea green fluorescent protein. Preferably, the substitution at Q69 is selected from the group of K, R, E and G.

The Q69 substitution can be combined with other mutations to improve the properties of the protein, such as a functional mutation at S65.

One embodiment of the invention includes a nucleic acid molecule comprising a nucleotide sequence encoding a functional engineered fluorescent protein whose amino acid sequence is substantially identical to the amino acid sequence of Aequorea green fluorescent protein (SEQ ID NO:2) and which differs from SEQ ID NO:2 by at least a substitution at E222, but not including E222G, wherein the functional engineered fluorescent protein has a different fluorescent property than Aequorea green fluorescent protein. Preferably, the substitution at E222 is selected from the group of N and Q. The E222 substitution can be combined with other mutations to improve the properties of the protein, such as a functional mutation at F64.

One embodiment of the invention includes a nucleic acid molecule comprising a nucleotide sequence encoding a functional engineered fluorescent protein whose amino acid sequence is substantially identical to the amino acid sequence of Aequorea green fluorescent protein (SEQ ID NO:2) and which differs from SEQ ID NO:2 by at least a substitution at Y145, wherein the functional engineered fluorescent protein has a different fluorescent property than Aequorea green fluorescent protein.

Preferably, the substitution at Y145 is selected from the group of W, C, F, L, E, H, K and Q. The Y145 substitution can be combined with other mutations to improve the properties of the protein, such as a Y66.

The invention also includes computer related embodiments, including computational methods of using the crystal coordinates for designing new fluorescent protein mutations and devices for storing the crystal data, including coordinates. For instance the invention includes a device comprising a storage device and, stored in the device, at least 10 atomic coordinates selected from the atomic coordinates listed in FIGS. 5-A to 5AT. More coordinates can be storage depending of the complexity of the calculations or the objective of using the coordinates (e.g. about 100, 1,000, or more coordinates). For example, larger numbers of coordinates will be desirable for more detailed representations of fluorescent protein structure. Typically, the storage device is a computer readable device that stores code that it receives as input the atomic coordinates. Although, other storage meand as known in the art are contemplated. The computer readable device can be a floppy disk or a hard drive.

C. Production of Long Wavelength Engineered Fluorescent Proteins

Recombinant production of a fluorescent protein involves expressing a nucleic acid molecule having sequences that encode the protein.

In one embodiment, the nucleic acid encodes a fusion protein in which a single polypeptide includes the fluorescent protein moiety within a longer polypeptide. The longer polypeptide can include a second functional protein, such as FRET partner or a protein having a second function (e.g., an enzyme, antibody or other binding protein). Nucleic acids that encode fluorescent proteins are useful as starting materials.

The fluorescent proteins can be produced as fusion proteins by recombinant DNA technology. Recombinant production of fluorescent proteins involves expressing nucleic acids having sequences that encode the proteins. Nucleic acids encoding fluorescent proteins can be obtained by methods known in the art. Fluorescent proteins can be made by site-specific mutagenesis of other nucleic acids encoding fluorescent proteins, or by random mutagenesis caused by increasing the error rate of PCR of the original polynucleotide with 0.1 mM $MnCl_2$ and unbalanced nucleotide concentrations. See, e.g., U.S. patent application Ser. No. 08/337,915, filed Nov. 10, 1994 or International application PCT/US95/14692, filed Nov. 10, 1995. The nucleic acid encoding a green fluorescent protein can be isolated by polymerase chain reaction of cDNA from *A. victoria* using primers based on the DNA sequence of *A. victoria* green fluorescent protein, as presented in FIG. 3. PCR methods are described in, for example, U.S. Pat. No. 4,683,195; Mullis et al. (1987) *Cold Spring Harbor Symp. Quant. Biol.* 51:263; and Erlich, ed., *PCR Technology,* (Stockton Press, NY, 1989).

The construction of expression vectors and the expression of genes in transfected cells involves the use of molecular cloning techniques also well known in the art. Sambrook et al., *Molecular Cloning—A Laboratory Manual,* Cold Spring Harbor Laboratory, Cold Spring Harbor, N.Y., (1989) and *Current Protocols in Molecular Biology,* F. M. Ausubel et al., eds., (Current Protocols, a joint venture between Greene Publishing Associates, Inc. and John Wiley & Sons, Inc.). The expression vector can be adapted for function in prokaryotes or eukaryotes by inclusion of appropriate promoters, replication sequences, markers, etc.

Nucleic acids used to transfect cells with sequences coding for expression of the polypeptide of interest generally will be in the form of an expression vector including expression control sequences operatively linked to a nucleotide sequence coding for expression of the polypeptide. As used, the term "nucleotide sequence coding for expression of" a polypeptide refers to a sequence that, upon transcription and translation of mRNA, produces the polypeptide. This can include sequences containing, e.g., introns. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods which are well known to those skilled in the art can be used to construct expression vectors containing the fluorescent protein coding sequence and appropriate transcriptional/translational control signals. These methods include in vitro recombinant DNA techniques, synthetic techniques and in vivo recombination/genetic recombination. (See, for example, the techniques described in Maniatis, et al., *Molecular Cloning A Laboratory Manual,* Cold Spring Harbor Laboratory, N.Y., 1989).

Transformation of a host cell with recombinant DNA may be carried out by conventional techniques as are well known to those skilled in the art. Where the host is prokaryotic, such as *E. coli,* competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Preferably, a eukaryotic host is utilized as the host cell as described herein.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

In one embodiment recombinant fluorescent proteins can be produced by expression of nucleic acid encoding for the protein in *E. coli*. Aequorea-related fluorescent proteins are best expressed by cells cultured between about 15° C. and 30° C. but higher temperatures (e.g. 37° C.) are possible. After synthesis, these enzymes are stable at higher temperatures (e.g., 37° C.) and can be used in assays at those temperatures.

A variety of host-expression vector systems may be utilized to express fluorescent protein coding sequence. These include but are not limited to microorganisms such as bacteria transformed with recombinant bacteriophage DNA, plasmid DNA or cosmid DNA expression vectors containing a fluorescent protein coding sequence; yeast transformed with recombinant yeast expression vectors containing the fluorescent protein coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a fluorescent protein coding sequence; insect cell systems infected with recombinant virus expression vectors (e.g., baculovirus) containing a fluorescent protein coding sequence; or animal cell systems infected with recombinant virus expression vectors (e.g., retroviruses, adenovirus, vaccinia virus) containing a fluorescent protein coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516–544, 1987). For example, when cloning in bacterial systems, inducible promoters such as pL of bacteriophage α, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted fluorescent protein coding sequence.

In bacterial systems a number of expression vectors may be advantageously selected depending upon the use intended for the fluorescent protein expressed. For example, when large quantities of the fluorescent protein are to be produced, vectors which direct the expression of high levels of fusion protein products that are readily purified may be desirable. Those which are engineered to contain a cleavage site to aid in recovering fluorescent protein are preferred.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp.516–544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673–684, 1987; and The Molecular Biology of the Yeast Saccharomyces, Eds. Strathem et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol.11, A Practical Approach, Ed. DM Glover, IRL Press, Wash., D.C., 1986). Alternatively, vectors may be used which promote integration of foreign DNA sequences into the yeast chromosome.

In cases where plant expression vectors are used, the expression of a fluorescent protein coding sequence may be driven by any of a number of promoters. For example, viral promoters such as the 35S RNA and 19S RNA promoters of CaMV (Brisson, et al., *Nature* 310:511–514, 1984), or the coat protein promoter to TMV (Takamatsu, et al., *EMBO J.* 6:307–311, 1987) may be used; alternatively, plant promoters such as the small subunit of RUBISCO (Coruzzi, et al., 1984, *EMBO J.* 3:1671–1680; Broglie, et al., *Science* 224:838–843, 1984); or heat shock promoters, e.g., soybean hsp17.5-E or hsp17.3-B (Gurley, et al., *Mol. Cell. Biol.* 6:559–565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, *Methods for Plant Molecular Biology*, Academic Press, NY, Section VIII, pp. 421–463, 1988; and Grierson & Corey, *Plant Molecular Biology*, 2d Ed., Blackie, London, Ch. 7–9, 1988.

An alternative expression system which could be used to express fluorescent protein is an insect system. In one such system, *Autographa californica* nuclear poly-hedrosis virus (AcNPV) is used as a vector to express foreign genes. The virus grows in *Spodoptera frugiperda* cells. The fluorescent protein coding sequence may be cloned into non-essential regions (for example, the polyhedrin gene) of the virus and placed under control of an AcNPV promoter (for example the polyhedrin promoter). Successful insertion of the fluorescent protein coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., *J. Viol.* 46:584, 1983; Smith, U.S. Pat. No. 4,215,051.

Eukaryotic systems. and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of fluorescent protein. Such host cell lines may include but are not limited to CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, the fluorescent protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fluorescent protein in infected hosts (e.g., see Logan & Shenk, *Proc. Natl. Acad. Sci. USA*, 81: 3655–3659, 1984). Alternatively, the vaccinia virus 7.5K promoter may be used. (e.g., see, Mackett, et al., *Proc. Natl. Acad. Sci. USA,*79: 7415–7419, 1982; Mackett, et al., i J. Virol. 49: 857–864, 1984; Panicali, et al., *Proc. Natl. Acad. Sci. USA* 79: 4927–4931, 1982). Of particular interest are vectors based on bovine papilloma virus which have the ability to replicate as extrachromosomal elements (Sarver, et al., *Mol. Cell. Biol.* 1: 486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fluorescent protein gene in host cells (Cone & Mulligan, *Proc. Natl. Acad. Sci.USA,* 81:6349–6353, 1984). High level expression may also be achieved using inducible promoters, including, but not limited to, the metallothionine IIA promoter and heat shock promoters.

The invention can also include a localization sequence, such as a nuclear localization sequence, an endoplasmic reticulum localization sequence, a peroxisome localization sequence, a mitochondrial localization sequence, or a localized protein. Localization sequences can be targeting sequences which are described, for example, in "Protein Targeting", chapter 35 of Stryer, L., *Biochemistry* (4th ed.). W.. Freeman, 1995. The localization sequence can also be a localized protein. Some important localization sequences include those targeting the nucleus (KKKRK), mitochondrion (amino terminal MLRTSSLFTRRVQPSLFRNILRLQST-), endoplasmic reticulum (KDEL at C-terminus, assuming a signal sequence present at N-terminus), peroxisome (SKF at C-terminus), prenylation or insertion into plasma membrane (CaaX, CC, CXC, or CCXX at C-terminus), cytoplasmic side of plasma membrane (fusion to SNAP-25), or the Golgi apparatus (fusion to furin).

For long-term, high-yield production of recombinant proteins, stable expression is preferred. Rather than using expression vectors which contain viral origins of replication, host cells can be transformed with the fluorescent protein cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell,* 11: 223, 1977), hypoxanthine-guanine phosphoribosyltransferase (Szybalska & Szybalski, *Proc. Natl. Acad. Sci. USA,* 48:2026, 1962), and adenine phosphoribosyltransferase (Lowvy, et al., *Cell,* 22: 817, 1980) genes can be employed in tk$^-$, hgprt$^-$ or aprt$^-$ cells respectively. Also, antimetabolite resistance can be used as the basis of selection for dhfr, which confers resistance to methotrexate (Wigler, et al., *Proc. Natl. Acad. Sci. USA,* 77: 3567, 1980; O'Hare, et al., *Proc. Natl. Acad. Sci. USA,* 8: 1527, 1981); gpt, which confers resistance to mycophenolic acid (Mulligan & Berg, *Proc. Natl. Acad. Sci. USA,* 78: 2072, 1981; neo, which confers resistance to the aminoglycoside G-418 (Colberre-Garapin, et al., *J. Mol. Biol.,* 150:1, 1981); and hygro, which confers resistance to hygromycin (Santerre, et al., *Gene,* 30: 147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA,* 85:8047, 1988); and ODC (ornithine decarboxylase) which confers resistance to the ornithine decarboxylase inhibitor, 2-(difluoromethyl)-DL-ornithine, DFMO (McConlogue L., In: *Current Communications in Molecular Biology,* Cold Spring Harbor Laboratory, ed., 1987).

DNA sequences encoding the fluorescence protein polypeptide of the invention can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

The expression vector can be transfected into a host cell for expression of the recombinant nucleic acid. Host cells can be selected for high levels of expression in order to purify the fluorescent protein fusion protein. *E. coli* is useful for this purpose. Alternatively, the host cell can be a prokaryotic or eukaryotic cell selected to study the activity of an enzyme produced by the cell. In this case, the linker peptide is selected to include an amino acid sequence recognized by the protease. The cell can be, e.g., a cultured cell or a cell in vivo.

A primary advantage of fluorescent protein fusion proteins is that they are prepared by normal protein biosynthesis, thus completely avoiding organic synthesis and the requirement for customized unnatural amino acid analogs. The constructs can be expressed in *E. coli* in large scale for in vitro assays. Purification from bacteria is simplified when the sequences include polyhistidine tags for one-step purification by nickel-chelate chromatography. Alternatively, the substrates can be expressed directly in a desired host cell for assays in situ.

In another embodiment, the invention provides a transgenic non-human animal that expresses a nucleic acid sequence which encodes the fluorescent protein.

The "non-human animals" of the invention comprise any non-human animal having nucleic acid sequence which encodes a fluorescent protein. Such non-human animals include vertebrates such as rodents, non-human primates, sheep, dog, cow, pig, amphibians, and reptiles. Preferred non-human animals are selected from the rodent family including rat and mouse, most preferably mouse. The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al., *Proc. Natl. Acad. Sci. USA* 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

Retroviral infection can also be used to introduce transgene into a non-human animal. The developing non-human embryo can be cultured in vitro to the blastocyst stage. During this time, the blastomeres can be targets for retro viral infection (Jaenich, R., *Proc. Natl.Acad. Sci. USA* 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., *Proc. Natl. Acad. Sci. USA* 82:6927–6931, 1985; Van der Putten, et al., *Proc. Natl. Acad. Sci. USA* 82:6148–6152, 1985). Transfection is easily and efficiently obtained by culturing the blastomeres on a monolayer of virus-producing cells (Van der Putten, supra; Stewart, et al., *EMBO J.* 6:383–388, 1987). Alternatively, infection can be performed at a later stage. Virus or virus-producing cells can be injected into the blastocoele (D. Jahner et al., *Nature* 298:623–628, 1932). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retro viral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. *Nature* 292:154–156, 1981; M. O. Bradley et al., *Nature* 309: 255–258, 1984; Gossler, et al., *Proc. Natl. Acad. Sci. USA* 83: 9065–9069, 1986; and Robertson et al., *Nature* 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode which encodes the fluorescent protein which may be expressed in a transgenic non-human animal. The term "transgenic" as used herein additionally includes any organism whose genome has been altered by in vitro manipulation of the early embryo or fertilized egg or by any transgenic technology to induce a specific gene knock-out. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

III. Uses of Engineered Fluorescent Proteins

The proteins of this invention are useful in any methods that employ fluorescent proteins.

The engineered fluorescent proteins of this invention are useful as fluorescent markers in the many ways fluorescent markers already are used. This includes, for example, coupling engineered fluorescent proteins to antibodies, nucleic acids or other receptors for use in detection assays, such as immunoassays or hybridization assays.

The engineered fluorescent proteins of this invention are useful to track the movement of proteins in cells. In this embodiment, a nucleic acid molecule encoding the fluorescent protein is fused to a nucleic acid molecule encoding the protein of interest in an expression vector. Upon expression inside the cell, the protein of interest can be localized based on fluorescence. In another version, two proteins of interest are fused with two engineered fluorescent proteins having different fluorescent characteristics.

The engineered fluorescent proteins of this invention are useful in systems to detect induction of transcription. In certain embodiments, a nucleotide sequence encoding the engineered fluorescent protein is fused to expression control sequences of interest and the expression vector is transfected into a cell. Induction of the promoter can be measured by detecting the expression and/or quantity of fluorescence. Such constructs can be used used to follow signaling pathways from receptor to promoter.

The engineered fluorescent proteins of this invention are useful in applications involving FRET. Such applications can detect events as a function of the movement of fluorescent donors and acceptor towards or away from each other. One or both of the donor/acceptor pair can be a fluorescent protein. A preferred donor and receptor pair for FRET based assays is a donor with a T203I mutation and an acceptor with the mutation T203X, wherein X is an aromatic amino acid-39, especially T203Y, T203W, or T203H. In a particularly useful pair the donor contains the following mutations: S72A, K79R, Y145F, M153A and T203I (with a excitation peak of 395 nm and an emission peak of 511 nm) and the acceptor contains the following mutations S65G, S72A, K79R, and T203Y. This particular pair provides a wide separation between the excitation and emission peaks of the donor and provides good overlap between the donor emission spectrum and the acceptor excitation spectrum. Other red-shifted mutants, such as those described herein, can also be used as the acceptor in such a pair.

In one aspect, FRET is used to detect the cleavage of a substrate having the donor and acceptor coupled to the substrate on opposite sides of the cleavage site. Upon cleavage of the substrate, the donor/acceptor pair physically separate, eliminating FRET. Assays involve contacting the substrate with a sample, and determining a qualitative or quantitative change in FRET. In one embodiment, the engineered fluorescent protein is used in a substrate for β-lactamase. Examples of such substrates are described in U.S. Pat. No. 5,741,657 and International Application PCT/US96/04059, filed Mar. 20, 1996. In another embodiment, an engineered fluorescent protein donor/acceptor pair are part of a fusion protein coupled by a peptide having a proteolytic cleavage site. Such tandem fluorescent proteins are described in U.S. patent application Ser. No. 08/594,575, filed Jan. 31, 1996.

In another aspect, FRET is used to detect changes in potential across a membrane. A donor and acceptor are placed on opposite sides of a membrane such that one translates across the membrane in response to a voltage change. This creates a measurable FRET. Such a method is described in U.S. Pat. No. 5,661,035, filed and International Application PCT/US96/09652, filed Jun. 6, 1996.

The engineered protein of this invention are useful in the creation of fluorescent substrates for protein kinases. Such substrates incorporate an amino acid sequence recognizable by protein kinases. Upon phosphorylation, the engineered fluorescent protein undergoes a change in a fluorescent property. Such substrates are useful in detecting and measuring protein kinase activity in a sample of a cell, upon transfection and expression of the substrate. Preferably, the kinase recognition site is placed within about 20 anmino acids of a terminus of the engineered fluorescent protein. The kinase recognition site also can be placed in a loop domain of the protein. (See, e.g. FIG. 1B.) Methods for making fluorescent substrates for protein kinases are described in U.S. patent application Ser. No. 08/680,877, filed Jul. 16, 1996.

A protease recognition site also can be introduced into a loop domain. Upon cleavage, fluorescent property changes im a measurable fashion.

The invention also includes a method of identifying a test chemical. Typically, the method includes contacting a test chemical a sample containing a biological entity labeled with a functional, engineered fluorescent protein or a polynucleotide encoding said functional, engineered fluorescent protein. By monitoring fluorescence (i.e. a fluorescent property) from the sample containing the functional engineered fluorescent protein it can be determined whether a test chemical is active. Controls can be included to insure the specificity of the signal. Such controls include measurements of a fluorescent property in the absence of the test chemical, in the presence of a chemical with an expected activity (e.g., a known modulator) or engineered controls (e.g., absence of engineered fluorescent protein, absence of engineered fluorescent protein polynucleotide or the absence of operably linkage of the engineered fluorescent protein).

The fluorescence in the presence of a test chemical can be greater or less than in the absence of said test chemical. For instance if the engineered fluorescent protein is used a reporter of gene expression, the test chemical may up or down regulate gene expression. For such types of screening, the polynucleotide encoding the functional, engineered fluorescent protein is operatively linked to a genomic polynucleotide or a re. Alternatively, the functional, engineered fluorescent protein is fused to second functional protein. This embodiment can be used to track localization of the second protein or to track protein-protein interactions using energy transfer.

IV. Procedures

Fluorescence in a sample is measured using a fluorimeter. In general, excitation radiation from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation. This process can be miniaturized and automated to enable screening many thousands of compounds.

Methods of performing assays on fluorescent materials are well known in the art and are described in, e.g., Lakowicz, J. R., *Principles of Fluorescence Spectroscopy*, New York:Plenum Press (1983); Herman, B., Resonance energy transfer microscopy, in: *Fluorescence Microscopy of Living Cells in Culture, Part B, Methods in Cell Biology*, vol. 30, ed. Taylor, D. L. & Wang, Y.-L., San Diego: Academic Press (1989), pp. 219–243; Turro, N. J., *Modern Molecular Photochemistry*, Menlo Park: Benjamin/Cummings Publishing Col, Inc. (1978), pp. 296–361.

The following examples are provided by way of illustration, not by way of limitation.

EXAMPLES

As a step in understanding the properties of GFP, and to aid in the tailoring of GFPs with altered characteristics, we have determined the three dimensional structure at 1.9 Å resolution of the S65T mutant (R. Heim et al. *Nature* 373:664–665 (1995)) of *A. victoria* GFP. This mutant also contains the ubiquitous Q80R substitution, which accidentally occurred in the early distribution of the GFP cDNA and is not known to have any effect on the protein properties (M. Chalfie et al. *Science* 263:802–805 (1994)).

Histidine-tagged S65T GFP (R. Heim et al. *Nature* 373:664–665 (1995)) was overexpressed in JM109/pRSET$_B$ in 4 1 YT broth plus ampicillin at 37°, 450 rpm and 5 l/min air flow. The temperature was reduced to 25° at $A_{595}$=0.3, followed by induction with 1 mM isopropylthiogalactoside for 5 h. Cell paste was stored at −80° overnight, then was resuspended in 50 mM HEPES pH 7.9, 0.3 M NaCl, 5 mM 2-mercaptoethanol, 0.1 mM phenylmethyl-sulfonylfluoride (PMSF), passed once through a French press at 10,000 psi, then centrifuged at 20 K rpm for 45 min. The supernatant was applied to a Ni-NTA-agarose column (Qiagen), followed by a wash with 20 mM imidazole, then eluted with 100 mM imidazole. Green fractions were pooled and subjected to chymotryptic (Sigma) proteolysis (1:50 w/w) for 22 h at RT. After addition of 0.5 mM PMSF, the digest was reapplied to the Ni column. N-terminal sequencing verified the presence of the correct N-terminal methionine. After dialysis against 20 mM HEPES, pH 7.5 and concentration to $A_{490}$=20, rod-shaped crystals were obtained at RT in hanging drops containing 5 µL protein and 5 µL well solution, 22–26% PEG 4000 (Serva), 50 mM HEPES pH 8.0–8.5, 50 mM $MgCl_2$ and 10 mM 2-mercapto-ethanol within 5 days. Crystals were 0.05 mm across and up to 1.0 mm long. The space group is $P2_12_12_1$ with a=51.8, b=62.8, c=70.7 Å, Z=4. Two crystal forms of wild-type GFP, unrelated to the present form, have been described by M. A. Perrozo, K. B. Ward, R. B. Thompson, & W. W. Ward. *J. Biol. Chem.* 203, 7713–7716 (1988).

The structure of GFP was determined by multiple isomorphous replacement and anomalous scattering (Table E), solvent flattening, phase combination and crystallographic refinement. The most remarkable feature of the fold of GFP is an eleven stranded β-barrel wrapped around a single central helix (FIGS. 1A and 1B), where each strand consists of approximately 9–13 residues. The barrel forms a nearly perfect cylinder 42 Å long and 24 Å in diameter. The N-terminal half of the polypeptide comprises three antiparallel strands, the central helix, and then 3 more antiparallel strands, the latter of which (residues 118–123) is parallel to the N-terminal strand (residues 11–23). The polypeptide backbone then crosses the "bottom" of the molecule to form the second half of the barrel in a five-strand Greek Key motif. The top end of the cylinder is capped by three short, distorted helical segments, while one short, very distorted helical segment caps the bottom of the cylinder. The main-chain hydrogen bonding lacing the surface of the cylinder very likely accounts for the unusual stability of the protein towards denaturation and proteolysis. There are no large segments of the polypeptide that could be excised while preserving the intactness of the shell around the chromophore. Thus it would seem difficult to re-engineer GFP to reduce its molecular weight (J. Dopf & T. M. Horiagon *Gene* 173:39–43 (1996)) by a large percentage.

Figure 2A:
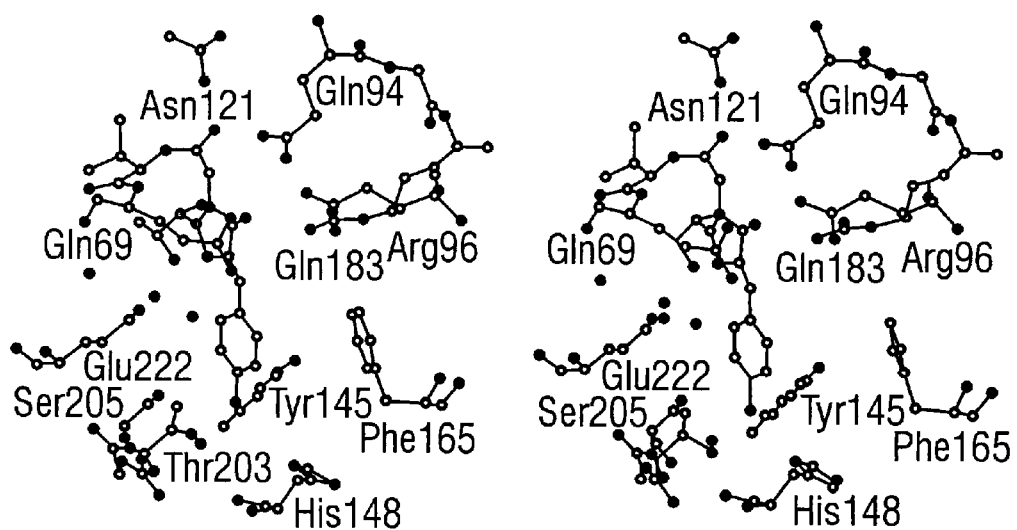
FIGS. 2A–2C. (A) Stereo drawing of the chromophore and residues in the immediate vicinity. Carbon atoms are drawn as open circles, oxygen is filled and nitrogen is shaded. Solvent molecules are shown as isolated filled circles. (B) Portion of the final $2F_o$–$F_c$ electron density map contoured at 1.0-, showing the electron density surrounding the chromophore. (C) Schematic diagram showing the first and second spheres of coordination of the chromophore. Hydrogen bonds are shown as dashed lines and have the indicated lengths in Å. Inset: proposed structure of the carbinolamine intermediate that is presumably formed during generation of the chromophore.
Figure 2B:
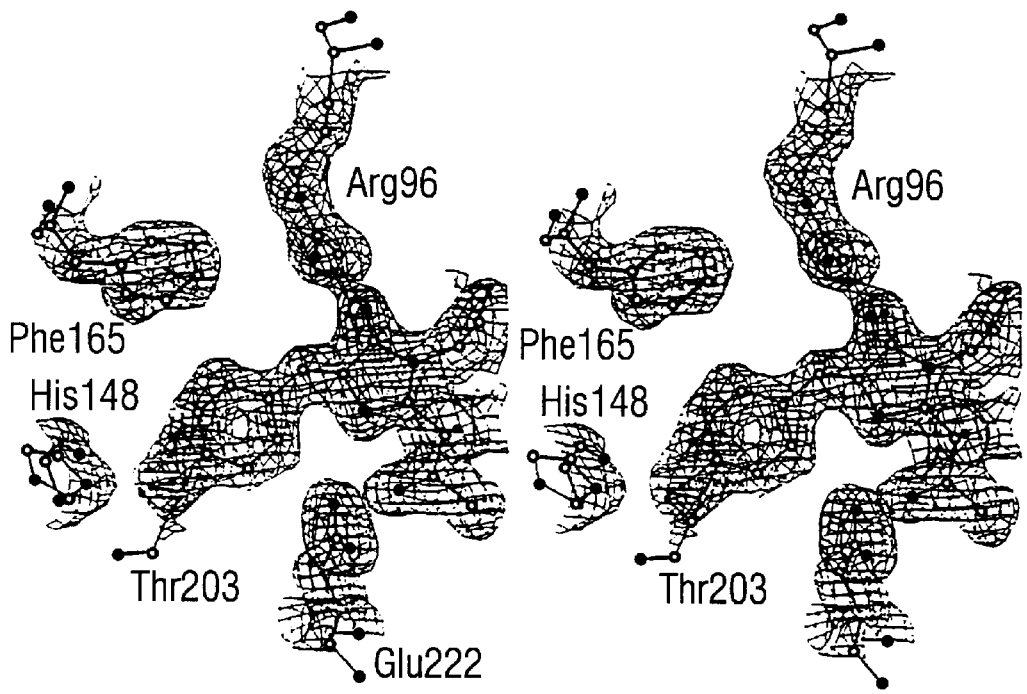

The p-hydroxybenzylideneimidazolidinone chromophore (C. W. Cody et al. *Biochemistry* 32:1212–1218 (1993)) is completely protected from bulk solvent and centrally located in the molecule. The total and presumably rigid encapsulation is probably responsible for the small Stokes' shift (i.e. wavelength difference between excitation and emission maxima), high quantum yield of fluorescence, inability of $O_2$ to quench the excited state (B. D. Nageswara Rao et al. *Biophys. J.* 32:630–632 (1980)), and resistance of the chromophore to titration of the external pH (W. W. Ward. *Bioluminescence and Chemiluminescence* (M. A. DeLuca and W. D. McElroy, eds) Academic Press pp. 235–242 (1981); W. W. Ward & S. H. Bokman. *Biochemistry* 21:4535–4540 (1982); W. W. Ward et al. *Photochem. Photobiol.* 35:803–808 (1982)). It also allows one to rationalize why fluorophore formation should be a spontaneous intramolecular process (R. Heim et al. *Proc. Nat. Acad. Sci. USA* 91:12501–12504 (1994)), as it is difficult to imagine how an enzyme could gain access to the substrate. The plane of the chromophore is roughly perpendicular (60°) to the symmetry axis of the surrounding barrel. One side of the chromophore faces a surprisingly large cavity, that occupies a volume of approximately 135 Å$^3$ (B. Lee & F. M. Richards. *J. Mol. Biol.* 55:379–400 (1971)). The atomic radii were those of Lee & Richards, calculated using the program MS with a probe radius of 1.4 Å. (M. L. Connolly, *Science* 221:709–713 (1983)). The cavity does not open out to bulk solvent. Four water molecules are located in the cavity, forming a chain of hydrogen bonds linking the buried side chains of $Glu^{222}$ and $Gln^{69}$. Unless occupied, such a large cavity would be expected to de-stabilize the protein by several kcal/mol (S. J. Hubbard et al., *Protein Engineering* 7:613–626 (1994); A. E. Eriksson et al. *Science* 255:178–183 (1992)). Part of the volume of the cavity might be the consequence of the compaction resulting from cyclization and dehydration reactions. The cavity might also temporarily accommodate the oxidant, most likely $O_2$ (A. B. Cubitt et al. *Trends Biochem. Sci.* 20:448–455 (1995); R. Heim et al. *Proc. Natl. Acad. Sci.* USA 91:12501–12504 (1994); S. Inouye & F. I. Tsuji. *FEBS Lett.* 351:211–214 (1994)), that dehydrogenates the α-β-bond of $Tyr^{66}$. The chromophore, cavity, and side chains that contact the chromophore are shown in FIG. 2A and a portion of the final electron density map in this vicinity in 2B.

Figure 2C:
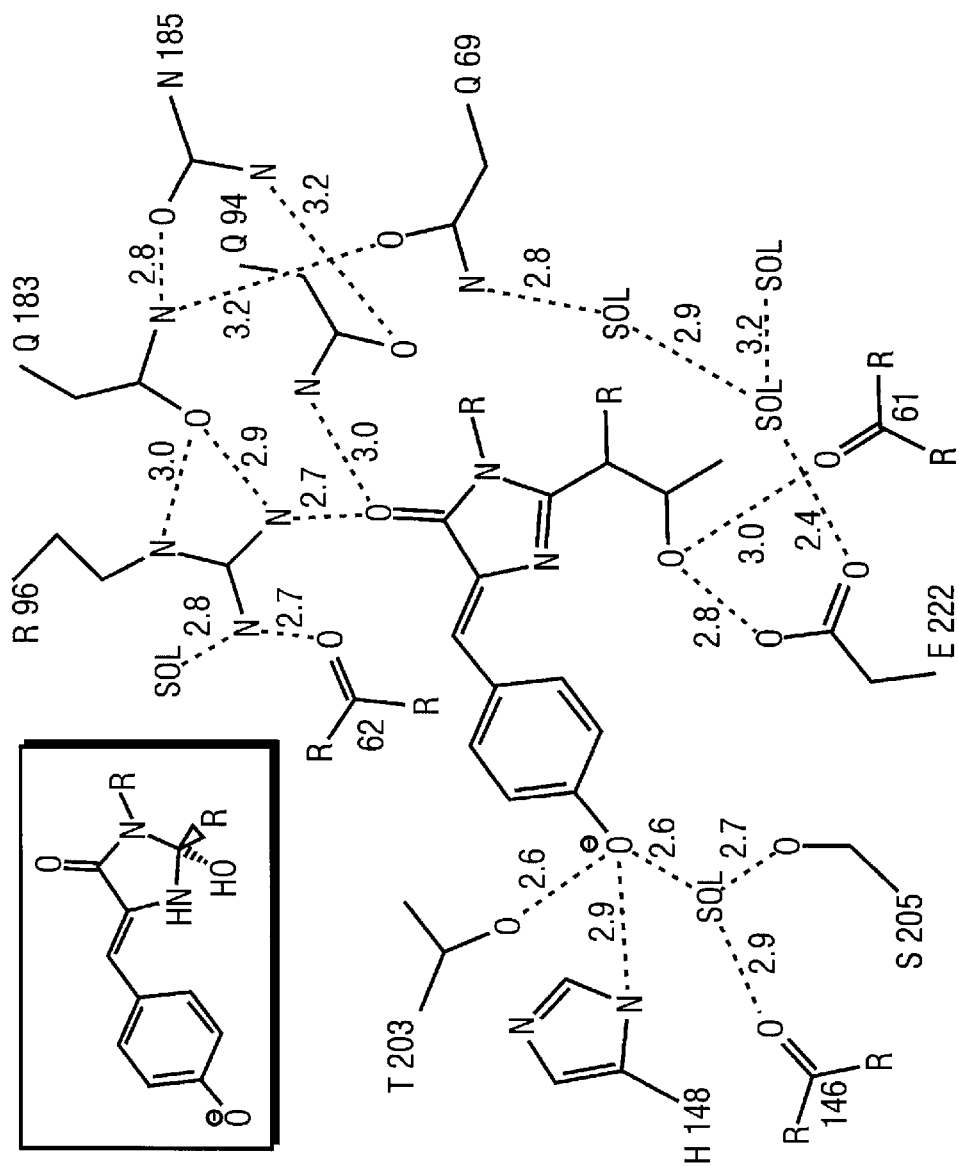
Figure 6:
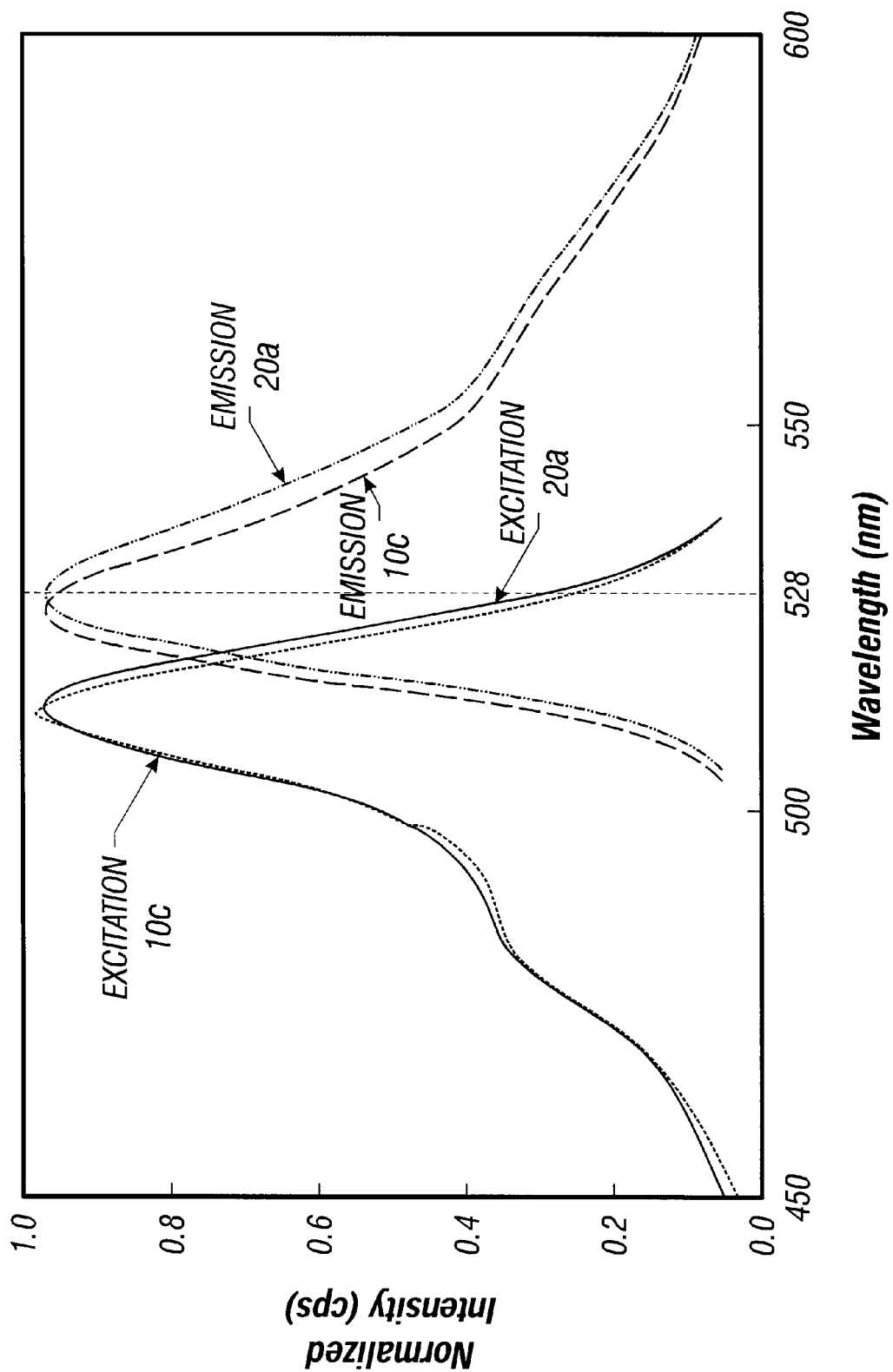
FIG. 6 shows the fluorescence excitation and emission spectra for engineered fluorescent proteins 20A and 10C (Table F). The vertical line at 528 nm compares the emission maxima of 10C, to the left of the line, and 20A, to the right of the line.

The opposite side of the chromophore is packed against several aromatic and polar side chains. Of particular interest is the intricate network of polar interactions with the chromophore (FIG. 2C). $His^{148}$, $Thr^{203}$ and $Ser^{203}$ form hydrogen bonds with the phenolic hydroxyl; $Arg^{96}$ and $Gin^{94}$ interact with the carbonyl of the imidazolidinone ring and $Glu^{222}$ forms a hydrogen bond with the side chain of $Thr^{65}$. Additional polar interactions, such as hydrogen bonds to $Arg^{96}$ from the carbonyl of $Thr^{62}$, and the side-chain carbonyl of $Gln^{183}$, presumably stabilize the buried $Arg^{96}$ in its protonated form. In turn, this buried charge suggests that a partial negative charge resides on the carbonyl oxygen of the imidazolidinone ring of the deprotonated fluorophore, as has previously been suggested (W. W. Ward. *Bioluminescence and Chemiluminescence* (M. A. DeLuca and W. D. McElroy, eds) Academic Press pp. 235–242 (1981); W. W. Ward & S. H. Bokman. *Biochemistry* 21:4535–4540 (1982); W. W. Ward et al. *Photochem. Photobiol.* 35:803–808 (1982)). $Arg^{96}$ is likely to be essential for the formation of the fluorophore, and may help catalyze the initial ring closure. Finally, $Tyr^{145}$ shows a typical stabilizing edge-face interaction with the benzyl ring. $Trp^{57}$, the only tryptophan in GFP, is located 13 Å to 15 Å from the chromophore and the long axes of the two ring systems are nearly parallel. This indicates that efficient energy transfer to the latter should occur, and explains why no separate tryptophan emission is observable (D. C. Prasher et al. *Gene* 111:229–233 (1992). The two cysteines in GFP, $Cys^{48}$ and $Cys^{70}$, are 24 Å apart, too distant to form a disulfide bridge. $Cys^{70}$ is buried, but $Cys^{48}$ should be relatively accessible to sulfhydryl-specific reagents. Such a reagent, 5,5'-dithiobis(2-nitrobenzoic acid), is reported to label GFP and quench its fluorescence (S. Inouye & F. I. Tsuji *FEBS Lett.* 351:211–214 (1994)). This effect was attributed to the necessity for a free sulfhydryl, but could also reflect specific quenching by the 5-thio-2-nitrobenzoate moiety that would be attached to $Cys^{48}$.

Although the electron density map is for the most part consistent with the proposed structure of the chromophore (D. C. Prasher et al. *Gene* 111:229–233 (1992); C. W. Cody et al. *Biochemistry* 32:1212–1218 (1993)) in the cis [Z-] configuration, with no evidence for any substantial fraction of the opposite isomer around the chromophore double bond, difference features are found at >σ in the final ($F_o$–$F_c$) electron density map that can be interpreted to represent either the intact, uncyclized polypeptide or a carbinolamine (inset to FIG. 2C). This suggests that a significant fraction, perhaps as much as 30% of the molecules in the crystal, have failed to undergo the final dehydration reaction. Confirmation of incomplete dehydration comes from electrospray mass spectrometry, which consistently shows that the average masses of both wild-type and S65T GFP (31,086±4 and 31,099.5±4 Da, respectively) are 6–7 Da higher than predicted (31,079 and 31,093 Da, respectively) for the fully matured proteins. Such a discrepancy could be explained by a 30–35% mole fraction of apoprotein or carbinolamine with 18 or 20 Da higher molecular weight The natural abundance of $^{13}C$ and $^{2}H$ and the finite resolution of the Hewlett-Packard 5989B electrospray mass spectrometer used to make these measurements do not permit the individual peaks to be resolved, but instead yields an average mass peak with a full width at half maximum of approximately 15 Da. The molecular weights shown include the His-tag, which has the sequence MRGSHHHHHH GMASMTGGQQM GRDLYD-DDDK DPPAEF (SEQ ID NO:5). Mutants of GFP that increase the efficiency of fluorophore maturation might yield somewhat brighter preparations. In a model for the apoprotein, the $Thr^{65}$-$Tyr^{66}$ peptide bond is approximately in the α-helical conformation, while the peptide of $Tyre^{66}$-$Gly^{67}$ appears to be tipped almost perpendicular to the helix axis by its interaction with $Arg^{96}$. This further supports the speculation that $Arg^{96}$ is important in generating the conformation required for cyclization, and possibly also for promoting the attack of $Gly^{67}$ on the carbonyl carbon of $Thr^{65}$ (A. B. Cubitt et al. *Trends Biochem. Sci.* 20:448–455 (1995)).

The results of previous random mutagenesis have implicated several amino acid side chains to have substantial effects on the spectra and the atomic model confirms that these residues are close to the chromophore. The mutations T203I and E222G have profound but opposite consequences on the absorption spectrum (T. Ehrig et al. *FEBS Letters* 367:163–166 (1995)). T203I (with wild-type $Ser^{65}$) lacks the 475 nm absorbance peak usually attributed to the anionic chromophore and shows only the 395 nm peak thought to reflect the neutral chromophore (R. Heim et al. *Proc. Natl. Acad. Sci. USA* 91:12501–12504 (1994); T. Ehrig et al. *FEBS Letters* 367:163–166 (1995)). Indeed, $Thr^{203}$ is hydrogen-bonded to the phenolic oxygen of the chromophore, so replacement by Ile should hinder ionization of the phenolic oxygen. Mutation of $Glu^{222}$ to Gly (T. Ehrig et al. *FEBS Letters* 367:163–166 (1995)) has much the same spectroscopic effect as replacing $Ser^{65}$ by Gly, Ala, Cys, Val, or Thr, namely to suppress the 395 nm peak in favor of a peak at 470–490 nm (R. Heim et al. *Natutre* 373:664–665 (1995); S. Delagrave et al. *Bio/Technology* 13:151–154 (1995)). Indeed $Glu^{222}$ and the remnant of $Thr^{65}$ are hydrogen-bonded to each other in the present structure, probably with the uncharged carboxyl of $Glu^{222}$ acting as donor to the side chain oxygen of $Thr^{65}$. Mutations E222G, S65G, S65A, and S65V would all suppress such H-bonding. To explain why only wild-type protein has both excitation peaks, $Ser^{65}$, unlike $Thr^{65}$, may adopt a conformation in which its hydroxyl donates a hydrogen bond to and stabilizes $Glu^{222}$ as an anion, whose charge then inhibits ionization of the chromophore. The structure also explains why some mutations seem neutral. For example, $Gln^{80}$ is a surface residue far removed from the chromophore, which explains why its accidental and ubiquitous mutation to Arg seems to have no obvious intramolecular spectroscopic effect (M. Chalfie et al. *Science* 263:802–805 (1994)).

The development of GFP mutants with red-shifted excitation and emission maxima is an interesting challenge in protein engineering (A. B. Cubitt et al. *Trends Biochem. Sci.* 20:448–455 (1995); R. Heim et al. *Nature* 373:664–665 (1995); S. Delagrave et al. *Bio/Technology* 13:151–154 (1995)). Such mutants would also be valuable for avoidance of cellular autofluorescence at short wavelengths, for simultaneous multicolor reporting of the activity of two or more cellular processes, and for exploitation of fluorescence resonance energy transfer as a signal of protein-protein interaction (R. Heim & R. Y. Tsien. *Current Biol.* 6:178–182 (1996)). Extensive attempts using random mutagenesis have shifted the emission maximum by at most 6 nm to longer wavelengths, to 514 nm (R. Heim & R. Y. Tsien. *Current Biol.* 6:178–182 (1996)); previously described "red-shifted" mutants merely suppressed the 395 nm excitation peak in favor of the 475 nm peak without anv sigiuficant reddening of the 505 nm emission (S. Delagrave et al. *Bio/Technology* 13:151–154 (1995)). Because $Thr^{203}$ is revealed to be adjacent to the phenolic end of the chromophore, we mutated it to polar aromatic residues such as His, Tyr, and Trp in the hope that the additional polarizability of their π systems would lower the energy of the excited state of the adjacent chromophore. All three substitutions did indeed shift the emission peak to greater than 520 nm (Table F). A particularly attractive mutation was T203Y/S65G/V68L/S72A, with excitation and emission peaks at 513 and 527 nm respectively. These wavelengths are sufficiently different from previous GFP mutants to be readily distinguishable by appropriate filter sets on a fluorescence microscope. The extinction coefficient, 36,500 $M^{-1}cm^{-1}$, and quantum yield, 0.63, are almost as high as those of S65T (R. Heim et al. *Nature* 373:664–665 (1995)).

Comparison of Aequorea GFP with other protein pigments is instructive. Unfortunately, its closest characterized homolog, the GFP from the sea pansy *Renilla reniformis* (O. Shimomura and F. H. Johnson *J. Cell. Comp. Physiol.* 59:223 (1962); J. G. Morin and J. W. Hastings, *J. Cell. Physiol.* 77:313 (1971); H. Morise et al. *Biochemistry* 13:2656 (1974); W. W. Ward *Photochem. Photobiol. Reviews* (Smith, K. C. ed.) 4:1 (1979); W. W. Ward. *Bioluminescence and Chemiluminescence* (M. A. DeLuca and W. D. McElroy, eds) Academic Press pp. 235–242 (1981); W. W. Ward & S. H. Bokman *Biochemistry* 21:4535–4540 (1982); W. W. Ward et al. *Photochem. Photobiol.* 35:803–808 (1982)), has not been sequenced or cloned, though its chromophore is derived from the same FSYG sequence as in wild-type Aequorea GFP (R. M. San Pietro et al. *Photochem. Photobiol.* 57:63S (1993)). The closest analog for which a three dimensional structure is available is the photoactive yellow protein (PYP, G. E. O. Borgstahl et al. *Biochemistry* 34:6278–6287 (1995)), a 14-kDa photoreceptor from halophilic bacteria. PYP in its native dark state absorbs maximally at 446 nm and transduces light with a quantum yield of 0.64, rather closely matching wild-type GFP's long wavelength absorbance maximum near 475 nm and fluorescence quantum yield of 0.72–0.85. The fundamental chromophore in both proteins is an anionic p-hydroxycinnamyl group, which is covalently attached to the protein via a thioester linkage in PYP and a heterocyclic iminolactam in GFP. Both proteins stabilize the negative charge on the chromophore with the help of buried cationic arginine and neutral glutamic acid groups, $Arg^{52}$ and $Glu^{46}$ in PYP and $Arg^{96}$ and $Glu^{222}$ in GFP, though in PYP the residues are close to the oxyphenyl ring whereas in GFP they are nearer the carbonyl end of the chromophore. However, PYP has an overall α/β fold with appropriate flexibility and signal transduction domains to enable it to mediate the cellular phototactic response, whereas GFP is a much more regular and rigid β-barrel to minimize parasitic dissipation of the excited state energy as thermal or conformational motions. GFP is an elegant example of how a visually appealing and extremely useful function, efficient fluorescence, can be spontaneously generated from a cohesive and economical protein structure.

A. Summary of GFP Structure Determination

Data were collected at room temperature in house using either Molecular Structure Corp. R-axis II or San Diego Multiwire Systems (SDMS) detectors (Cu K□) and later at beamline X4A at the Brookhaven National Laboratory at the selenium absorption edge (□=0.979 Å) using image plates. Data were evaluated using the HKL package (Z. Otwinowski, in *Proceedings of the CCP4 Study Weekend: Data Collection and Processing*, L. Sawyer, N. Issacs, S. Bailey, Eds. (Science and Engineering Research Council (SERC), Daresbury Laboratory, Warrington, UK, (1991)), pp 56–62; W. Minor, XDISPLAYF (Purdue University, West Lafayette, Ind., 1993)) or the SDMS software (A. J. Howard et al. *Meth. Enzymol.* 114:452–471 (1985)). Each data set was collected from a single crystal. Heavy atom soaks were 2 mM in mother liquor for 2 days. Initial electron density maps were based on three heavy atom derivatives using in-house data, then later were replaced with the synchrotron data. The EMTS difference Patterson map was solved by inspection, then used to calculate difference Fourier maps of the other derivatives. Lack of closure refinement of the heavy atom parameters was performed using the Protein package (W. Steigemann, in Ph.D. Thesis (Technical University, Munich, 1974)). The MIR maps were much poorer than the overall figure of merit would suggest, and it was clear that the EMTS isomorphous differences dominated the phasing. The enhanced anomalous occupancy for the synchrotron data provided a partial solution to the problem. Note that the phasing power was reduced for the synchrotron data, but the figure of merit was unchanged. All experimental electron density maps were improved by solvent flattening using the program DM of the CCP4 (CCP4: *A Suite of Programs for Protein Crystallography* (SERC Daresbury Laboratory, Warrington WA4 4AD UK, 1979)) package assuming a solvent content of 38%. Phase combination was performed with PHASCO2 of the Protein package using a weight of 1.0 on the atomic model. Heavy atom parameters were subsequently improved by refinement against combined phases. Model building proceeded with FRODO and O (T. A. Jones et al. *Acta. Crystallogr. Sect. A* 47:110 (1991); T. A. Jones, in *Computational Crystallography* D. Sayre, Ed. (Oxford University Press, Oxford, 1982) pp. 303–317) and crystallographic refinement was performed with the TNT package (D. E. Tronrud et al. *Acta Cryst. A* 43:489–503 (1987)). Bond lengths and angles for the chromophore were estimated using CHEM3D (Cambridge Scientific Computing). Final refinement and model building was performed against the X4A selenomethione data set, using $(2F_o-F_c)$ electron density maps. The data beyond 1.9 Å resolution have not been used at this stage. The final model contains residues 2–229 as the terminal residues are not visible in the electron density map, and the side chains of several disordered surface residues have been omitted. Density is weak for residues 156–158 and coordinates for these residues are unreliable. This disordering is consistent with previous analyses showing that residues 1 and 233–238 are dispensible but that further truncations may prevent fluorescence (J. Dopf & T. M. Horiagon. *Gene* 173:39–43 (1996)). The atomic model has been deposited in the Protein Data Bank (access code 1EMA).

TABLE E

Diffraction Data Statistics

| Crystal | Resolution (Å) | Total obs | Unique obs | Compl. (%)[a] | Compl. (shell)[b] | Rmerge (%)[c] | Riso (%)[d] |
|---|---|---|---|---|---|---|---|
| R-axix II | | | | | | | |
| Native | 2.0 | 51907 | 13582 | 80 | 69 | 4.1 | 5.8 |
| EMTS[e] | 2.6 | 17727 | 6787 | 87 | 87 | 5.7 | 20.6 |
| SeMet | 2.3 | 44975 | 10292 | 92 | 88 | 10.2 | 9.3 |
| Multiwire | | | | | | | |
| HGI4-Se | 3.0 | 15380 | 4332 | 84 | 79 | 7.2 | 28.8 |
| X4a | | | | | | | |
| SeMet | 1.8 | 126078 | 19503 | 80 | 55 | 9.3 | 9.4 |
| EMTS | 2.3 | 57812 | 9204 | 82 | 66 | 7.2 | 26.3 |

Phasing Statistics

| Derivative | Resolution (Å) | Number of sites | Phasing power[f] | Phasing Power (shell) | FOM[g] | FOM (shell) |
|---|---|---|---|---|---|---|
| In House | | | | | | |
| EMTS | 3.0 | 2 | 2.08 | 2.08 | 0.77 | .072 |
| SeMet | 3.0 | 4 | 1.66 | 1.28 | — | — |
| HGI4-Se | 3.0 | 9 | 1.77 | 1.90 | — | — |
| X4a | | | | | | |
| EMTS | 3.0 | 2 | 1.36 | 1.26 | 0.77 | .072 |
| SeMet | 3.0 | 4 | 1.31 | 1.08 | — | — |

Atomic Model Statistics

| | |
|---|---|
| Protein atoms | 1790 |
| Solvent atoms | 94 |
| Resol. range (Å) | 20–1.9 |
| Number of reflections (F > 0) | 17676 |
| Completeness | 84. |
| R. factor[h] | 0.175 |
| Mean B-value (Å²) | 24.1 |

Deviations from ideality

| | |
|---|---|
| Bondlengths (Å) | 0.014 |
| Bond angles (□) | 1.9 |
| Restrained B-values (Å²) | 4.3 |
| Ramachandran outliers | 0 |

Notes:
[a]Completeness is the ratio of observed reflections to theoretically possible expressed as a percentage.
[b]Shell indicates the highest resolution shell, typically 0.1–0.4 Å wide.
[c]Rmerge = |I − <I>|/ I, where <I> is the mean of individual observations of intensities I.
[d]Riso = |$I_{DER} − I_{NAT}$|/ $I_{NAT}$
[e]Derivatives were EMTS = ethymercurithiosalicylate (residues modified Cys[48] and Cys[70]), SeMet = selenomethionine substituted protein (Met[1] and Met[233] could not be located); HgI4 − SeMet = double derivative HgI4 on SeMet background.
[f]Phasing power = <$F_h$>/<E> where <$F_H$> = r.m.s. heavy atom scattering and <E> = lack of closure.
[g]FOM, mean figure of merit
[h]Standard crystallographic R-factor, R = ||$F_{obs}$| − |$F_{calc}$||/ |$F_{obs}$|

B. Spectral Properties of Thr[203] ("T203") Mutants Compared to S65T

The mutations F64L, V68L and S72A improve the folding of GFP at 37□ (B. P. Cormack et al. *Gene* 173:33 (1996)) but do not significantly shift the emssion spectra.

TABLE F

| Clone | Mutations | Excitation max. (nm) | Extinction coefficient ($10^3 M^{-1} cm^{-1}$) | Emission max. (nm) |
|---|---|---|---|---|
| S65T | S65T | 489 | 39.2 | 511 |
| 5B | T203H/S65T | 512 | 19.4 | 524 |
| 6C | T203Y/S65T | 513 | 14.5 | 525 |
| 10B | T203Y/F64L/S65G/S72A | 513 | 30.8 | 525 |
| 10C | T203Y/F65G/V68L/S72A | 513 | 36.5 | 527 |
| 11 | T203W/S65G/S72A | 502 | 33.0 | 512 |
| 12H | T203Y/S65G/S72A | 513 | 36.5 | 527 |
| 20A | T203Y/S65G/V68L/Q69K/S72A | 515 | 46.0 | 527 |

The present invention provides novel long wavelength engineered fluorescent proteins. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A nucleic acid molecule comprising a nucleotide sequence encoding a functional engineered fluorescent protein whose amino acid sequence is substantially identical to the amino acid sequence of Aequorea green fluorescent protein (SEQ ID NO:2) and which differs from SEQ ID NO:2 by
   1) at least the substitution T203X, wherein X is an aromatic amino acid selected from H, Y, W or F, and
   2) a substitution at S65, wherein the substitution is selected from S65G, S65T, S65A, S65L, S65C, S65V or S65I, and
   wherein said functional engineered fluorescent protein has a different fluorescent property than Aequorea green fluorescent protein.

2. The nucleic acid molecule of claim 1 wherein the amino acid sequence differs by no more than the substitutions S65T/T203H; S65T/T203Y; S72A/F64L/S65G/T203Y; S72A/S65G/V68L/T203Y; S65G/V68L/Q69K/S72A/T203Y; S65G/S72A/T203Y; or S65G/S72A/T203W.

3. The nucleic acid molecule of claim 1 wherein the amino acid sequence further comprises a substitution at Y66, wherein the substitution is selected from Y66H, Y66F, and Y66W.

4. The nucleic acid molecule of claim 1 wherein the amino acid sequence further comprises a mutation at a position selected from the group consisting of Y145, N146, H148, M153, and V163.

5. Tie nucleic acid molecule of claim 1 wherein the amino acid sequence further comprises a folding mutation selected from the group consisting of F64L, V68L and S72A.

6. The nucleic acid molecule of claim 1 wherein tile nucleotide sequence encoding the protein differs from the nucleotide sequence of SEQ ID NO:1 by the substitution of at least one codon by a preferred mammalian codon.

7. The nucleic acid molecule of claim 1 encoding a fusion protein wherein the fusion protein comprises a polypeptide of interest and the functional engineered fluorescent protein.

8. An expression vector comprising expression control sequences operatively linked to a nucleic acid molecule comprising a nucleotide sequence encoding a functional engineered fluorescent protein whose amino acid sequence is substantially identical to the amino acid sequence of Aequorea green fluorescent protein (SEQ ID NO;2) and which differs from SEQ ID NO:2 by
 1) at least the substitution T203X, wherein X is an aromatic amino acid selected from H, Y, W or F, and
 2) a substitution at S65, wherein the substitution is selected from S65G, S65T, S65A, S65L, S65C, S65V or S65I, and
 wherein said functional engineered fluorescent protein has a different fluorescent property than Aequorea green fluorescent protein.

9. The expression vector of claim 8 wherein the amino acid sequence differs by no more than the substitutions S65T/T203H; S65T/T203Y; S72A/F64L/S65G/T203Y; S72A/S65G/V68L/T203Y; S65G/V68L/Q69K/S72A/T203Y, S65G/S72A/T203Y; or S65G/S72A/T203W.

10. The expression vector of claim 8 wherein the amino acid sequence further comprises a substitution at Y66, wherein the substitution is selected from Y66H, Y66F, and Y66W.

11. The expression vector of claim 8 wherein the amino acid sequence further comprises a mutation at a position selected from the group consisting of Y145, N146, H148, M153, and V163.

12. The expression vector of claim 8 wherein the amino acid sequence further comprises a folding mutation selected from the group consisting of F64L, V68L and S72A.

13. The expression vector of claim 8 wherein the nucleotide sequence encoding the protein differs from the nucleotide sequence of SEQ ID NO:1 by the substitution of at least one codon by a preferred mammalian codon.

14. The expression vector of claim 8 encoding a fusion protein wherein the fusion protein comprises a polypeptide of interest and the functional engineered fluorescent protein.

15. A recombinant host cell comprising an expression vector that comprises expression control sequences operatively linked to a nucleic acid molecule comprising a nucleic acid molecule comprising a nucleotide sequence encoding a functional engineered fluorescent protein whose amino acid sequence is substantially identical to the amino acid sequence of Aequorea green fluorescent protein (SEQ ID NO:2) and which differs from SEQ ID NO:2 by
 1) at least the substitution T203X, wherein X is an aromatic amino acid selected from H, Y, W or F, and
 2) a substitution at S65, wherein the substitution is selected from S65G, S65T, S65A, S65L, S65C, S65V or S65I, and
 wherein said functional engineered fluorescent protein has a different fluorescent property than Aequorea green fluorescent protein.

16. The recombinant host cell of claim 15 wherein the amino acid sequence differs by no more than the substitutions S65T/T203H; S65T/T203Y; S72A/F64L/S65G/T203Y; S72A/S65G/V68L/T203Y; S65G/V68L/Q69K/S72A/T203Y; S65G/S72A/T203Y; or S65G/S72A/T203W.

17. The recombinant host cell of claim 15 wherein the amino acid sequence further comprises a substitution at Y66, wherein the substitution is selected from Y66H, Y66F, and Y66W.

18. The recombinant host cell of claim 15 wherein the amino acid sequence further comprises a mutation at a position selected from the group consisting of Y145, N146, H148, M153, and V163.

19. The recombinant host cell of claim 15 wherein the amino acid sequence further comprises a folding mutation selected from the group consisting of F64L, V68L and S72A.

20. The recombinant host cell of any of claims 15–17 wherein the nucleotide sequence encoding the protein differs from the nucleotide sequence of SEQ ID NO:1 by the substitution of at least one codon by a preferred mammalian codon.

21. The recombinant host cell of any of claims 15–17 encoding a fusion protein wherein the fusion protein comprises a polypeptide of interest and the functional engineered fluorescent protein.

22. The recombinant host cell of any of claims 15–17 which is a prokaryotic cell.

23. The recombinant host cell of any of claims 15–17 which is an eukaryotic cell.

* * * * *

UNITED STATES PATENT AND TRADEMARK OFFICE
CERTIFICATE OF CORRECTION

PATENT NO.   : 6,403,374 B1
DATED        : June 11, 2002
INVENTOR(S)  : Tsien et al.

It is certified that error appears in the above-identified patent and that said Letters Patent is hereby corrected as shown below:

<u>Title page,</u>
Item [73], Assignee, replace "The Regents of the University of California, Oakland, CA (US)"
with
-- The Regents of the University of California, Oakland, CA (US); and State of Oregon acting through the State Higher Board of Education on behalf of The University of Oregon, Eugene, OR (US) --.

Signed and Sealed this

Twelfth Day of November, 2002

Attest:

Attesting Officer

JAMES E. ROGAN
*Director of the United States Patent and Trademark Office*